US012790600B2

(12) United States Patent
Stabach et al.

(10) Patent No.: US 12,790,600 B2
(45) Date of Patent: Nov. 10, 2026

(54) ENPP1 POLYPEPTIDES AND METHODS OF USING SAME

(71) Applicant: Yale University, New Haven, CT (US)

(72) Inventors: Paul Stabach, New Haven, CT (US); Demetrios Braddock, New Haven, CT (US)

(73) Assignee: Yale University, New Haven, CT (US)

( * ) Notice: Subject to any disclaimer, the term of this patent is extended or adjusted under 35 U.S.C. 154(b) by 118 days.

(21) Appl. No.: 18/815,173

(22) Filed: Aug. 26, 2024

(65) Prior Publication Data

US 2025/0230423 A1 Jul. 17, 2025

Related U.S. Application Data

(63) Continuation of application No. 17/601,387, filed as application No. PCT/US2020/026643 on Apr. 3, 2020, now abandoned.

(60) Provisional application No. 62/984,650, filed on Mar. 3, 2020, provisional application No. 62/983,142, filed on Feb. 28, 2020, provisional application No. 62/830,230, filed on Apr. 5, 2019.

(51) Int. Cl.

| | |
|---|---|
| *A61K 38/00* | (2006.01) |
| *A61P 19/00* | (2006.01) |
| *C07K 19/00* | (2006.01) |
| *C12N 9/14* | (2006.01) |
| *C12N 9/16* | (2006.01) |
| *C12N 15/85* | (2006.01) |

(52) U.S. Cl.

CPC ............ *C12N 9/14* (2013.01); *C07K 2319/02* (2013.01); *C07K 2319/30* (2013.01); *C07K 2319/50* (2013.01); *C12Y 301/04001* (2013.01); *C12Y 306/01009* (2013.01)

(58) Field of Classification Search

None

See application file for complete search history.

(56) References Cited

U.S. PATENT DOCUMENTS

| | | | |
|---|---|---|---|
| 5,428,130 | A | 6/1995 | Capon et al. |
| 5,968,508 | A | 10/1999 | Goldfine et al. |
| 6,043,056 | A | 3/2000 | Yue et al. |
| 6,358,923 | B1 | 3/2002 | Yue et al. |
| 7,323,542 | B2 | 1/2008 | Balian et al. |
| 7,888,372 | B2 | 2/2011 | Millan et al. |
| 8,846,603 | B2 | 9/2014 | Quinn et al. |
| 9,744,219 | B2 | 8/2017 | Braddock et al. |
| 9,913,881 | B2 | 3/2018 | Braddock et al. |
| 10,064,917 | B2 | 9/2018 | Braddock et al. |
| 10,213,483 | B2 | 2/2019 | Otterlei et al. |
| 10,213,484 | B2 | 2/2019 | Braddock et al. |
| 10,493,135 | B2 | 12/2019 | Braddock et al. |
| 10,517,927 | B2 | 12/2019 | Braddock et al. |
| 10,583,170 | B2 | 3/2020 | Braddock et al. |
| 10,624,958 | B2 | 4/2020 | Braddock et al. |
| 2003/0190311 | A1 | 10/2003 | Dall Acqua et al. |
| 2007/0004913 | A1 | 1/2007 | Challita-Eid et al. |
| 2007/0015145 | A1 | 1/2007 | Woolf et al. |
| 2008/0273206 | A1 | 11/2008 | Genge et al. |
| 2010/0203076 | A1 | 8/2010 | Fotin-Mleczek et al. |
| 2014/0154774 | A1 | 6/2014 | Quinn et al. |
| 2014/0349369 | A1 | 11/2014 | Buechler et al. |
| 2014/0377859 | A1 | 12/2014 | Quinn et al. |
| 2015/0024460 | A1 | 1/2015 | Quinn et al. |
| 2015/0359858 | A1 | 12/2015 | Braddock et al. |
| 2016/0184387 | A1 | 6/2016 | Charmot et al. |
| 2016/0184458 | A1 | 6/2016 | Heartlein |
| 2017/0340713 | A1 | 11/2017 | Braddock et al. |
| 2017/0340714 | A1 | 11/2017 | Braddock et al. |
| 2017/0354719 | A1 | 12/2017 | Braddock et al. |

FOREIGN PATENT DOCUMENTS

| | | | |
|---|---|---|---|
| CN | 107109381 | A | 8/2017 |
| EP | 3298140 | A1 | 3/2018 |
| JP | 2005-501514 | A | 1/2005 |
| JP | 2008188015 | A | 8/2008 |
| JP | 2018-516566 | A | 6/2018 |
| RU | 2013142583 | A | 4/2015 |
| RU | 2016107788 | A | 11/2018 |
| WO | 0239994 | A2 | 5/2002 |
| WO | 02092020 | A2 | 11/2002 |
| WO | 03040340 | A2 | 5/2003 |
| WO | 2006135925 | A2 | 12/2006 |
| WO | 2008105911 | A2 | 9/2008 |
| WO | 2011113027 | A2 | 9/2011 |
| WO | 2012125182 | A1 | 9/2012 |
| WO | 2014126965 | A2 | 8/2014 |
| WO | 2016100803 | A2 | 6/2016 |
| WO | 2016187408 | A1 | 11/2016 |
| WO | 2017087936 | A1 | 5/2017 |
| WO | 2017191274 | A2 | 11/2017 |
| WO | 2018027024 | A1 | 2/2018 |
| WO | 2018/157165 | A1 | 8/2018 |

OTHER PUBLICATIONS

Mackenzie, et al. "New insights into NPP1 function: lessons from clinical and animal studies." Bone 51.5 (2012): 961-968.

Nitschke, Y et al. "Generalized arterial calcification of infancy and pseudoxanthoma elasticum can be caused by mutations in either ENPP1 or ABCC6." The American Journal of Human Genetics 90.1 (2012): 25-39.

Nitschke, et al. "Generalized arterial calcification of infancy and pseudoxanthoma elasticum: two sides of the same coin." Frontiers in genetics 3 (2012): 302.

(Continued)

*Primary Examiner* — Manjunath N Rao
*Assistant Examiner* — Jae W Lee
(74) *Attorney, Agent, or Firm* — Saul Ewing LLP; Kathryn Doyle; Domingos J. Silva

(57) ABSTRACT

The present disclosure includes ENPP1 mutant polypeptides with improved in vivo half-lives.

21 Claims, 30 Drawing Sheets

Specification includes a Sequence Listing.

(56) References Cited

OTHER PUBLICATIONS

Rutsch, et al. "Genetics in arterial calcification: pieces of a puzzle and cogs in a wheel." Circulation research 109.5 (2011): 578-592.
Nitschke, et al. "Inherited arterial calcification syndromes: etiologies and treatment concepts." Current osteoporosis reports 15 (2017): 255-270.
Dohler, et al. "Crystal structure and substrate binding mode of ectonucleotide phosphodiesterase/pyrophosphatase-3 (NPP3)." Scientific reports 8.1 (2018): 1-13.
Li, et al. "Serum phosphate concentration and incidence of stroke: a systemic review and meta-analysis." Neurological sciences 35.12 (2014): 1877-1882.
Kassim (Clinical Advances in Hematology & Oncology vol. 14, Issue May 5, 2016 pp. 307-309).
Rath, et al. "Fc-fusion proteins and FcRn: structural insights for longer-lasting and more effective therapeutics." Critical reviews in biotechnology 35.2 (2015): 235-254.
Yin, et al. "Glycoengineering of Chinese hamster ovary cells for enhanced erythropoietin N-glycan branching and sialylation." Biotechnology and bioengineering 112.11 (2015): 2343-2351.
Supplementary European Search Report for European Patent Application No. 19855284.6 dated Apr. 21, 2022.
Dall'Acqua, et al. "Increasing the affinity of a human IgG1 for the neonatal Fc receptor: biological consequences." The Journal of Immunology 169.9 (2002): 5171-5180.
Extended European Search Report for European Patent Application No. 20783595.0 dated Jan. 2, 2023.
European Supplemental Partial Search Report for European Patent Application No. 14751154.7 issued Nov. 7, 2016.
Extended European Search Report for European Patent Application No. 14751154.7 issued Feb. 16, 2017.
Extended European Search Report for European Patent Application No. 16797290.0 issued Jun. 25, 2019.
Extended European Search Report for European Patent Application No. 17837677.8 issued Mar. 24, 2020.
International Search Report and Written Opinion for PCT International Application No. PCT/US2017/045280 issued Dec. 26, 2017.
Mus musculus domesticus ecto-nucleotide pyrophosphatase/ phosphodiesterase-1 mRNA, complete cds, GenBank J02700.2, Aug. 12, 2020 searched.
Notice of Panel Decision from Pre-Appeal Brief Review for U.S. Appl. No. 15/812,456 issued Dec. 2, 2020.
Notice of Reasons for Rejection for Japanese Patent Application No. 2017-560327 dated Mar. 30, 2020, 5 pages.
PCT International Search Report and Written Opinion for PCT International Application No. PCT/US2014/015945 issued Jul. 30, 2014.
PCT International Search Report and Written Opinion for PCT International Application No. PCT/US2016/033236 issued Oct. 27, 2016.
Pre-Appeal Brief for U.S. Appl. No. 15/812,456, filed Oct. 16, 2020.
UniProt Accession No. O14638, ENPP3_HUMAN, Jan. 7, 2015 [online]. [Retrieved on Jan. 19, 2017]. Retrieved from the internet <URL: http://www.uniprot.org/uniprot/O14638.txt?version=133>.
"Chronic Renal Failure: From the Perspective of Internal Medicine", Clinical Imagiology 21(11), 2005, 1142-1149 (Partial Translation).
"Pharmacokinetic Control of Biopharmaceuticals", Journal of Pharmaceutical Science and Technology, Japan, 2014, 27-32 (Partial Translation).
Albright , et al., "ENPP1-Fc prevents mortality and vascular calcifications in rodent model of generalized arterial calcification of infancy", Nat Commun. 6, 2015, 10006.
Albright , et al., "Molecular basis of purinergic signal metabolism by ectonucleotide pyrophosphatase/phosphodiesterases 4 and 1 and implications in stroke", J Biol Chem. 289(6), 2014, 3294-3306.
Albright , et al., "NPP4 is a procoagulant enzyme on the surface of vascular endothelium", Blood. 120(22), 2012, 4432-4440.
Anonymous , "UPI000511D809", Retrieved from the Internet Mar. 7, 2019, <https://www.uniprot.org/uniparc/UPI000 511D809>, Oct. 2014.
Belisário , et al., "Association between ENPP1 K173Q and stroke in a newborn cohort of 395 Brazilian children with sickle cell anemia", Blood. 126(10), 2015, 1259-1260.
Buckley , et al., "Plasma cell membrane glycoprotein PC-1. cDNA cloning of the human molecule, amino acid sequence, and chromosomal location", J Biol Chem. 265(29), Oct. 1990, 17506-17511.
Caballero , et al., "Impaired urinary osteopontin excretion in Npt2a-/- mice", Am J Physiol Renal Physiol. 312(1), 2017, F77-F83.
Calvert , et al., "The Provisional Patent Application: What You Need to Know", Inventors Eye. United States Patent and Trademark Office, Apr. 2010, 5 pages.
Cimpean , et al., "Substrate-specifying determinants of the nucleotide pyrophosphatases/phosphodiesterases NPP1 and NPP2", Biochem J. 381(Pt 1), 2004, 71-77.
Dasgupta, et al., "Mutations in SLC34A3/NPT2c are associated with kidney stones and nephrocalcinosis", J Am Soc Nephrol. 25(10), 2014, 2366-2375.
Eller , et al., "Impact of ENPP1 genotype on arterial calcification in patients with end-stage renal failure", Nephrol Dial Transplant. 23(1), 2008, 321-327.
Flanagan , et al., "Genetic mapping and exome sequencing identify 2 mutations associated with stroke protection in pediatric patients with sickle cell anemia", Blood. 121(16), 2013, 3237-3245.
Fleisch , et al., "Inhibitors and promoters of stone formation", Kidney Int. 13(5), 1978, 361-371.
Gijsbers , et al., "Functional characterization of the non-catalytic ectodomains of the nucleotide pyrophosphatase/phosphodiesterase NPP1", Biochem J. 371(Pt 2), Apr. 15, 2003, 321-330.
Goding , et al., "Physiological and pathophysiological functions of the ecto-nucleotide pyrophosphatase/phosphodiesterase family", Biochim Biophys Acta. 1638(1), 2003, 1-19.
Guo , et al., "Clinical outcomes of various continued antiplatelet therapies in patients who were administered DAPT following the implantation of drug-eluting stents and developed gastrointestinal hemorrhage", Exp Ther Med. 12(2), Aug. 2016, 1125-1129.
Jansen , et al., "ABCC6 prevents ectopic mineralization seen in pseudoxanthoma elasticum by inducing cellular nucleotide release", Proc Natl Acad Sci U S A. 110(50), 2013, 20206-20211.
Jansen , et al., "ABCC6-mediated ATP secretion by the liver is the main source of the mineralization inhibitor inorganic pyrophosphate in the systemic circulation-brief report", Arterioscler Thromb Vasc Biol. 34(9), 2014, 1985-1989.
Jansen , et al., "Proteolytic maturation and activation of autotaxin (NPP2), a secreted metastasis-enhancing lysophospholipase D", J Cell Sci. 118(Pt 14), 2005, 3081-3089.
Jansen , et al., "Structure of NPP1, an ectonucleotide pyrophosphatase/ phosphodiesterase involved in tissue calcification", Structure. 20(11), 2012, 1948-1959.
Jin-Hua , et al., "Molecular Coning and Chromosomal Localization of PD-Iβ (PDNP3), a New Member of the Human Phosphodiesterase I Genes", Genomics 45, 1997, 412-415.
Johnson , et al., "Differential mechanisms of inorganic pyrophosphate production by plasma cell membrane glycoprotein-1 and B10 in chondrocytes", Arthritis Rheum. 42(9), 1999, 1986-1997.
Johnson , et al., "Kabat database and its applications: 30 years after the first variability plot", Nucleic Acids Res. 28 (1), Jan. 2000, 214-218.
Johnson , et al., "Linked deficiencies in extracellular PP(i) and osteopontin mediate pathologic calcification associated with defective PC-1 and ANK expression", J Bone Miner Res. 18(6), 2003, 994-1004.
Johnson , et al., "Matrix vesicle plasma cell membrane glycoprotein-1 regulates mineralization by murine osteoblastic MC3T3 cells", J Bone Miner Res. 14(6), Jun. 1999, 883-892.
Johnson , et al., "The Nucleoside Triphosphate Pyrophosphohydrolase Isozyme PC-1 Directly Promotes Cartilage Calcification Through Chondrocyte Apoptosis and Increased Calcium Precipitation by Mineralizing Vesicles", The Journal of Rheumatology 28 (12), Dec. 2001, 2681-2691.

(56) References Cited

OTHER PUBLICATIONS

Kato , et al., "Crystal structure of Enpp1, an extracellular glycoprotein involved in bone mineralization and insulin signaling", Proc Natl Acad Sci U S A. 109(42), Oct. 2012, 16876-16881.

Lee , et al., "Cloning, chromosomal localization, and tissue expression of autotaxin from human teratocarcinoma cells", Biochem Biophys Res Commun. 218(3, 1996, 714-719.

Li , et al., "Inhibition of Tissue-Nonspecific Alkaline Phosphatase Attenuates Ectopic Mineralization in the Abcc6 -/- Mouse Model of PXE but Not in the Enpp1 Mutant Mouse Models of GACI", J Invest Dermatol. 139(2), Feb. 2019, 360-368.

Li , et al., "Response of Npt2a knockout mice to dietary calcium and phosphorus", PLoS One. 12(4), 2017, e0176232.

Lieben , et al., "Normocalcemia is maintained in mice under conditions of calcium malabsorption by vitamin D-induced inhibition of bone mineralization", J Clin Invest. 122(5), 2012, 1803-1805.

Millán , et al., "Enzyme replacement therapy for murine hypophosphatasia", J Bone Miner Res. 23(6), Jun. 2008, 777-787.

Okawa, et al., "Mutation in Npps in a mouse model of ossification of the posterior longitudinal ligament of the spine", Nat Genet. 19(3), Jul. 1998, 271-273.

Ratkalkar, et al., "Mechanisms of Stone Formation", Clin Rev Bone Miner Metab. 9(3-4), 2011, 187-197.

Schetter , et al., "Nucleoporins NPP-1, NPP-3, NPP-4, NPP-11 and NPP-13 are required for proper spindle orientation in C. elegans", Dev Biol. 289(2), Jan. 15, 2006, 360-371.

Shankar , et al., "Progeria—A Brief Review", International Journal of Pharma and Bio Sciences 2, 2010, 1-14.

Zhang , et al., "The interaction of cationic polymers and their bisphosphonate derivatives with hydroxyapatite", Macromol Biosci. 7(5), May 10, 2007, 656-670 (Abstract Only).

Sheehan , et al., "Genetic modifiers of sickle cell anemia in the Baby Hug cohort: influence on laboratory and clinical phenotypes", Am J Hematol. 88(7), 2013, 571-576.

Silcox , et al., "Measurement of inorganic pyrophosphate in biological fluids. Elevated levels in some patients with osteoarthritis, pseudogout, acromegaly, and uremia", J Clin Invest. 52(8), Aug. 1973, 1863-1870.

Stefan , et al., "NPP-type ectophosphodiesterases: unity in diversity. ", Trends Biochem Sci. 30(10), Oct. 2005, 542-550.

Terkeltaub , "Physiologic and pathologic functions of the NPP nucleotide pyrophosphatase/phosphodiesterase family focusing on NPP1 in calcification.", Purinergic Signal. 2(2), Jun. 2, 2006, 371-377.

Tsai , et al., "The Ectoenzyme E-NPP3 Negatively Regulates AT••-Dependent Chronic Allergic Responses by Basophils and Mast Cells", Immunity 42, Feb. 2015, 279-293.

Van Meeteren , et al., "Inhibition of autotaxin by lysophosphatidic acid and sphingosine 1-phosphate", J Biol Chem. 280(22), Jun. 2005, 21155-21161.

Whisstock , et al., "Prediction of proteinfunction fromprotein sequence and structure", Quarterly Reviews of Biophysics 36, 3 (2003), pp. 2003, 307-340.

Witkowski , et al., "Conversion of a Beta-Ketoacyl Synthase to a Malonyl Decarboxylase by Replacement of the Active-Site Cysteine With Glutamine", Biochemistry 38(36), Sep. 1999, 11643-11650.

Sayer "Progress in understanding the genetics of calcium-containing nephrolithiasis." Journal of the American Society of Nephrology 28.3 (2017): 748-759.

Robbie, et al. "A novel investigational Fc-modified humanized monoclonal antibody, motavizumab-YTE, has an extended half-life in healthy adults." Antimicrobial agents and chemotherapy 57.12 (2013): 6147-6153.

International Search Report and Written Opinion for PCT International Application No. PCT/US2019/049243 issued Jan. 21, 2020.

PCT International Search Report and Written Opinion for PCT International Application No. PCT/US2019/031049 issued May 7, 2019.

Gao, et al. "Engineering hybrid nanotube wires for high-power biofuel cells." Nature communications 1.1 (2010): 2.

Nitschke, et al. "ENPP1-Fc prevents neointima formation in generalized arterial calcification of infancy through the generation of AMP." Experimental & Molecular Medicine 50.10 (2018): 1-12.

iii iv

| 4 hr | 7 hr | 18 hr | 25.5 hr | 48 hr | 75 hr | 91 hr |
|---|---|---|---|---|---|---|
| 348 | 1,072 | 1,912 | 1,512 | 1,552 | 892 | 668 |
| 416 | 536 | 1,476 | 1,244 | 1,104 | 844 | 908 |
| | 492 | 1,628 | 1,488 | | 904 | 692 |
| | | 1,280 | 1,312 | | 932 | 640 |
| | | 1,716 | 1,172 | | 788 | |

Hours

| | AUC | PK | Signal seq | Catalytic | Endonuclease | Linker |
|---|---|---|---|---|---|---|
| CC07 | 3027 | 34.2 | | | | |
| 1024 | 4537 | 34.9 | C25N K27T | | S766N | |
| 930 | 2545 | 35.4 | | K369N / I371T | | |
| 930 (ST) | 4407 | 36.3 | | K369N / I371T | | |
| 976 | 3636 | 36.4 | C25N K27T | | | |
| 770B | 3647 | 36.4 | | | | |
| 1020 | 12829 | 37 | C25N K27T | | | E864N L866T |
| 1047 | 4373 | 37.6 | V29N | | | E864N L866T |
| 951 | 1789 | 40 | | | E592N | |
| 951 (ST) | 8379 | 49.3 | | | E592N | |
| 922 | 23393 | 61.8 | | I256T | | |

| | AUC | PK | Signal seq | Catalytic | Endonuclease | Typsin KO | FcRn |
|---|---|---|---|---|---|---|---|
| 1064 | 7540 | 50.6 | C25N K27T | | S766N | | H1064K N1065F |
| 1048 | 13918 | 57.1 | V29N | | | | H1064K N1065F |
| 1051 | 13812 | 63.4 | V29N | | | | H1064K N1065F |
| 1057 | 5826 | 64.6 | V29N | | S766N | | H1064K N1065F |
| 1064 (ST) | 20062 | 70.1 | C25N K27T | | S766N | | H1064K N1065F |
| 1089 | 19835 | 76.4 | V29N | | E592N | R741D | H1064K N1065F |
| 1057 (ST) | 15337 | 87.4 | V29N | | S766N | | H1064K N1065F |
| 1014 (ST) | 13883 | 96.2 | V29N | | E592N | | H1064K N1065F |
| 1014 | 21752 | 99.9 | V29N | | E592N | | H1064K N1065F |
| 1057 (ST)A | 23867 | 124.9 | V29N | | S766N | | H1064K N1065F |

| | AUC | PK | Signal seq | Catalytic | Endonuclease | FcRn |
|---|---|---|---|---|---|---|
| 1030 | 1912 | 45.4 | | | S766N | M883Y S885T T887E |
| 1082 | 14978 | 70 | V29N | | E592N | M883Y S885T T887E |
| 1028 | 16932 | 80.1 | | | E592N | M883Y S885T T887E |
| 981 | 17587 | 84 | | | | M883Y S885T T887E |
| 1028 (ST) | 25500 | 100 | | | E592N | M883Y S885T T887E |
| 1040 | 32391 | 119.4 | V29N | | P534N V536T | M883Y S885T T887E |
| 981 (ST) | 30021 | 122.5 | | | | M883Y S885T T887E |
| 1101 | 35021 | 126.3 | V29N | I256T | P534N V536T | M883Y S885T T887E |
| 1101 (ST) | 37239 | 152.9 | V29N | I256T | P534N V536T | M883Y S885T T887E |

| | AUC IV | AUC SC | % Bioavailable |
|---|---|---|---|
| 1101 ST | 32349 | 22439 | 69.4 |
| 1057 ST-A | 21276 | 10115 | 47.5 |
| 1057 ST | 17211 | 6325 | 36.7 |
| 1057 | 11520 | 4097 | 35.6 |
| 941 | 10721 | 2604 | 24.3 |

| Construct | Mutations | | | | | Sialyl Transferase | PK | Area Under Curve (AUC) |
|---|---|---|---|---|---|---|---|---|
| | Signal Sequence | Catalytic Domain | Nuclease Domain | Linker 2 | Fc Domain | | | |
| 770 | | | | | | | 34.2 | 3,027 |
| 922 | | | | | | | 61.8 | 23393 |
| 930 | | K369N I317T | | | | | 35.4 | 2,545 |
| 951 | | | E592N | | | | 40 | 1,789 |
| 976 | C25N K27T | | | | | | 36.4 | 3,636 |
| 981 | | | | | M883Y S885T T887E | | 84 | 17,587 |
| 1014 | V29N | | E592N | | H1064K N1065F | | 99.9 | 21,752 |
| 1020 | C25N K27T | | | E864N L866T | | | 37 | 12,829 |
| 1024 | C25N K27T | | S766N | | | | 34.9 | 4,537 |
| 1028 | | | E592N | | M883Y S885T T887E | | 80.1 | 16,932 |
| 1030 | | | S766N | | M883Y S885T T887E | | 45.4 | 1,912 |
| 1040 | V29N | | P534N V536T | | M883Y S885T T887E | | 119.4 | 32,391 |
| 1047 | V29N | | | E864N L866T | | | 37.6 | 4,373 |
| 1048 | V29N | | | | H1064K N1065F | | 57.1 | 13,918 |
| 1051 | V29N | | | | H1064K N1065F | | 63.4 | 13,812 |

| Construct | Mutations | | | | | Sialyl Transferase | PK | Area Under Curve (AUC) |
|---|---|---|---|---|---|---|---|---|
| | Signal Sequenc | Catalytic Domain | Nuclease Domain | Linker 2 | Fc Domain | | | |
| 1057 | V29N | | S766N | | H1064K N1065F | | 64.6 | 5,826 |
| 1064 | C25N K27T | | S766N | | H1064K N1065F | | 50.6 | 7,540 |
| 1082 | V29N | | E592N | | M883Y S885T T887E | | 70 | 14,978 |
| 1101 | V29N | I256T | P534N V536T | | H1064K N1065F | | 126.3 | 35,021 |
| 1014-ST | V29N | | E592N | | H1064K N1065F | Y | 96.2 | 13,883 |
| 1028-ST | | | E592N | | M883Y S885T T887E | Y | 100 | 25,500 |
| 1057-ST | V29N | | S766N | | H1064K N1065F | Y | 87.4 | 15,337 |
| 1057-ST-A | V29N | | S766N | | H1064K N1065F | Y | 124.9 | 23,867 |
| 1064-ST | C25N K27T | | S766N | | H1064K N1065F | Y | 70.1 | 20,062 |
| 1089 (trypsin KO) | V29N | | E592N R741D | | H1064K N1065F | | 76.4 | 19,835 |
| 1101-ST | V29N | I256T | P534N V536T | | M883Y S885T T887E | Y | 152.9 | 35,021 |
| 770B | | | | | | | 36.4 | 3,647 |
| 930-ST | | K369N I317T | | | | Y | 36.3 | 4,407 |
| 951-ST | | | E592N | | | Y | 49.3 | 8,379 |
| 981-ST | | | | | M883Y S885T T887E | Y | 122.5 | 30,021 |

Area Under Curve Sorted by Signal Sequence Mutations

Area Under Curve Sorted by Nuclease Mutations

SEQUENCE LISTING

```
Sequence total quantity: 18
SEQ ID NO: 1           moltype = AA  length = 925
FEATURE                Location/Qualifiers
source                 1..925
                       mol_type = protein
                       organism = Homo sapiens
SEQUENCE: 1
MERDGCAGGG SRGGEGGRAP REGPAGNGRD RGRSHAAEAP GDPQAAASLL APMDVGEEPL  60
EKAARARTAK DPNTYKVLSL VLSVCVLTTI LGCIFGLKPS CAKEVKSCKG RCFERTFGNC  120
RCDAACVELG NCCLDYQETC IEPEHIWTCN KFRCGEKRLT RSLCACSDDC KDKGDCCINY  180
SSVCQGEKSW VEEPCESINE PQCPAGFETP PTLLFSLDGF RAEYLHTWGG LLPVISKLKK  240
CGTYTKNMRP VYPTKTFPNH YSIVTGLYPE SHGIIDNKMY DPKMNASFSL KSKEKFNPEW  300
YKGEPIWVTA KYQGLKSGTF FWPGSDVEIN GIFPDIYKMY NGSVPFEERI LAVLQWLQLP  360
KDERPHFYTL YLEEPDSSGH SYGPVSSEVI KALQRVDGMV GMLMDGLKEL NLHRCLNLIL  420
ISDHGMEQGS CKKYIYLNKY LGDVKNIKVI YGPAARLRPS DVPDKYYSFN YEGIARNLSC  480
REPNQHFKPY LKHFLPKRLH FAKSDRIEPL TFYLDPQWQL ALNPSERKYC GSGFHGSDNV  540
FSNMQALFVG YGPGFKHGIE ADTFENIEVY NLMCDLLNLT PAPNNGTHGS LNHLLKNPVY  600
TPKHPKEVHP LVQCPFTRNP RDNLGCSCNP SILPIEDFQT QFNLTVAEEK IIKHETLPYG  660
RPRVLQKENT ICLLSQHQFM SGYSQDILMP LWTSYTVDRN DSFSTEDFSN CLYQDFRIPL  720
SPVHKCSFYK NNTKVSYGFL SPPQLNKNSS GIYSEALLTT NIVPMYQSFQ VIWRYFHDTL  780
LRKYAEERNG VNVVSGPVFD FDYDGRCDSL ENLRQKRRVI RNQEILIPTH FFIVLTSCKD  840
TSQTPLHCEN LDTLAFILPH RTDNSESCVH GKHDSSWVEE LLMLHRARIT DVEHITGLSF  900
YQQRKEPVSD ILKLKTHLPT FSQED                                     925

SEQ ID NO: 2           moltype = AA  length = 888
FEATURE                Location/Qualifiers
source                 1..888
                       mol_type = protein
                       organism = Homo sapiens
SEQUENCE: 2
MARRSSFQSC QIISLFTFAV GVNICLGFTA HRIKRAEGWE EGPPTVLSDS PWTNISGSCK  60
GRCFELQEAG PPDCRCDNLC KSYTSCCHDF DELCLKTARG WECTKDRCGE VRNEENACHC  120
SEDCLARGDC CTNYQVVCKG ESHWVDDDCE EIKAAECPAG FVRPPLIIFS VDGFRASYMK  180
KGSKVMPNIE KLRSCGTHSP YMRPVYPTKT FPNLYTLATG LYPESHGIVG NSMYDPVFDA  240
TFHLRGREKF NHRWWGGQPL WITATKQGVK AGTFFWSVVI PHERRILTIL QWLTLPDHER  300
PSVYAFYSEQ PDFSGHKYGP FGPEMTNPLR EIDKIVGQLM DGLKQLKLHR CVNVIFVGDH  360
GMEDVTCDRT EFLSNYLTNV DDITLVPGTL GRIRSKFSNN AKYDPKAIIA NLTCKKPDQH  420
FKPYLKQHLP KRLHYANNRR IEDIHLLVER RWHVARKPLD VYKKPSGKCF FQGDHGFDNK  480
VNSMQTVFVG YGSTFKYKTK VPPFENIELY NVMCDLLGLK PAPNNGTHGS LNHLLRTNTF  540
RPTMPEEVTR PNYPGIMYLQ SDFDLGCTCD DKVEPKNKLD ELNKRLHTKG STEAETRKFR  600
GSRNENKENI NGNFEPRKER HLLYGRPAVL YRTRYDILYH TDFESGYSEI FLMPLWTSYT  660
VSKQAEVSSV PDHLTSCVRP DVRVSPSFSQ NCLAYKNDKQ MSYGFLFPPY LSSSPEAKYD  720
AFLVTNMVPM YPAFKRVWNY FQRVLVKKYA SERNGVNVIS GPIFDYDYDG LHDTEDKIKQ  780
YVEGSSIPVP THYYSIITSC LDFTQPADKC DGPLSVSSFI LPHRPDNEES CNSSEDESKW  840
VEELMKMHTA RVRDIEHLTS LDFFRKTSRS YPEILTLKTY LHTYESEI             888

SEQ ID NO: 3           moltype = AA  length = 227
FEATURE                Location/Qualifiers
source                 1..227
                       mol_type = protein
                       organism = Homo sapiens
SEQUENCE: 3
DKTHTCPPCP APELLGGPSV FLFPPKPKDT LMISRTPEVT CVVVDVSHED PEVKFNWYVD  60
GVEVHNAKTK PREEQYNSTY RVVSVLTVLH QDWLNGKEYK CKVSNKALPA PIEKTISKAK  120
GQPREPQVYT LPPSREEMTK NQVSLTCLVK GFYPSDIAVE WESNGQPENN YKTTPPVLDS  180
DGSFFLYSKL TVDKSRWQQG NVFSCSVMHE ALHNHYTQKS LSLSPGK              227

SEQ ID NO: 4           moltype = AA  length = 24
FEATURE                Location/Qualifiers
VAR_SEQ                23
                       note = Xaa23 is absent or Leu
VAR_SEQ                24
                       note = Xaa24 is absent if Xaa23 is absent, and Xaa24 is
                        absent or Gln if Xaa23 is Leu
source                 1..24
                       mol_type = protein
                       organism = Homo sapiens
SEQUENCE: 4
MTSKFLLVSF ILAALSLSTT FSXX                                      24

SEQ ID NO: 5           moltype = AA  length = 22
FEATURE                Location/Qualifiers
source                 1..22
                       mol_type = protein
                       organism = Homo sapiens
SEQUENCE: 5
MRGPAVLLTV ALATLLAPGA GA                                        22
```

-continued

SEQ ID NO: 6 moltype = AA length = 20
FEATURE Location/Qualifiers
source 1..20
mol_type = protein
organism = Homo sapiens
SEQUENCE: 6
MRGPAVLLTV ALATLLAPGA 20

SEQ ID NO: 7 moltype = AA length = 1078
FEATURE Location/Qualifiers
REGION 1..1078
note = Recombinantly synthesized
source 1..1078
mol_type = protein
organism = synthetic construct
SEQUENCE: 7
MRGPAVLLTV ALATLLAPGA GAPSCAKEVK SCKGRCFERT FGNCRCDAAC VELGNCCLDY 60
QETCIEPEHI WTCNKFRCGE KRLTRSLCAC SDDCKDKGDC CINYSSVCQG EKSWVEEPCE 120
SINEPQCPAG FETPPTLLFS LDGFRAEYLH TWGGLLPVIS KLKKCGTYTK NMRPVYPTKT 180
FPNHYSIVTG LYPESHGIID NKMYDPKMNA SFSLKSKEKF NPEWYKGEPI WVTAKYQGLK 240
SGTFFWPGSD VEINGIFPDI YKMYNGSVPF EERILAVLQW LQLPKDERPH FYTLYLEEPD 300
SSGHSYGPVS SEVIKALQRV DGMVGMLMDG LKELNLHRCL NLILISDHGM EQGSCKKYIY 360
LNKYLGDVKN IKVIYGPAAR LRPSDVPDKY YSFNYEGIAR NLSCREPNQH FKPYLKHFLP 420
KRLHFAKSDR IEPLTFYLDP QWQLALNPSE RKYCGSGFHG SDNVFSNMQA LFVGYGPGFK 480
HGIEADTFEN IEVYNLMCDL LNLTPAPNNG THGSLNHLLK NPVYTPKHPK EVHPLVQCPF 540
TRNPRDNLGC SCNPSILPIE DFQTQFNLTV AEEKIIKHET LPYGRPRVLQ KENTICLLSQ 600
HQFMSGYSQD ILMPLWTSYT VDRNDSFSTE DFSNCLYQDF RIPLSPVHKC SFYKNNTKVS 660
YGFLSPPQLN KNSSGIYSEA LLTTNIVPMY QSFQVIWRYF HDTLLRKYAE ERNGVNVVSG 720
PVFDFDYDGR CDSLENLRQK RRVIRNQEIL IPTHFFIVLT SCKDTSQTPL HCENLDTLAF 780
ILPHRTDNSE SCVHGKHDSS WVEELLMLHR ARITDVEHIT GLSFYQQRKE PVSDILKLKT 840
HLPTFSQEDR SDKTHTCPPC PAPELLGGPS VFLFPPKPKD TLMISRTPEV TCVVVDVSHE 900
DPEVKFNWYV DGVEVHNAKT KPREEQYNST YRVVSVLTVL HQDWLNGKEY KCKVSNKALP 960
APIEKTISKA KGQPREPQVY TLPPSREEMT KNQVSLTCLV KGFYPSDIAV EWESNGQPEN 1020
NYKTTPPVLD SDGSFFLYSK LTVDKSRWQQ GNVFSCSVMH EALHNHYTQK SLSLSPGK 1078

SEQ ID NO: 8 moltype = length =
SEQUENCE: 8
000

SEQ ID NO: 9 moltype = AA length = 5
FEATURE Location/Qualifiers
REGION 1..5
note = Linker
source 1..5
mol_type = protein
organism = synthetic construct
SEQUENCE: 9
GGGGS 5

SEQ ID NO: 10 moltype = AA length = 827
FEATURE Location/Qualifiers
REGION 1..827
note = Recombinantly synthesized
source 1..827
mol_type = protein
organism = synthetic construct
SEQUENCE: 10
PSCAKEVKSC KGRCFERTFG NCRCDAACVE LGNCCLDYQE TCIEPEHIWT CNKFRCGEKR 60
LTRSLCACSD DCKDKGDCCI NYSSVCQGEK SWVEEPCESI NEPQCPAGFE TPPTLLFSLD 120
GFRAEYLHTW GGLLPVISKL KKCGTYTKNM RPVYPTKTFP NHYSIVTGLY PESHGIIDNK 180
MYDPKMNASF SLKSKEKFNP EWYKGEPIWV TAKYQGLKSG TFFWPGSDVE INGIFPDIYK 240
MYNGSVPFEE RILAVLQWLQ LPKDERPHFY TLYLEEPDSS GHSYGPVSSE VIKALQRVDG 300
MVGMLMDGLK ELNLHRCLNL ILISDHGMEQ GSCKKYIYLN KYLGDVKNIK VIYGPAARLR 360
PSDVPDKYYS FNYEGIARNL SCREPNQHFK PYLKHFLPKR LHFAKSDRIE PLTFYLDPQW 420
QLALNPSERK YCGSGFHGSD NVFSNMQALF VGYGPGFKHG IEADTFENIE VYNLMCDLLN 480
LTPAPNNGTH GSLNHLLKNP VYTPKHPKEV HPLVQCPFTR NPRDNLGCSC NPSILPIEDF 540
QTQFNLTVAE EKIIKHETLP YGRPRVLQKE NTICLLSQHQ FMSGYSQDIL MPLWTSYTVD 600
RNDSFSTEDF SNCLYQDFRI PLSPVHKCSF YKNNTKVSYG FLSPPQLNKN SSGIYSEALL 660
TTNIVPMYQS FQVIWRYFHD TLLRKYAEER NGVNVVSGPV FDFDYDGRCD SLENLRQKRR 720
VIRNQEILIP THFFIVLTSC KDTSQTPLHC ENLDTLAFIL PHRTDNSESC VHGKHDSSWV 780
EELLMLHRAR ITDVEHITGL SFYQQRKEPV SDILKLKTHL PTFSQED 827

SEQ ID NO: 11 moltype = AA length = 827
FEATURE Location/Qualifiers
REGION 1..827
note = Recombinantly synthesized
source 1..827
mol_type = protein
organism = synthetic construct

```
SEQUENCE: 11
PSCAKEVKSC KGRCFERTFG NCRCDAACVE LGNCCLDYQE TCIEPEHIWT CNKFRCGEKR  60
LTRSLCACSD DCKDKGDCCI NYSSVCQGEK SWVEEPCESI NEPQCPAGFE TPPTLLFSLD  120
GFRAEYLHTW GGLLPVISKL KKCGTYTKNM RPVYPTKTFP NHYSIVTGLY PESHGIIDNK  180
MYDPKMNASF SLKSKEKFNP EWYKGEPIWV TAKYQGLKSG TFFWPGSDVE INGTFPDIYK  240
MYNGSVPFEE RILAVLQWLQ LPKDERPHFY TLYLEEPDSS GHSYGPVSSE VIKALQRVDG  300
MVGMLMDGLK ELNLHRCLNL ILISDHGMEQ GSCKKYIYLN KYLGDVKNIK VIYGPAARLR  360
PSDVPDKYYS FNYEGIARNL SCREPNQHFK PYLKHFLPKR LHFAKSDRIE PLTFYLDPQW  420
QLALNPSERK YCGSGFHGSD NVFSNMQALF VGYGPGFKHG IEADTFENIE VYNLMCDLLN  480
LTPAPNNGTH GSLNHLLKNP VYTPKHPKEV HPLVQCPFTR NPRDNLGCSC NPSILPIEDF  540
QTQFNLTVAE EKIIKHETLP YGRPRVLQKE NTICLLSQHQ FMSGYSQDIL MPLWTSYTVD  600
RNDSFSTEDF SNCLYQDFRI PLSPVHKCSF YKNNTKVSYG FLSPPQLNKN SSGIYSEALL  660
TTNIVPMYQS FQVIWRYFHD TLLRKYAEER NGVNVVSGPV FDFDYDGRCD SLENLRQKRR  720
VIRNQEILIP THFFIVLTSC KDTSQTPLHC ENLDTLAFIL PHRTDNSESC VHGKHDSSWV  780
EELLMLHRAR ITDVEHITGL SFYQQRKEPV SDILKLKTHL PTFSQED                827

SEQ ID NO: 12          moltype = AA  length = 827
FEATURE                Location/Qualifiers
REGION                 1..827
                       note = Recombinantly synthesized
source                 1..827
                       mol_type = protein
                       organism = synthetic construct
SEQUENCE: 12
PSCAKENKSC KGRCFERTFG NCRCDAACVE LGNCCLDYQE TCIEPEHIWT CNKFRCGEKR  60
LTRSLCACSD DCKDKGDCCI NYSSVCQGEK SWVEEPCESI NEPQCPAGFE TPPTLLFSLD  120
GFRAEYLHTW GGLLPVISKL KKCGTYTKNM RPVYPTKTFP NHYSIVTGLY PESHGIIDNK  180
MYDPKMNASF SLKSKEKFNP EWYKGEPIWV TAKYQGLKSG TFFWPGSDVE INGTFPDIYK  240
MYNGSVPFEE RILAVLQWLQ LPKDERPHFY TLYLEEPDSS GHSYGPVSSE VIKALQRVDG  300
MVGMLMDGLK ELNLHRCLNL ILISDHGMEQ GSCKKYIYLN KYLGDVKNIK VIYGPAARLR  360
PSDVPDKYYS FNYEGIARNL SCREPNQHFK PYLKHFLPKR LHFAKSDRIE PLTFYLDPQW  420
QLALNPSERK YCGSGFHGSD NVFSNMQALF VGYGPGFKHG IEADTFENIE VYNLMCDLLN  480
LTPAPNNGTH GSLNHLLKNP VYTPKHPKEV HNLTQCPFTR NPRDNLGCSC NPSILPIEDF  540
QTQFNLTVAE EKIIKHETLP YGRPRVLQKE NTICLLSQHQ FMSGYSQDIL MPLWTSYTVD  600
RNDSFSTEDF SNCLYQDFRI PLSPVHKCSF YKNNTKVSYG FLSPPQLNKN SSGIYSEALL  660
TTNIVPMYQS FQVIWRYFHD TLLRKYAEER NGVNVVSGPV FDFDYDGRCD SLENLRQKRR  720
VIRNQEILIP THFFIVLTSC KDTSQTPLHC ENLDTLAFIL PHRTDNSESC VHGKHDSSWV  780
EELLMLHRAR ITDVEHITGL SFYQQRKEPV SDILKLKTHL PTFSQED                827

SEQ ID NO: 13          moltype = AA  length = 227
FEATURE                Location/Qualifiers
source                 1..227
                       mol_type = protein
                       organism = Homo sapiens
SEQUENCE: 13
DKTHTCPPCP APELLGGPSV FLFPPKPKDT LMISRTPEVT CVVVDVSHED PEVKFNWYVD  60
GVEVHNAKTK PREEQYNSTY RVVSVLTVLH QDWLNGKEYK CKVSNKALPA PIEKTISKAK  120
GQPREPQVYT LPPSREEMTK NQVSLTCLVK GFYPSDIAVE WESNGQPENN YKTTPPVLDS  180
DGSFFLYSKL TVDKSRWQQG NVFSCSVMHE ALHNHYTQKS LSLSPGK                227

SEQ ID NO: 14          moltype = AA  length = 227
FEATURE                Location/Qualifiers
REGION                 1..227
                       note = Recombinantly synthesized
source                 1..227
                       mol_type = protein
                       organism = synthetic construct
SEQUENCE: 14
DKTHTCPPCP APELLGGPSV FLFPPKPKDT LYITREPEVT CVVVDVSHED PEVKFNWYVD  60
GVEVHNAKTK PREEQYNSTY RVVSVLTVLH QDWLNGKEYK CKVSNKALPA PIEKTISKAK  120
GQPREPQVYT LPPSREEMTK NQVSLTCLVK GFYPSDIAVE WESNGQPENN YKTTPPVLDS  180
DGSFFLYSKL TVDKSRWQQG NVFSCSVMHE ALHNHYTQKS LSLSPGK                227

SEQ ID NO: 15          moltype = AA  length = 1059
FEATURE                Location/Qualifiers
REGION                 1..1059
                       note = Recombinantly synthesized
source                 1..1059
                       mol_type = protein
                       organism = synthetic construct
SEQUENCE: 15
PSCAKEVKSC KGRCFERTFG NCRCDAACVE LGNCCLDYQE TCIEPEHIWT CNKFRCGEKR  60
LTRSLCACSD DCKDKGDCCI NYSSVCQGEK SWVEEPCESI NEPQCPAGFE TPPTLLFSLD  120
GFRAEYLHTW GGLLPVISKL KKCGTYTKNM RPVYPTKTFP NHYSIVTGLY PESHGIIDNK  180
MYDPKMNASF SLKSKEKFNP EWYKGEPIWV TAKYQGLKSG TFFWPGSDVE INGIFPDIYK  240
MYNGSVPFEE RILAVLQWLQ LPKDERPHFY TLYLEEPDSS GHSYGPVSSE VIKALQRVDG  300
MVGMLMDGLK ELNLHRCLNL ILISDHGMEQ GSCKKYIYLN KYLGDVKNIK VIYGPAARLR  360
PSDVPDKYYS FNYEGIARNL SCREPNQHFK PYLKHFLPKR LHFAKSDRIE PLTFYLDPQW  420
QLALNPSERK YCGSGFHGSD NVFSNMQALF VGYGPGFKHG IEADTFENIE VYNLMCDLLN  480
```

```
LTPAPNNGTH GSLNHLLKNP VYTPKHPKEV HPLVQCPFTR NPRDNLGCSC NPSILPIEDF  540
QTQFNLTVAE EKIIKHETLP YGRPRVLQKE NTICLLSQHQ FMSGYSQDIL MPLWTSYTVD  600
RNDSFSTEDF SNCLYQDFRI PLSPVHKCSF YKNNTKVSYG FLSPPQLNKN SSGIYSEALL  660
TTNIVPMYQS FQVIWRYFHD TLLRKYAEER NGVNVVSGPV FDFDYDGRCD SLENLRQKRR  720
VIRNQEILIP THFFIVLTSC KDTSQTPLHC ENLDTLAFIL PHRTDNSESC VHGKHDSSWV  780
EELLMLHRAR ITDVEHITGL SFYQQRKEPV SDILKLKTHL PTFSQEDGGG GSDKTHTCPP  840
CPAPELLGGP SVFLFPPKPK DTLYITREPE VTCVVVDVSH EDPEVKFNWY VDGVEVHNAK  900
TKPREEQYNS TYRVVSVLTV LHQDWLNGKE YKCKVSNKAL PAPIEKTISK AKGQPREPQV  960
YTLPPSREEM TKNQVSLTCL VKGFYPSDIA VEWESNGQPE NNYKTTPPVL DSDGSFFLYS  1020
KLTVDKSRWQ QGNVFSCSVM HEALHNHYTQ KSLSLSPGK                        1059

SEQ ID NO: 16          moltype = AA  length = 1057
FEATURE                Location/Qualifiers
REGION                 1..1057
                       note = Recombinantly synthesized
source                 1..1057
                       mol_type = protein
                       organism = synthetic construct
SEQUENCE: 16
PSCAKEVKSC KGRCFERTFG NCRCDAACVE LGNCCLDYQE TCIEPEHIWT CNKFRCGEKR  60
LTRSLCACSD DCKDKGDCCI NYSSVCQGEK SWVEEPCESI NEPQCPAGFE TPPTLLFSLD  120
GFRAEYLHTW GGLLPVISKL KKCGTYTKNM RPVYPTKTFP NHYSIVTGLY PESHGIIDNK  180
MYDPKMNASF SLKSKEKFNP EWYKGEPIWV TAKYQGLKSG TFFWPGSDVE INGIFPDIYK  240
MYNGSVPFEE RILAVLQWLQ LPKDERPHFY TLYLEEPDSS GHSYGPVSSE VIKALQRVDG  300
MVGMLMDGLK ELNLHRCLNL ILISDHGMEQ GSCKKYIYLN KYLGDVKNIK VIYGPAARLR  360
PSDVPDKYYS FNYEGIARNL SCREPNQHFK PYLKHFLPKR LHFAKSDRIE PLTFYLDPQW  420
QLALNPSERK YCGSGFHGSD NVFSNMQALF VGYGPGFKHG IEADTFENIE VYNLMCDLLN  480
LTPAPNNGTH GSLNHLLKNP VYTPKHPKEV HPLVQCPFTR NPRDNLGCSC NPSILPIEDF  540
QTQFNLTVAE EKIIKHETLP YGRPRVLQKE NTICLLSQHQ FMSGYSQDIL MPLWTSYTVD  600
RNDSFSTEDF SNCLYQDFRI PLSPVHKCSF YKNNTKVSYG FLSPPQLNKN SSGIYSEALL  660
TTNIVPMYQS FQVIWRYFHD TLLRKYAEER NGVNVVSGPV FDFDYDGRCD SLENLRQKRR  720
VIRNQEILIP THFFIVLTSC KDTSQTPLHC ENLDTLAFIL PHRTDNSESC VHGKHDSSWV  780
EELLMLHRAR ITDVEHITGL SFYQQRKEPV SDILKLKTHL PTFSQEDLIN DKTHTCPPCP  840
APELLGGPSV FLFPPKPKDT LYITREPEVT CVVVDVSHED PEVKFNWYVD GVEVHNAKTK  900
PREEQYNSTY RVVSVLTVLH QDWLNGKEYK CKVSNKALPA PIEKTISKAK GQPREPQVYT  960
LPPSREEMTK NQVSLTCLVK GFYPSDIAVE WESNGQPENN YKTTPPVLDS DGSFFLYSKL  1020
TVDKSRWQQG NVFSCSVMHE ALHNHYTQKS LSLSPGK                          1057

SEQ ID NO: 17          moltype = AA  length = 1057
FEATURE                Location/Qualifiers
REGION                 1..1057
                       note = Recombinantly synthesized
source                 1..1057
                       mol_type = protein
                       organism = synthetic construct
SEQUENCE: 17
PSCAKEVKSC KGRCFERTFG NCRCDAACVE LGNCCLDYQE TCIEPEHIWT CNKFRCGEKR  60
LTRSLCACSD DCKDKGDCCI NYSSVCQGEK SWVEEPCESI NEPQCPAGFE TPPTLLFSLD  120
GFRAEYLHTW GGLLPVISKL KKCGTYTKNM RPVYPTKTFP NHYSIVTGLY PESHGIIDNK  180
MYDPKMNASF SLKSKEKFNP EWYKGEPIWV TAKYQGLKSG TFFWPGSDVE INGTFPDIYK  240
MYNGSVPFEE RILAVLQWLQ LPKDERPHFY TLYLEEPDSS GHSYGPVSSE VIKALQRVDG  300
MVGMLMDGLK ELNLHRCLNL ILISDHGMEQ GSCKKYIYLN KYLGDVKNIK VIYGPAARLR  360
PSDVPDKYYS FNYEGIARNL SCREPNQHFK PYLKHFLPKR LHFAKSDRIE PLTFYLDPQW  420
QLALNPSERK YCGSGFHGSD NVFSNMQALF VGYGPGFKHG IEADTFENIE VYNLMCDLLN  480
LTPAPNNGTH GSLNHLLKNP VYTPKHPKEV HPLVQCPFTR NPRDNLGCSC NPSILPIEDF  540
QTQFNLTVAE EKIIKHETLP YGRPRVLQKE NTICLLSQHQ FMSGYSQDIL MPLWTSYTVD  600
RNDSFSTEDF SNCLYQDFRI PLSPVHKCSF YKNNTKVSYG FLSPPQLNKN SSGIYSEALL  660
TTNIVPMYQS FQVIWRYFHD TLLRKYAEER NGVNVVSGPV FDFDYDGRCD SLENLRQKRR  720
VIRNQEILIP THFFIVLTSC KDTSQTPLHC ENLDTLAFIL PHRTDNSESC VHGKHDSSWV  780
EELLMLHRAR ITDVEHITGL SFYQQRKEPV SDILKLKTHL PTFSQEDLIN DKTHTCPPCP  840
APELLGGPSV FLFPPKPKDT LYITREPEVT CVVVDVSHED PEVKFNWYVD GVEVHNAKTK  900
PREEQYNSTY RVVSVLTVLH QDWLNGKEYK CKVSNKALPA PIEKTISKAK GQPREPQVYT  960
LPPSREEMTK NQVSLTCLVK GFYPSDIAVE WESNGQPENN YKTTPPVLDS DGSFFLYSKL  1020
TVDKSRWQQG NVFSCSVMHE ALHNHYTQKS LSLSPGK                          1057

SEQ ID NO: 18          moltype = AA  length = 1059
FEATURE                Location/Qualifiers
REGION                 1..1059
                       note = Recombinantly synthesized
source                 1..1059
                       mol_type = protein
                       organism = synthetic construct
SEQUENCE: 18
PSCAKEVKSC KGRCFERTFG NCRCDAACVE LGNCCLDYQE TCIEPEHIWT CNKFRCGEKR  60
LTRSLCACSD DCKDKGDCCI NYSSVCQGEK SWVEEPCESI NEPQCPAGFE TPPTLLFSLD  120
GFRAEYLHTW GGLLPVISKL KKCGTYTKNM RPVYPTKTFP NHYSIVTGLY PESHGIIDNK  180
MYDPKMNASF SLKSKEKFNP EWYKGEPIWV TAKYQGLKSG TFFWPGSDVE INGTFPDIYK  240
MYNGSVPFEE RILAVLQWLQ LPKDERPHFY TLYLEEPDSS GHSYGPVSSE VIKALQRVDG  300
MVGMLMDGLK ELNLHRCLNL ILISDHGMEQ GSCKKYIYLN KYLGDVKNIK VIYGPAARLR  360
```

-continued

| | |
|---|---|
| PSDVPDKYYS FNYEGIARNL SCREPNQHFK PYLKHFLPKR LHFAKSDRIE PLTFYLDPQW | 420 |
| QLALNPSERK YCGSGFHGSD NVFSNMQALF VGYGPGFKHG IEADTFENIE VYNLMCDLLN | 480 |
| LTPAPNNGTH GSLNHLLKNP VYTPKHPKEV HPLVQCPFTR NPRDNLGCSC NPSILPIEDF | 540 |
| QTQFNLTVAE EKIIKHETLP YGRPRVLQKE NTICLLSQHQ FMSGYSQDIL MPLWTSYTVD | 600 |
| RNDSFSTEDF SNCLYQDFRI PLSPVHKCSF YKNNTKVSYG FLSPPQLNKN SSGIYSEALL | 660 |
| TTNIVPMYQS FQVIWRYFHD TLLRKYAEER NGVNVVSGPV FDFDYDGRCD SLENLRQKRR | 720 |
| VIRNQEILIP THFFIVLTSC KDTSQTPLHC ENLDTLAFIL PHRTDNSESC VHGKHDSSWV | 780 |
| EELLMLHRAR ITDVEHITGL SFYQQRKEPV SDILKLKTHL PTFSQEDGGG GSDKTHTCPP | 840 |
| CPAPELLGGP SVFLFPPKPK DTLYITREPE VTCVVVDVSH EDPEVKFNWY VDGVEVHNAK | 900 |
| TKPREEQYNS TYRVVSVLTV LHQDWLNGKE YKCKVSNKAL PAPIEKTISK AKGQPREPQV | 960 |
| YTLPPSREEM TKNQVSLTCL VKGFYPSDIA VEWESNGQPE NNYKTTPPVL DSDGSFFLYS | 1020 |
| KLTVDKSRWQ QGNVFSCSVM HEALHNHYTQ KSLSLSPGK | 1059 |

ENPP1 POLYPEPTIDES AND METHODS OF USING SAME

CROSS-REFERENCE TO RELATED APPLICATIONS

The present application is a continuation of, and claims priority to, U.S. application Ser. No. 17/601,387 filed Oct. 4, 2021, which is a 35 U.S.C. § 371 national phase application from, and claims priority to, International Application No. PCT/US2020/026643, filed Apr. 3, 2020, which claims priority under 35 U.S.C. § 119(e) to U.S. Provisional Patent Applications No. 62/830, 230 filed Apr. 5, 2019, No. 62/983,142 filed Feb. 28, 2020, and No. 62/984,650 filed Mar. 3, 2020, all of which applications are incorporated herein by reference in their entireties.

REFERENCE TO SEQUENCE LISTING

The Sequence Listing concurrently submitted herewith as a xml file named "047162-7180US3 (02366).xml" created on Apr. 4, 2025 and having a size of 30,772 bytes is herein incorporated by reference.

BACKGROUND OF THE INVENTION

The human ectonucleotide pyrophosphatase (ENPP) protein family comprises seven extracellular, glycosylated proteins (i.e., ENPP1-ENPP7) that hydrolyze phosphodiester bonds. ENPPs are cell-surface enzymes, with the exception of ENPP2, which is exported to the plasma membrane but is cleaved by furin and released into the extracellular fluid. The ENPP enzymes have high degrees of sequence and structural homology, but exhibit a diverse substrate specificity encompassing nucleotides to lipids.

ENPP1 (also known as PC-1) is a type 2 extracellular membrane-bound glycoprotein located on the mineral-depositing matrix vesicles of osteoblasts and chondrocytes, and hydrolyzes extracellular nucleotides (principally ATP) into adenosine monophosphate (AMP) and inorganic pyrophosphate (PPi). PPi functions as a potent inhibitor of ectopic tissue mineralization by binding to nascent hydroxyapatite (HA) crystals, thereby preventing the future growth of these crystals. ENPP1 generates PPi via hydrolysis of nucleotide triphosphates (NTPs), Progressive Ankylosis Protein (ANK) transports intracellular PPi into the extracellular space, and Tissue Non-specific Alkaline Phosphatase (TNAP) removes PPi via direct hydrolysis of PPi into Pi.

Ectopic tissue mineralization is associated with numerous human diseases, including chronic joint disease and acutely fatal neonatal syndromes. To prevent unwanted tissue calcification, factors that promote and inhibit tissue mineralization must be kept in tight balance. The balance of extracellular inorganic pyrophosphate (PPi) and phosphate (Pi) is an important regulator of ectopic tissue mineralization. The activity of the three extracellular enzymes—TNAP, ANK, and ENPP1—tightly control the concentration of Pi and PPi in mammals at 1-3 mM and 2-3 μM respectively. PPi is a regulator of biomineralization, inhibiting the formation of basic calcium phosphate from amorphous calcium phosphate.

ENPP1 polypeptides have been shown to be effective in treating certain diseases of ectopic tissue calcification. ENPP1-Fc has been shown to reduce generalized arterial calcifications in a mouse model for GACI (generalized arterial calcification of infants), which is a severe disease occurring in infants and involving extensive arterial calcification (Albright, et al., 2015, Nature Comm. 10006). Fusion proteins of ENPP1 have also been described to treat diseases of severe tissue calcification (PCT Application Publications Nos. WO2014/126965 and WO2016/187408), and a fusion protein of ENPP1 comprising a bone targeting domain has been described to treat GACI (PCT Application Publication No. WO/2012/125182).

There is a need in the art for polypeptides that can be used to treat certain calcification or ossification diseases in vivo. Such polypeptides should have in vivo half-lives that allow for convenient and effective dosing of the polypeptides to the subject in need thereof. The present invention fulfills this need.

BRIEF SUMMARY OF THE INVENTION

The present disclosure provides an ENPP1 polypeptide fusion comprising an ENPP1 polypeptide fused to a Fc region of an immunoglobulin, wherein the polypeptide fusion comprises at least one point mutation as described herein. The present disclosure further provides an ENPP1 mutant polypeptide comprising at least one point mutation as described elsewhere herein. The present disclosure further provides a polypeptide fusion or mutant polypeptide, either of which is expressed from a CHO cell line stably transfected with human ST6 beta-galactoside alpha-2,6-sialyltransferase (ST6GAL1). The present disclosure further provides a polypeptide fusion and/or mutant polypeptide, either of which is grown in a cell culture supplemented with sialic acid and/or N-acetylmannosamine (1,3,4-O-Bu3ManNAc).

The present disclosure further provides a method of reducing and/or preventing progression of pathological calcification in a subject in need thereof, the method comprising administering to the subject a therapeutically effective amount of the polypeptide fusion and/or the mutant polypeptide of the disclosure.

The present disclosure further provides a method of reducing and/or preventing progression of pathological ossification in a subject in need thereof, the method comprising administering to the subject a therapeutically effective amount of the polypeptide fusion and/or the mutant polypeptide of the disclosure.

The present disclosure further provides a method of reducing and/or preventing progression of ectopic calcification of soft tissue in a subject in need thereof, the method comprising administering to the subject a therapeutically effective amount of the polypeptide fusion and/or the mutant polypeptide of the disclosure.

The present disclosure further provides a method of treating, reversing, and/or preventing progression of ossification of the posterior longitudinal ligament (OPLL) in a subject in need thereof, the method comprising administering to the subject a therapeutically effective amount of the polypeptide fusion and/or the mutant polypeptide of the disclosure.

The present disclosure further provides a method of treating, reverting, and/or preventing progression of hypophosphatemic rickets in a subject in need thereof, the method comprising administering to the subject a therapeutically effective amount of the polypeptide fusion and/or the mutant polypeptide of the disclosure.

The present disclosure further provides a method of reducing and/or preventing progression of at least one disease selected from the group consisting of chronic kidney disease (CKD), end stage renal disease (ESRD), calcific uremic arteriolopathy (CUA), calciphylaxis, ossification of the posterior longitudinal ligament (OPLL), hypophosphatemic rickets, osteoarthritis, aging related hardening of arteries, idiopathic infantile arterial calcification (IIAC), Generalized Arterial Calcification of Infancy (GACI), and calcification of atherosclerotic plaques in a subject diagnosed with the at least one disease, the method comprising administering to the subject a therapeutically effective amount of the polypeptide fusion and/or the mutant polypeptide of the disclosure.

The present disclosure further provides a method of reducing and/or preventing progression of aging related hardening of arteries in a subject in need thereof the method comprising administering to the subject a therapeutically effective amount of the polypeptide fusion and/or the mutant polypeptide of the disclosure.

The present disclosure further provides a method of raising pyrophosphate (PPi) levels in a subject having PPi level lower than PPi normal level, the method comprising administering to the subject a therapeutically effective amount of the polypeptide fusion and/or the mutant polypeptide of the disclosure, whereby upon the administration the level of the PPi in the subject is elevated to a normal level of at least 2 μM and is maintained at approximately the same level.

The present disclosure further provides a method of reducing and/or preventing the progression of pathological calcification or ossification in a subject having pyrophosphate (PPi) level lower than PPi normal level, the method comprising administering to the subject a therapeutically effective amount of the polypeptide fusion and/or the mutant polypeptide of the disclosure, whereby pathological calcification or ossification in the subject is reduced and/or progression of pathological calcification or ossification in the subject is prevented.

The present disclosure further provides a method of treating ENPP1 deficiency manifested by a reduction of extracellular pyrophosphate (PPi) concentration in a subject in need thereof, the method comprising administering to the subject a therapeutically effective amount of the polypeptide fusion and/or the mutant polypeptide of the disclosure, whereby the level of the PPi in the subject is elevated.

BRIEF DESCRIPTION OF THE DRAWINGS

The following detailed description of illustrative embodiments of the disclosure will be better understood when read in conjunction with the appended drawings. For the purpose of illustrating the disclosure, exemplary embodiments are shown in the drawings. It should be understood, however, that the disclosure is not limited to the precise arrangements and instrumentalities of the embodiments shown in the drawings.

DETAILED DESCRIPTION OF THE INVENTION

Figure 1:
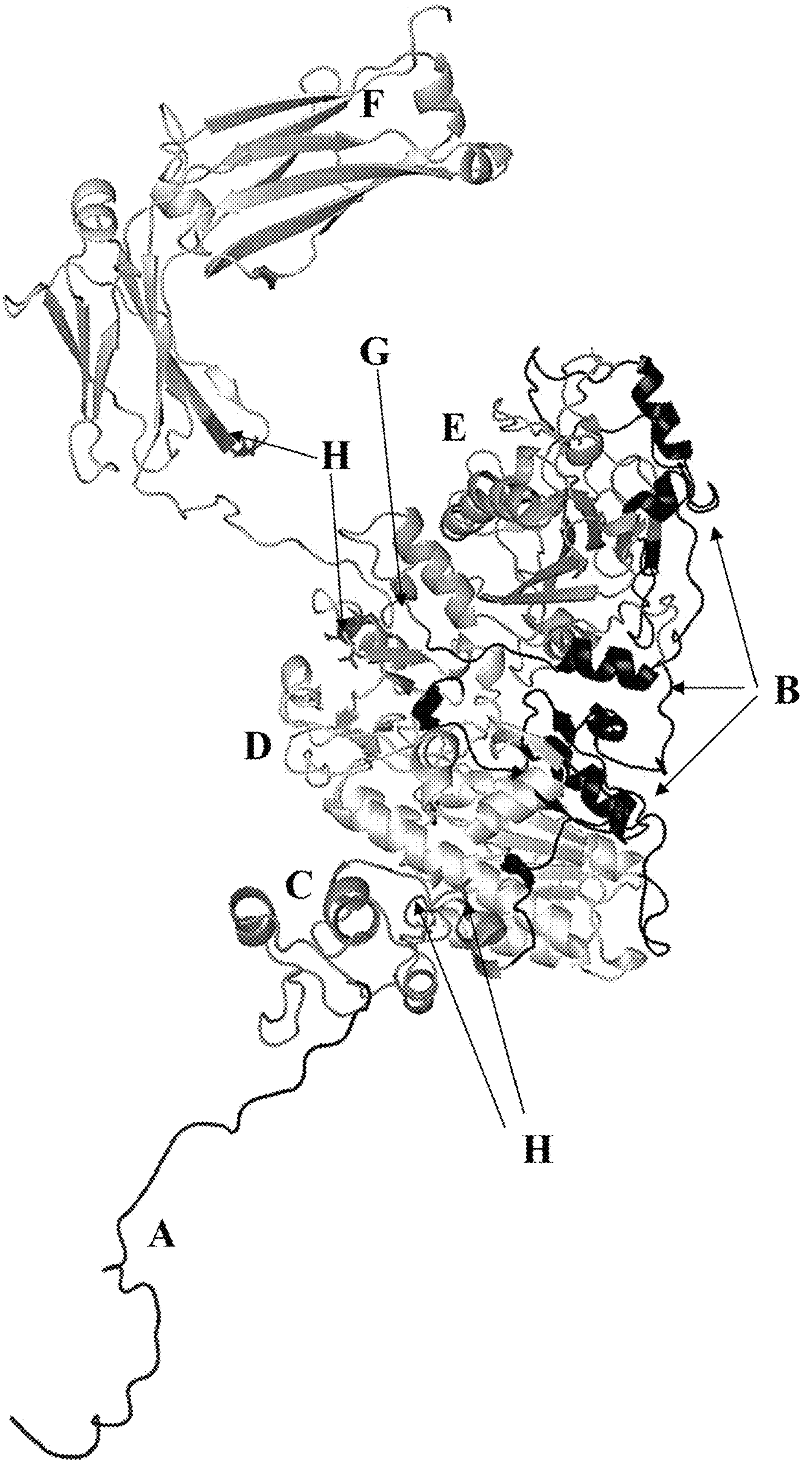
FIG. 1 illustrates an ENPP1 polypeptide contemplated within the disclosure (SEQ ID NO: 7). Point mutations are identified with reference to SEQ ID NO:7, which may also be referred to as the "parent compound," "parent polypeptide," or "Construct #770." The labelling scheme identifies the amino acid number and residue with reference to the numbering scheme illustrated in SEQ ID NO:7 followed by the amino acid that has been substituted for the residue in SEQ ID NO:7. For example, mutation C25N refers to the substitution of an asparagine (Asn or N) for a cysteine (Cys or C) at position 25 of SEQ ID NO: 7. Legend: (A)=N-terminal signal sequence from hENPP7; all regions in black (B) represent sequence from hENPP1 that do not have a formal domain definition; (C)=somatomedin B domain of hENPP1; (D)=catalytic domain of hENPP1; (E)=endonuclease domain of hENPP1; (F)=Fc domain from the Invivogen plasmid pFUSE-hIgG1-Fc; (G)=a four amino acid linker between hENPP1 and the Fc domain; (H)=known glycosylation residue.

The present disclosure relates, in one aspect, to the discovery that certain ENPP1-Fc polypeptides having improved in vivo half-lives as compared to the ENPP1-Fc polypeptides known in the art.

In one non-limiting aspect, glycosylation was promoted to shield the ENPP1-Fc polypeptides from degradation. This was achieved by introducing additional N-glycan consensus sequences onto the exterior surface of the predicted tertiary structure, guided by three-dimensional models of ENPP1.

In another non-limiting aspect, pH-dependent FcRn-mediated cellular recycling was increased by mutating the Fc domain to enhance the affinity of the fusion protein for the neonatal receptor (FcRn).

In yet another non-limiting aspect, sialyation of the fusion protein was enhanced by expressing ENPP1-Fc in CHO cell lines stably transfected with human ST6 beta-galactoside alpha-2,6-sialyltransferase (also known as ST6GAL1).

In yet another non-limiting aspect, sialic acid capping was enhanced by supplementing the cell culture media with N-acetylmannosamine (also known as 1,3,4-O-$Bu_3$ManNAc), which is a "high-flux" precursor of sialic acid.

In certain embodiments, enhancing protein sialyation by expressing the biologic in CHO cells stably transfected with human alpha-2,6-sialyltransferase substantially improved ENPP1-Fc bioavailability ($C_{max}$) when dosed subcutaneously. In other embodiments, increasing the pH-dependent FcRn-mediated cellular recycling by manipulating the Fc domain led to improvements of in vivo biologic half-life. In yet other embodiments, combining CHO cells stably transfected with human α-2,6-sialyltransferase and growing the cells in N-acetylmannosamine led to dramatic increases half-life and/or biologic exposure (AUC). In yet other embodiments, combining two or more methods described herein into a single construct led to dramatic increases in half-life and/or biologic exposure (AUC).

In certain embodiments, the polypeptides of the disclosure are more highly glycosylated than other ENPP1-Fc polypeptides in the art. In other embodiments, the polypeptides of the disclosure have higher affinity for the neonatal orphan receptor (FcRn) than other ENPP1-Fc polypeptides in the art. In yet other embodiments, the polypeptides of the disclosure have higher in vivo half-lives than other ENPP1-Fc polypeptides in the art. In yet other embodiments, the kinetic properties of the parent polypeptide (Construct #770) are altered such that the changes represent a "gain of function" alteration in the enzymatic rate constants. In yet other embodiments, the kinetic properties of the parent polypeptide (Construct #770) are not significantly altered by certain site-directed mutagenesis, and thus the resulting mutant enzyme has enzymatic rate constants that are substantively identical to the parent polypeptide. In yet other embodiments, certain point mutations in the parent polypeptide lead to introduction of a glycan at the mutated residue, increasing biologic exposure for the mutant polypeptide. In yet other non-limiting embodiments, the increase in biologic exposure for the mutant polypeptide is due to increased biologic absorption and/or circulation of the mutant polypeptide.

In certain embodiments, any of the ENPP1 mutant polypeptides described herein retain ENPP1 catalytic activity as compared to a soluble ENPP1 polypeptide comprising or consisting of amino acids 23-849 of SEQ ID NO:7. In certain embodiments, any of the ENPP1 mutant polypeptides described herein retain at least about 30% (e.g., at least about 30%, 35%, 40%, 45%, 50%, 55%, 60%, 65%, 70%, 75%, 80%, 85%, 90%, 95%, 96%, 9%7, 98%, 99%, 99.5%, 99.8%, or 100%) of the catalytic activity of a soluble ENPP1 polypeptide comprising or consisting of amino acids 23-849 of SEQ ID NO:7. In certain embodiments, any one the ENPP1 mutant polypeptides described herein has greater catalytic activity than a soluble ENPP1 polypeptide comprising or consisting of amino acids 23-849 of SEQ ID NO: 7.

In certain embodiments, any of the ENPP1 mutant polypeptides described herein has improved pharmacokinetic and/or bioavailability properties in a mammal as compared to a soluble ENPP1 polypeptide comprising or consisting of amino acids 23-849 of SEQ ID NO: 7. In certain embodiments, any of the ENPP1 mutant polypeptides have a circulating half-life in a mammal that is at least 30% (e.g., at least about 30%, 35%, 40%, 45%, 50%, 55%, 60%, 65%, 70%, 75%, 80%, 85%, 90%, 95%, 96%, 9%7, 98%, 99%, 99.5%, 99.8%, 100%, 120%, 140%, 160%, 180%, 200%, 250%, 300%, 350%, 400%, 450%, 500%, or greater than 500%) than the circulating half-life of a soluble ENPP1 polypeptide comprising or consisting of amino acids 23-849 of SEQ ID NO:7. In certain embodiments, any one the ENPP1 mutant polypeptides described herein has a greater AUC than that of a soluble ENPP1 polypeptide comprising or consisting of amino acids 23-849 of SEQ ID NO:7.

In certain embodiments, the in vivo half-life of an ENPP1-Fc polypeptide of the disclosure is at least about 1.5, 2, 2.5, 3, 4, 5, 6, 7, 8, 9, 10, 12, 14, 16, 18, or 20 times higher than the ENPP-1 polypeptides described in the art. In other embodiments, the polypeptides of the disclosure are administered to the subject at a lower dose and/or at a lower frequency than other ENPP1-Fc polypeptides in the art. In yet other embodiments, the polypeptides of the disclosure are administered to the subject once a month, twice a month, three times a month, and/or four times a month. In yet other embodiments, the lower frequency administration of the polypeptides of the disclosure results in better patient compliance and/or increased efficacy as compared with other ENPP1-Fc polypeptides in the art.

In certain embodiments, an ENPP1-Fc polypeptide of the disclosure can be used to raise pyrophosphate (PPi) levels in a subject having PPi level lower than normal level (which is around 2 μM). In other embodiments, an ENPP1-Fc polypeptide of the disclosure can be used to reduce or prevent progression of pathological calcification or ossification in a subject having PPi levels lower than normal level. In yet other embodiments, an ENPP1-Fc polypeptide of the disclosure can be used to treat ENPP1 deficiency manifested by a reduction of extracellular PPi concentration in a subject.

In certain embodiment, the steady state level of plasma PPi achieved after administration of a first dosage of a construct of the disclosure is maintained for a time period of at least 2 days, at least 4 days, at least a week or at least a month.

In certain embodiment, a second dosage of a construct of the disclosure is administered after a suitable time interval of after two days, after four days, after a week, or after a month to the subject so that the steady state level of plasma PPi is maintained at a constant or steady state level and does not return to the lower level of PPi that the subject had prior to the administration of first dosage of constructs of the disclosure.

Without wishing to be bound by theory, it is believed that maintaining a steady state concentration of plasma PPi at normal levels reduces and/or prevents progression of pathological calcification and pathological ossification of subjects.

Certain ENPP1 polypeptides, mutants, or mutant fragments thereof, have been previously disclosed in International PCT Application Publications No. WO 2012/125182, WO 2014/126965, WO 2016/187408, and WO 2018/027024, all of which are incorporated by reference in their entireties herein.

Reference will now be made in detail to certain embodiments of the disclosed subject matter. While the disclosed subject matter will be described in conjunction with the enumerated claims, it will be understood that the exemplified subject matter is not intended to limit the claims to the disclosed subject matter.

Throughout this document, values expressed in a range format should be interpreted in a flexible manner to include not only the numerical values explicitly recited as the limits of the range, but also to include all the individual numerical values or sub-ranges encompassed within that range as if each numerical value and sub-range is explicitly recited. For example, a range of "about 0.1% to about 5%" or "about 0.1% to 5%" should be interpreted to include not just about 0.1% to about 5%, but also the individual values (e.g., 1%, 2%, 3%, and 4%) and the sub-ranges (e.g., 0.1% to 0.5%, 1.1% to 2.2%, 3.3% to 4.4%) within the indicated range. The statement "about X to Y" has the same meaning as "about X to about Y," unless indicated otherwise. Likewise, the statement "about X, Y, or about Z" has the same meaning as "about X, about Y, or about Z," unless indicated otherwise.

Definitions

As used herein, each of the following terms has the meaning associated with it in this section. Unless defined otherwise, all technical and scientific terms used herein generally have the same meaning as commonly understood by one of ordinary skill in the art to which this disclosure belongs. Generally, the nomenclature used herein and the laboratory procedures in animal pharmacology, pharmaceutical science, separation science, and organic chemistry are those well-known and commonly employed in the art. It should be understood that the order of steps or order for performing certain actions is immaterial, so long as the present teachings remain operable. Any use of section headings is intended to aid reading of the document and is not to be interpreted as limiting; information that is relevant to a section heading may occur within or outside of that particular section. All publications, patents, and patent documents referred to in this document are incorporated by reference herein in their entirety, as though individually incorporated by reference.

In the application, where an element or component is said to be included in and/or selected from a list of recited elements or components, it should be understood that the element or component can be any one of the recited elements or components and can be selected from a group consisting of two or more of the recited elements or components.

In the methods described herein, the acts can be carried out in any order, except when a temporal or operational sequence is explicitly recited. Furthermore, specified acts can be carried out concurrently unless explicit claim language recites that they be carried out separately. For example, a claimed act of doing X and a claimed act of doing Y can be conducted simultaneously within a single operation, and the resulting process will fall within the literal scope of the claimed process.

In this document, the terms “a,” “an,” or “the” are used to include one or more than one unless the context clearly dictates otherwise. The term “or” is used to refer to a nonexclusive “or” unless otherwise indicated. The statement “at least one of A and B” or “at least one of A or B” has the same meaning as “A, B, or A and B.”

The following notation conventions are applied to the present disclosure for the sake of clarity. In any case, any teaching herein that does not follow this convention is still part of the present disclosure, and can be fully understood in view of the context in which the teaching is disclosed. Protein symbols are disclosed in non-italicized capital letters. As non-limiting examples, ‘ENPP1’ refer to the protein. In certain embodiments, if the protein is a human protein, an ‘h’ is used before the protein symbol. In other embodiments, if the protein is a mouse protein, an ‘m’ is used before the symbol. Hence, human ENPP1 is referred to as ‘hENPP1’, and mouse ENPP1 is referred to as ‘mENPP1’. Human gene symbols are disclosed in italicized capital letters. As a non-limiting example, the human gene corresponding to the protein hENPP1 is ENPP1. Mouse gene symbols are disclosed with the first letter in upper case and the remaining letters in lower case; further, the mouse gene symbol is italicized. As a non-limiting example, the mouse gene that makes the protein mEnpp1 is Enpp1. Notations about gene mutations are shown as uppercase text.

“About” as used herein when referring to a measurable value such as an amount, a temporal duration, and the like, is meant to encompass variations of ±20% or ±10%, in certain embodiments ±5%, in certain embodiments ±1%, in certain embodiments ±0.1% from the specified value, as such variations are appropriate to perform the disclosed methods.

A disease or disorder is “alleviated” if the severity of a symptom of the disease or disorder, the frequency with which such a symptom is experienced by a patient, or both, is reduced.

As used herein the terms “alteration,” “defect,” “variation” or “mutation” refer to a mutation in a gene in a cell that affects the function, activity, expression (transcription or translation) or conformation of the polypeptide it encodes, including missense and nonsense mutations, insertions, deletions, frameshifts and premature terminations.

The term “antibody,” as used herein, refers to an immunoglobulin molecule that is able to specifically bind to a specific epitope on an antigen. Antibodies can be intact immunoglobulins derived from natural sources or from recombinant sources and can be immunoreactive portions of intact immunoglobulins.

The “ATP hydrolytic activity” of ENPP1 can be determined by using an ATP cleavage assay. ENPP1 readily hydrolyzes ATP into AMP and PPi. The steady-state Michaelis-Menten enzymatic constants of ENPP1 are determined using ATP as a substrate. ENPP1 can be demonstrated to cleave ATP by HPLC analysis of the enzymatic reaction, and the identity of the substrates and products of the reaction are confirmed by using ATP, AMP, and ADP standards. The ATP substrate degrades over time in the presence of ENPP1, with the accumulation of the enzymatic product AMP. Using varying concentrations of ATP substrate, the initial rate velocities for ENPP1 are derived in the presence of ATP, and the data is fit to a curve to derive the enzymatic rate constants. At physiologic pH, the kinetic rate constants of NPP1 are $K_m$=144 UM and $k_{cat}$=7.8 $s^{-1}$.

As used herein, the term “AUC” refers to the area under the plasma drug concentration-time curve (AUC) and correlates with actual body exposure to drug after administration of a dose of the drug. In certain embodiments, the AUC is expressed in mg*h/L. The AUC can be used to measure bioavailability of a drug, which is the fraction of unchanged drug that is absorbed intact and reaches the site of action, or the systemic circulation following administration by any route.

AUC can be calculated used Linear Trapezoidal method or Logarithmic Trapezoidal method. The Linear Trapezoidal method uses linear interpolation between data points to calculate the AUC. This method is required by the OGD and FDA, and is the standard for bioequivalence trials. For a given time interval ($t_1$-$t_2$), the AUC can be calculated as follows:

$$AUC = \frac{1}{2}(C_1 + C_2)(t_2 - t_1)$$

wherein $C_1$ and $C_2$ are the average concentration over the time interval ($t_1$ and $t_2$).

The Logarithmic Trapezoidal method uses logarithmic interpolation between data points to calculate the AUC. This method is more accurate when concentrations are decreasing because drug elimination is exponential (which makes it linear on a logarithmic scale). For a given time interval ($t_1$-$t_2$), the AUC can be calculated as follows (assuming that $C_1 > C_2$):

$$AUC = \frac{C_1 - C_2}{\ln(C_1) - \ln(C_2)}(t_2 - t_1)$$

The term “bioavailability” as used herein refers to the extent and rate at which the active moiety (protein or drug or metabolite) enters systemic circulation, thereby accessing the site of action, or the systemic circulation following administration by any route. Bioavailability of an active moiety is largely determined by the properties of the dosage form, which depend partly on its design and manufacture. Differences in bioavailability among formulations of a given drug or protein can have clinical significance; thus, knowing whether drug formulations are equivalent is essential. The most reliable measure of a drug’s or protein’s bioavailability is area under the plasma concentration-time curve (AUC). AUC is directly proportional to the total amount of unchanged drug or therapeutic protein that reaches systemic circulation. Drug or therapeutic protein may be considered bioequivalent in extent and rate of absorption if their plasma concentration curves are essentially superimposable. For an intravenous dose of a drug, bioavailability is defined as unity. For drug administered by other routes of administration, bioavailability is often less than unity. Incomplete bioavailability may be due to a number of factors that can be subdivided into categories of dosage form effects, membrane effects, and site of administration effect. Half-life and AUC provide information about the bioavailability of a drug or biologic.

As used herein, the terms “conservative variation” or “conservative substitution” as used herein refers to the replacement of an amino acid residue by another, biologically similar residue. Conservative variations or substitutions are not likely to change the shape of the peptide chain. Examples of conservative variations, or substitutions, include the replacement of one hydrophobic residue such as isoleucine, valine, leucine or methionine for another, or the substitution of one polar residue for another, such as the substitution of arginine for lysine, glutamic for aspartic acid, or glutamine for asparagine.

As used herein, a "construct" of the disclosure refers to a fusion polypeptide comprising an ENPP1 polypeptide, or a fragment or site directed mutant thereof.

A "disease" is a state of health of an animal wherein the animal cannot maintain homeostasis, and wherein if the disease is not ameliorated then the animal's health continues to deteriorate.

A "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

As used herein, the terms "effective amount," "pharmaceutically effective amount" and "therapeutically effective amount" refer to a nontoxic but sufficient amount of an agent to provide the desired biological result. That result may be reduction and/or alleviation of the signs, symptoms, or causes of a disease, or any other desired alteration of a biological system. An appropriate therapeutic amount in any individual case may be determined by one of ordinary skill in the art using routine experimentation.

As used herein, the term "ENPP" or "NPP" refers to ectonucleotide pyrophosphatase/phosphodiesterase.

As used herein, the term "ENPP1 protein" or "ENPP1 polypeptide" refers to ectonucleotide pyrophosphatase/phosphodiesterase-1 protein encoded by the ENPP1 gene. The encoded protein is a type II transmembrane glycoprotein and cleaves a variety of substrates, including phosphodiester bonds of nucleotides and nucleotide sugars and pyrophosphate bonds of nucleotides and nucleotide sugars. ENPP1 protein has a transmembrane domain and soluble extracellular domain. The extracellular domain is further subdivided into somatomedin B domain, catalytic domain, and the nuclease domain. The sequence and structure of wild-type ENPP1 is described in detail in PCT Application Publication No. WO 2014/126965 to Braddock, et al., which is incorporated herein in its entirety by reference.

As used herein, the term "human ENPP1" refers to the human ENPP1 sequence as described in NCBI accession NP_006199. As used herein, the term "soluble human ENPP1" refers to the polypeptide corresponding to residues 96 to 925 of NCBI accession NP_006199. As used herein, the term "enzymatically active" with respect to ENPP1 is defined as being capable of binding and hydrolyzing ATP into AMP and PPi and/or AP3a into ATP.

As used herein, the term "ENPP1 precursor protein" refers to ENPP1 with its signal peptide sequence at the ENPP1 N-terminus. Upon proteolysis, the signal sequence is cleaved from ENPP1 to provide the ENPP1 protein. Signal peptide sequences useful within the disclosure include, but are not limited to, ENPP1 signal peptide sequence, ENPP2 signal peptide sequence, ENPP7 signal peptide sequence, and/or ENPP5 signal peptide sequence.

As used herein, the term "ENPP1-Fc" refers to ENPP1 recombinantly fused and/or chemically conjugated (including both covalent and non-covalent conjugations) to an FcR binding domain of an IgG molecule (preferably, a human IgG). In certain embodiments, the C-terminus of ENPP1 is fused or conjugated to the N-terminus of the FcR binding domain.

As used herein, the term "Fc" refers to a human IgG (immunoglobulin) Fc domain. Subtypes of IgG such as IgG1, IgG2, IgG3, and IgG4 are contemplated for usage as Fc domains.

As used herein, the "Fc region" is the portion of an IgG molecule that correlates to a crystallizable fragment obtained by papain digestion of an IgG molecule. The Fc region comprises the C-terminal half of the two heavy chains of an IgG molecule that are linked by disulfide bonds. It has no antigen binding activity but contains the carbohydrate moiety and the binding sites for complement and Fc receptors, including the FcRn receptor. The Fc fragment contains the entire second constant domain CH2 (residues 231-340 of human IgG1, according to the Kabat numbering system) and the third constant domain CH3 (residues 341-447). The term "IgG hinge-Fc region" or "hinge-Fc fragment" refers to a region of an IgG molecule consisting of the Fc region (residues 231-447) and a hinge region (residues 216-230) extending from the N-terminus of the Fc region. The term "constant domain" refers to the portion of an immunoglobulin molecule having a more conserved amino acid sequence relative to the other portion of the immunoglobulin, the variable domain, which contains the antigen binding site. The constant domain contains the CH1, CH2 and CH3 domains of the heavy chain and the CHL domain of the light chain.

As used herein, the term "Fc receptors" refer to proteins found on the surface of certain cells (including, among others, B lymphocytes, follicular dendritic cells, natural killer cells, macrophages, neutrophils, eosinophils, basophils, human platelets, and mast cells) that contribute to the protective functions of the immune system. Fc receptors bind to antibodies that are attached to infected cells or invading pathogens. Immunoglobulin Fc receptors (FcRs) are expressed on all hematopoietic cells and play crucial roles in antibody-mediated immune responses. Binding of immune complexes to FcR activates effector cells, leading to phagocytosis, endocytosis of IgG-opsonized particles, releases of inflammatory mediators, and antibody-dependent cellular cytotoxicity (ADCC). Fc receptors have been described for all classes of immunoglobulins: FcγR and neonatal FcR (FcRn) for IgG, FcεR for IgE, FcαR for IgA, FcδR for IgD and FcμR for IgM. All known Fc receptors structurally belong to the immunoglobulin superfamily, except for FcRn and FcεRII, which are structurally related to class I Major Histocompatibility antigens and C-type lectins, respectively (*Fc Receptors*, Neil A. Fangera, et al., in Encyclopedia of Immunology ($2^{nd}$ Edition), 1998).

As used herein, the term "FcRn Receptor" refers to the neonatal Fc receptor (FcRn), also known as the Brambell receptor, which is a protein that in humans is encoded by the FCGRT gene. An FcRn specifically binds the Fc domain of an antibody. FcRn extends the half-life of IgG and serum albumin by reducing lysosomal degradation in endothelial cells. IgG, serum albumin, and other serum proteins are continuously internalized through pinocytosis. Generally, serum proteins are transported from the endosomes to the lysosome, where they are degraded. FcRn-mediated transcytosis of IgG across epithelial cells is possible because FcRn binds IgG at acidic pH (<6.5) but not at neutral or higher pH. IgG and serum albumin are bound by FcRn at the slightly acidic pH (<6.5), and recycled to the cell surface where they are released at the neutral pH (>7.0) of blood. In this way IgG and serum albumin avoid lysosomal degradation.

The Fc portion of an IgG molecule is located in the constant region of the heavy chain, notably in the CH2 domain. The Fc region binds to an Fc receptor (FcRn), which is a surface receptor of a B cell and also proteins of the complement system. The binding of the Fc region of an IgG molecule to an FcRn activates the cell bearing the receptor and thus activates the immune system. The Fc residues critical to the mouse Fc-mouse FcRn and human Fc-human FcRn interactions have been identified (Dall'Acqua et al., 2002, J. Immunol. 169 (9): 5171-80). An FcRn binding domain comprises the CH2 domain (or a FcRn binding portion thereof) of an IgG molecule.

As used herein, the term "fragment," as applied to a nucleic acid, refers to a subsequence of a larger nucleic acid. A "fragment" of a nucleic acid can be at least about 15, 50-100, 100-500, 500-1000, 1000-1500 nucleotides, 1500-2500, or 2500 nucleotides (and any integer value in between). As used herein, the term "fragment," as applied to a protein or peptide, refers to a subsequence of a larger protein or peptide, and can be at least about 20, 50, 100, 200, 300 or 400 amino acids in length (and any integer value in between).

The term "functional equivalent" or "functional derivative" denotes, in the context of a functional derivative of an amino acid sequence, a molecule that retains a biological activity (either function or structural) that is substantially similar to that of sequences of ENPP1-Fc constructs shown herein. A functional derivative or equivalent may be a natural derivative or is prepared synthetically. The functionally-equivalent polypeptides of the disclosure can also be polypeptides identified using one or more techniques of structural and or sequence alignment known in art.

Exemplary functional derivatives include amino acid sequences having substitutions, deletions, or additions of one or more amino acids, provided that the biological activity of the protein is conserved. The substituting amino acid desirably has chemico-physical properties which are similar to that of the substituted amino acid. Desirable similar chemico-physical properties include, similarities in charge, bulkiness, hydrophobicity, hydrophilicity, and the like. Typically, greater than 30% identity between two polypeptides is considered to be an indication of functional equivalence. Preferably, functionally equivalent polypeptides of the disclosure have a degree of sequence identity with the ENPP1-Fc constructs of greater than 80%. More preferred polypeptides have degrees of identity of greater than 85%, 90%, 95%, 98% or 99%, respectively. Method for determining whether a functional equivalent or functional derivative has the same or similar or higher biological activity than the ENPP1-Fc construct can be determined by using the Enzymology assays involving ATP cleavage described in WO2016/187408.

"Gene transfer" and "gene delivery" refer to methods or systems for reliably inserting a particular nucleic acid sequence into targeted cells.

An "inducible" promoter is a nucleotide sequence that, when operably linked with a polynucleotide that encodes or specifies a gene product, causes the gene product to be produced in a cell substantially only when an inducer that corresponds to the promoter is present in the cell.

As used herein, the term "in vivo half-life" for a protein and/or polypeptide contemplated within the disclosure (such as, for example, an ENPP1 polypeptide containing FcRn binding sites) refers to the time required for half the quantity administered in the animal to be cleared from the circulation and/or other tissues in the animal. When a clearance curve of an ENPP1-Fc fusion protein is constructed as a function of time, the curve is usually biphasic with a rapid $\alpha$-phase (which represents an equilibration of the administered molecules between the intra- and extra-vascular space and which is, in part, determined by the size of molecules), and a longer $\beta$-phase (which represents the catabolism of the molecules in the intravascular space). In certain embodiments, the term "in vivo half-life" in practice corresponds to the half-life of the molecules in the $\beta$-phase.

"Instructional material," as that term is used herein, includes a publication, a recording, a diagram, or any other medium of expression that can be used to communicate the usefulness of the nucleic acid, peptide, and/or compound of the disclosure in the kit for identifying or alleviating or treating the various diseases or disorders recited herein.

"Isolated" means altered or removed from the natural state. For example, a nucleic acid or a polypeptide naturally present in a living animal is not "isolated," but the same nucleic acid or polypeptide partially or completely separated from the coexisting materials of its natural state is "isolated." An isolated nucleic acid or protein can exist in substantially purified form, or can exist in a non-native environment such as, for example, a host cell.

An "isolated nucleic acid" refers to a nucleic acid segment or fragment which has been separated from sequences which flank it in a naturally occurring state, i.e., a DNA fragment which has been removed from the sequences that are normally adjacent to the fragment, i.e., the sequences adjacent to the fragment in a genome in which it naturally occurs. The term also applies to nucleic acids that have been substantially purified from other components which naturally accompany the nucleic acid, i.e., RNA or DNA or proteins, which naturally accompany it in the cell. The term therefore includes, for example, a recombinant DNA that is incorporated into a vector, into an autonomously replicating plasmid or virus, or into the genomic DNA of a prokaryote or eukaryote, or which exists as a separate molecule (i.e., as a cDNA or a genomic or cDNA fragment produced by PCR or restriction enzyme digestion) independent of other sequences. It also includes a recombinant DNA that is part of a hybrid gene encoding additional polypeptide sequence.

An "oligonucleotide" or "polynucleotide" is a nucleic acid ranging from at least 2, in certain embodiments at least 8, 15 or 25 nucleotides in length, but may be up to 50, 100, 1000, or 5000 nucleotides long or a compound that specifically hybridizes to a polynucleotide.

The term "operably linked" refers to functional linkage between a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame.

As used herein, the term "patient," "individual" or "subject" refers to a human.

As used herein, the term "pharmaceutical composition" or "composition" refers to a mixture of at least one compound useful within the disclosure with a pharmaceutically acceptable carrier. The pharmaceutical composition facilitates administration of the compound to a patient. Multiple techniques of administering a compound exist in the art including, but not limited to, subcutaneous, intravenous, oral, aerosol, inhalational, rectal, vaginal, transdermal, intranasal, buccal, sublingual, parenteral, intrathecal, intragastrical, ophthalmic, pulmonary, and topical administration.

As used herein, the term "pharmaceutically acceptable" refers to a material, such as a carrier or diluent, which does not abrogate the biological activity or properties of the compound, and is relatively non-toxic, i.e., the material may be administered to an individual without causing undesirable biological effects or interacting in a deleterious manner with any of the components of the composition in which it is contained.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the disclosure within or to the patient such that it may perform its intended function. Each carrier must be "acceptable" in the sense of being compatible with the other ingredients of the formulation, including the compound useful within the disclosure, and not injurious to the patient. Some examples of materials that may serve as pharmaceutically acceptable carriers include: sugars, such as lactose, glucose and sucrose; starches, such as corn starch and potato starch; cellulose, and its derivatives. As used herein, "pharmaceutically acceptable carrier" also includes any and all coatings, antibacterial and antifungal agents, and absorption delaying agents, and the like that are compatible with the activity of the compound useful within the disclosure, and are physiologically acceptable to the patient. The "pharmaceutically acceptable carrier" may further include a pharmaceutically acceptable salt of the compound useful within the disclosure. Other additional ingredients that may be included in the pharmaceutical compositions used in the practice of the disclosure are known in the art and described, for example in Remington's Pharmaceutical Sciences (Genaro, Ed., Mack Publishing Co., 1985, Easton, PA), which is incorporated herein by reference.

As used herein, the language "pharmaceutically acceptable salt" refers to a salt of the administered compound prepared from pharmaceutically acceptable non-toxic acids and bases, including inorganic acids, inorganic bases, organic acids, inorganic bases, solvates, hydrates, and clathrates thereof.

As used herein the term "plasma pyrophosphate (PPi) levels" refers to the amount of pyrophosphate present in plasma of animals. In certain embodiments, animals include rat, mouse, cat, dog, human, cow and horse. It is necessary to measure PPi in plasma rather than serum because of release from platelets. There are several ways to measure PPi, one of which is by enzymatic assay using uridine-diphosphoglucose (UDPG) pyrophosphorylase (Lust & Seegmiller, 1976, Clin. Chim. Acta 66:241-249; Cheung & Suhadolnik, 1977, Anal. Biochem. 83:61-63) with modifications. Typically normal PPi levels in healthy subjects range from about 1 μm to about 3 μM, in some cases between 1-2 μM. Subjects with defective ENPP1 expression tend to exhibit low PPi levels ranging from at least 10% below normal levels, at least 20% below normal levels, at least 30% below normal levels, at least 40% below normal levels, at least 50% below normal levels, at least 60% below normal levels, at least 70% below normal levels, at least 80% below normal levels, and any combinations thereof. In patients afflicted with diseases of pathological calcification or ossification, the PPi levels in blood plasma are found to be less than 1 μM and in some cases are below detection levels. In some cases, the plasma PPi levels of subjects afflicted with diseases of pathological calcification or ossification are below 0.5 μM (Arterioscler Thromb Vasc Biol. 2014, 34 (9): 1985-9; Braddock et al., 2015, Nat Commun. 6:10006.)

As used herein, the term "polypeptide" refers to a polymer composed of amino acid residues, related naturally occurring structural variants, and synthetic non-naturally occurring analogues thereof linked via peptide bonds.

As used herein, the term "PPi" refers to pyrophosphate.

As used herein, the term "prevent" or "prevention" means no disorder or disease development if none had occurred, or no further disorder or disease development if there had already been development of the disorder or disease. Also considered is the ability of one to prevent some or all of the symptoms associated with the disorder or disease.

The term "promoter" as used herein is defined as a DNA sequence recognized by the synthetic machinery of the cell, or introduced synthetic machinery, required to initiate the specific transcription of a polynucleotide sequence.

As used herein, the term "promoter/regulatory sequence" means a nucleic acid sequence which is required for expression of a gene product operably linked to the promoter/regulatory sequence. In some instances, this sequence may be the core promoter sequence and in other instances, this sequence may also include an enhancer sequence and other regulatory elements that are required for expression of the gene product. The promoter/regulatory sequence may for example be one that expresses the gene product in a tissue specific manner.

The term "recombinant polypeptide" as used herein is defined as a polypeptide produced by using recombinant DNA methods.

The term "recombinant DNA" as used herein is defined as DNA produced by joining pieces of DNA from different sources.

"Sample" or "biological sample" as used herein means a biological material isolated from a subject. The biological sample may contain any biological material suitable for detecting a mRNA, polypeptide or other marker of a physiologic or pathologic process in a subject, and may comprise fluid, tissue, cellular and/or non-cellular material obtained from the individual.

As used herein, the term "signal peptide" refers to a sequence of amino acid residues (ranging in length from, for example, 10-30 residues) bound at the amino terminus of a nascent protein of interest during protein translation. The signal peptide is recognized by the signal recognition particle (SRP) and cleaved by the signal peptidase following transport at the endoplasmic reticulum. (Lodish, et al., 2000, Molecular Cell Biology, $4^{th}$ edition).

As used herein, "substantially purified" refers to being essentially free of other components. For example, a substantially purified polypeptide is a polypeptide that has been separated from other components with which it is normally associated in its naturally occurring state. Non-limiting embodiments include 95% purity, 99% purity, 99.5% purity, 99.9% purity and 100% purity.

A "tissue-specific" promoter is a nucleotide sequence that, when operably linked with a polynucleotide encodes or specified by a gene, causes the gene product to be produced in a cell substantially only if the cell is a cell of the tissue type corresponding to the promoter. The phrase "under transcriptional control" or "operatively linked" as used herein means that the promoter is in the correct location and orientation in relation to a polynucleotide to control the initiation of transcription by RNA polymerase and expression of the polynucleotide.

The term "transfected" or "transformed" or "transduced" as used herein refers to a process by which exogenous nucleic acid is transferred or introduced into the host cell. A "transfected" or "transformed" or "transduced" cell has been transfected, transformed or transduced with exogenous nucleic acid. The cell includes the primary subject cell and its progeny.

As used herein, the term "treatment" or "treating" is defined as the application or administration of a therapeutic agent, i.e., a compound useful within the disclosure (alone or in combination with another pharmaceutical agent), to a patient, or application or administration of a therapeutic agent to an isolated tissue or cell line from a patient (e.g., for diagnosis or ex vivo applications), who has a disease or disorder, a symptom of a disease or disorder or the potential to develop a disease or disorder, with the purpose to cure, heal, alleviate, relieve, alter, remedy, ameliorate, improve or affect the disease or disorder, the symptoms of the disease or disorder, or the potential to develop the disease or disorder. Such treatments may be specifically tailored or modified, based on knowledge obtained from the field of pharmacogenomics.

"Variant" as the term is used herein, is a nucleic acid sequence or a peptide sequence that differs in sequence from a reference nucleic acid sequence or peptide sequence respectively, but retains essential properties of the reference molecule. Changes in the sequence of a nucleic acid variant may not alter the amino acid sequence of a peptide encoded by the reference nucleic acid, or may result in amino acid substitutions, additions, deletions, fusions and truncations. Changes in the sequence of peptide variants are typically limited or conservative, so that the sequences of the reference peptide and the variant are closely similar overall and, in many regions, identical. A variant and reference peptide may differ in amino acid sequence by one or more substitutions, additions, or deletions in any combination. A variant of a nucleic acid or peptide may be a naturally occurring such as an allelic variant, or may be a variant that is not known to occur naturally. Non-naturally occurring variants of nucleic acids and peptides may be made by mutagenesis techniques or by direct synthesis.

A "vector" is a composition of matter that comprises an isolated nucleic acid and that may be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, and the like.

As used herein, the term "virus" is defined as a particle consisting of nucleic acid (RNA or DNA) enclosed in a protein coat, with or without an outer lipid envelope, which is capable of transfecting the cell with its nucleic acid.

As used herein, the term "wild-type" refers to a gene or gene product isolated from a naturally occurring source. A wild-type gene is most frequently observed in a population and is thus arbitrarily designed the "normal" or "wild-type" form of the gene. In contrast, the term "modified" or "mutant" refers to a gene or gene product that displays modifications in sequence and/or functional properties (i.e., altered characteristics) when compared to the wild-type gene or gene product. Naturally occurring mutants can be isolated; these are identified by the fact that they have altered characteristics (including altered nucleic acid sequences) when compared to the wild-type gene or gene product.

The following abbreviations are used herein: 1,3,4-O-$Bu_3$ManNAc, N-acetylmannosamine; ST6GAL1, ST6 beta-galactoside alpha-2,6-sialyltransferase.

Ranges: throughout this disclosure, various aspects of the disclosure can be presented in a range format. It should be understood that the description in range format is merely for convenience and brevity and should not be construed as an inflexible limitation on the scope of the disclosure. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Polypeptides

In one aspect, the disclosure provides an ENPP1-Fc polypeptide. The disclosure contemplates that the polypeptide of the disclosure can have one or more of the mutations described herein.

In another aspect, the disclosure provides an ENPP1 mutant polypeptide comprising at least one amino acid substitution at position 256 as relating to SEQ ID NO:7. In certain embodiments, the amino acid substitution is the substitution of isoleucine (I) for threonine (T) at position 256 relative to SEQ ID NO:7. In certain embodiments, the amino acid substitution is the substitution of isoleucine (I) for serine(S) at position 256 relative to SEQ ID NO: 7.

In certain embodiments, the ENPP1 mutant polypeptide comprises the catalytic domain of ENPP1. In certain embodiments, the ENPP1 mutant polypeptide comprises the endonuclease domain of ENPP1. In certain embodiments, the ENPP1 mutant polypeptide lacks the nuclease domain of ENPP1. In certain embodiments, the ENPP1 mutant polypeptide lacks the transmembrane domain of ENPP1. In certain embodiments, the ENPP1 mutant polypeptide lacks the intracellular domain of ENPP1. In certain embodiments, the ENPP1 mutant polypeptide lacks both the intracellular domain and the transmembrane domains of ENPP1. In certain embodiments, the ENPP1 mutant polypeptide lacks a signal sequence. In certain embodiments, the ENPP1 mutant polypeptide comprises an amino acid sequence that is at least about 90% (e.g., at least about 91%, 92%, 93%, 94%, 95%, 96%, 97%, 98%, or 99%) identical to amino acids 23-849 of SEQ ID NO:7.

In another aspect, the disclosure provides an ENPP1 mutant polypeptide comprising an amino acid sequence that is at least about 90% (e.g., at least about 91%, 92%, 93%, 94%, 95%, 96%, 97%, 98%, or 99%) identical to amino acids 23-849 of SEQ ID NO:7, wherein the mutant polypeptide comprises an amino acid substitution at position 256 as relating to SEQ ID NO:7. In certain embodiments, the amino acid substitution is I256T. In certain embodiments, the amino acid substitution is I256S.

In yet another aspect, the disclosure provides an ENPP1 mutant polypeptide comprising amino acids 23-849 of SEQ ID NO:7 in which no more than ten (10) (e.g., no more than 9, no more than 8, no more than 7, no more than 6, no more than 5, no more than 4, no more than 3, no more than 2, or no more than one) amino acid substitution(s) relative to amino acids 23-849 of SEQ ID NO:7 are present. In certain embodiments, the ENPP1 mutant polypeptide comprises an amino acid substitution at position 256 relative to SEQ ID NO: 7. In certain embodiments, the amino acid substitution is I256T. In certain embodiments, the amino acid substitution is I256S.

Figure 16A:
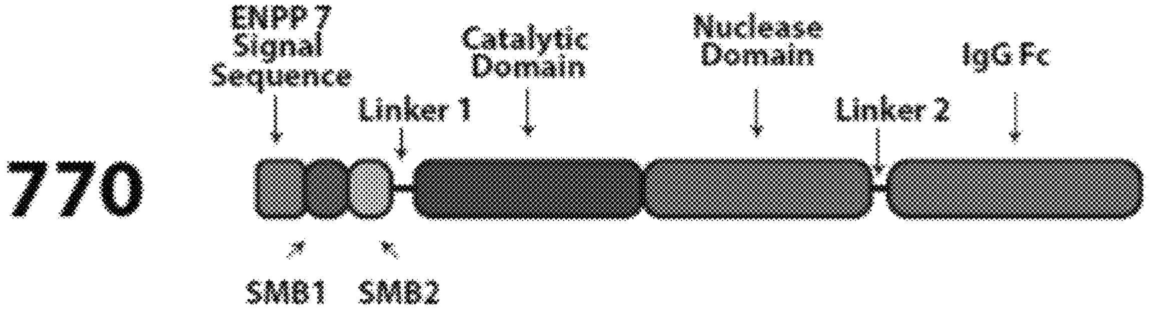
FIG. 16A-16B illustrate domains of ENPP1 and selected point mutations introduced into the parent polypeptide (SEQ ID NO:7). The figure identifies specific point mutations introduced into SEQ ID NO:7. Constructs that have been stably transfected into CHO cells stably transfected with human α-2,6-ST are referred with an "ST". PK and bioavailability data are presented in the table, determined as illustrated in FIGS. 4, 5, and 13 and calculated using Equation 1.
Figure 16B:
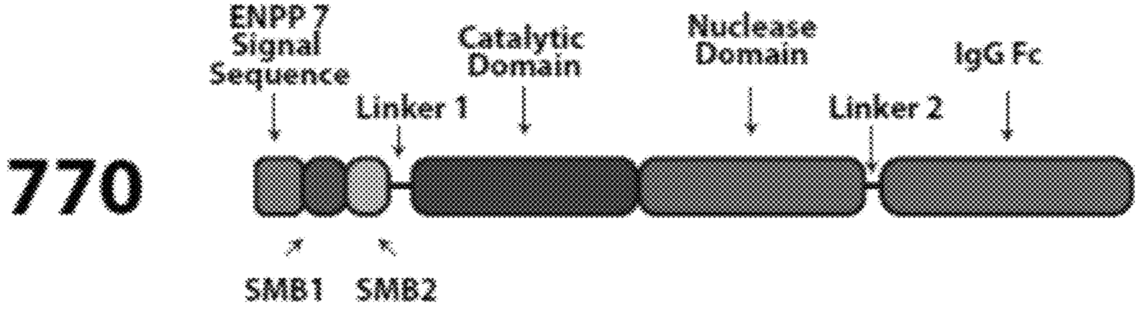
Figure 17:
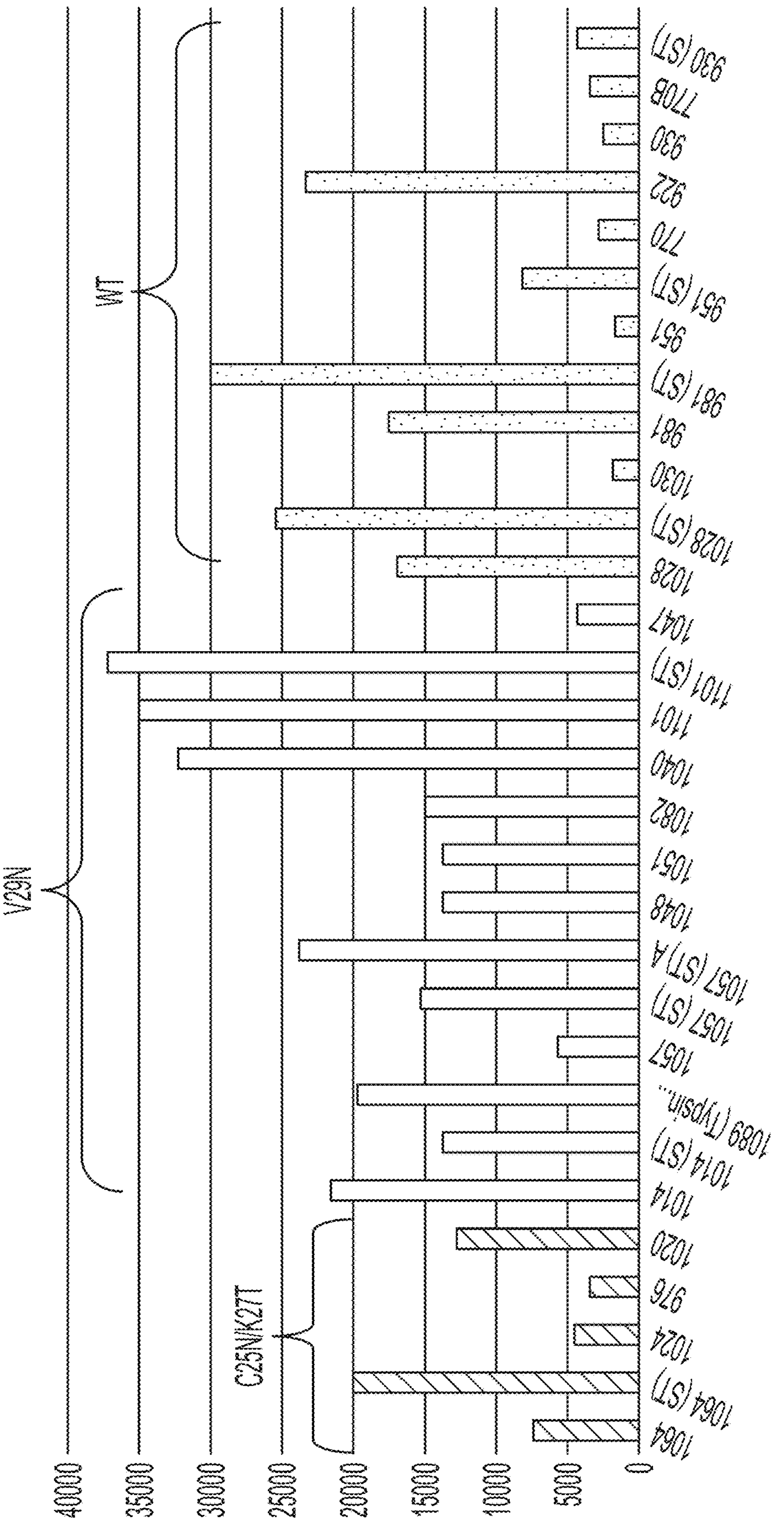
FIG. 17 illustrates bioavailability (as Area Under Curve, or AUC) for certain Constructs of the disclosure, as sorted by signal sequence (N-terminus region) region mutations.

In certain embodiments, the ENPP1 polypeptide comprises at least one mutation in the signal sequence region as recited in FIG. 16A and/or FIG. 16B.

In certain embodiments, the polypeptide comprises mutation I256T as relating to SEQ ID NO: 7.

In certain embodiments, the mutation is selected from the group consisting of C25N, K27T, and V29N as relating to SEQ ID NO:7. In certain embodiments, the mutation is C25N as relating to SEQ ID NO:7. In certain embodiments, the mutation is K27T as relating to SEQ ID NO:7. In certain embodiments, the mutation is V29N as relating to SEQ ID NO:7. In certain embodiments, the ENPP1 polypeptide comprises at least one mutation selected from the group consisting of C25N/K27T and V29N as relating to SEQ ID NO:7.

In certain embodiments, the ENPP1 polypeptide comprises at least one mutation in the catalytic region as recited in FIG. 16A and/or FIG. 16B. In certain embodiments, the mutation is selected from the group consisting of I256T, K369N, and I371T as relating to SEQ ID NO:7. In certain embodiments, the mutation is I256Y as relating to SEQ ID NO:7. In certain embodiments, the mutation is K369N as relating to SEQ ID NO:7. In certain embodiments, the mutation is I371T as relating to SEQ ID NO:7. In certain embodiments, the ENPP1 polypeptide comprises at least one mutation selected from the group consisting of I256T and K369N/I371T as relating to SEQ ID NO:7.

Figure 18:
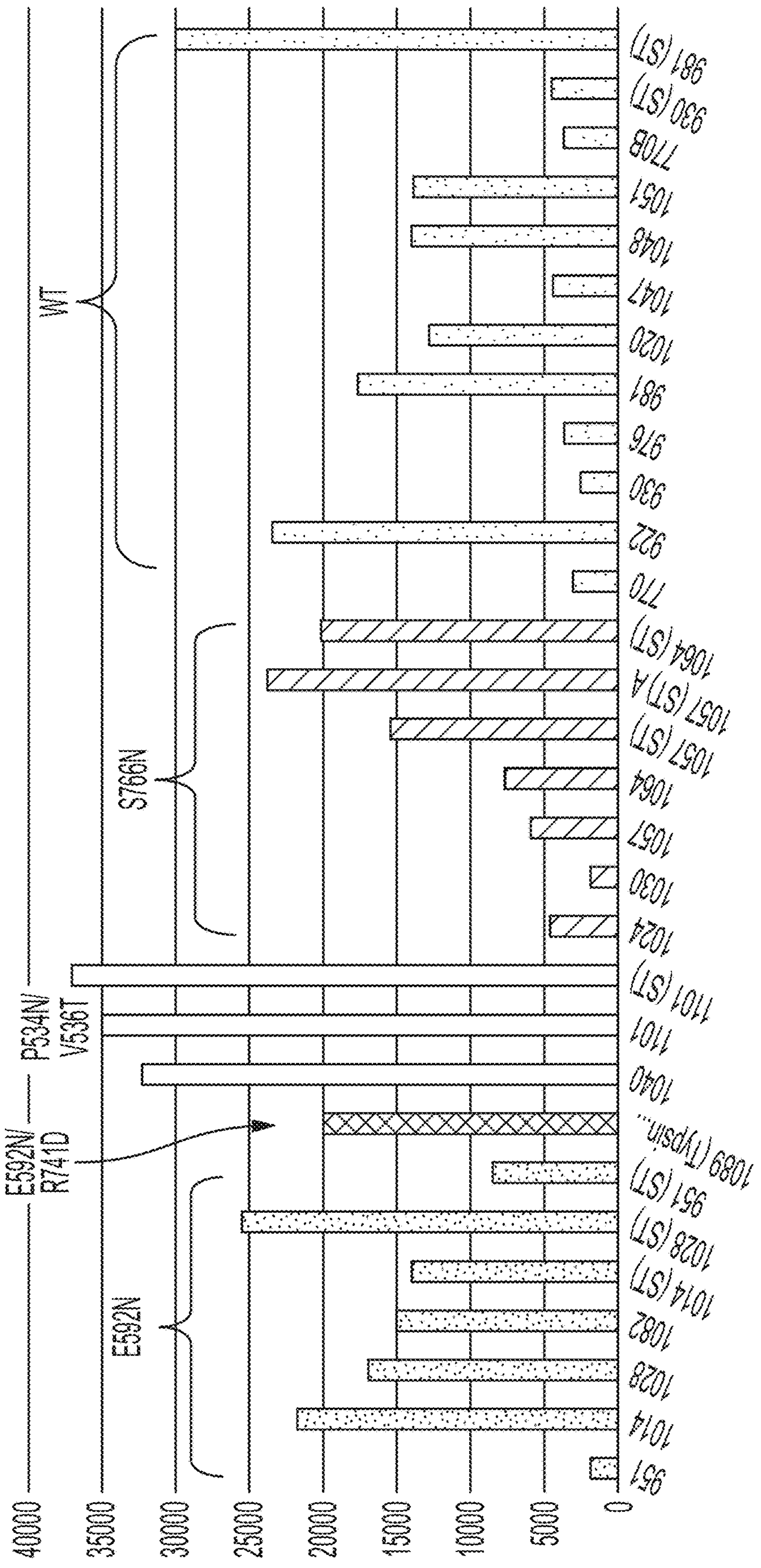
FIG. 18 illustrates bioavailability (as Area Under Curve, or AUC) for certain Constructs of the disclosure, as sorted by endonuclease region mutations.
Figure 19A:
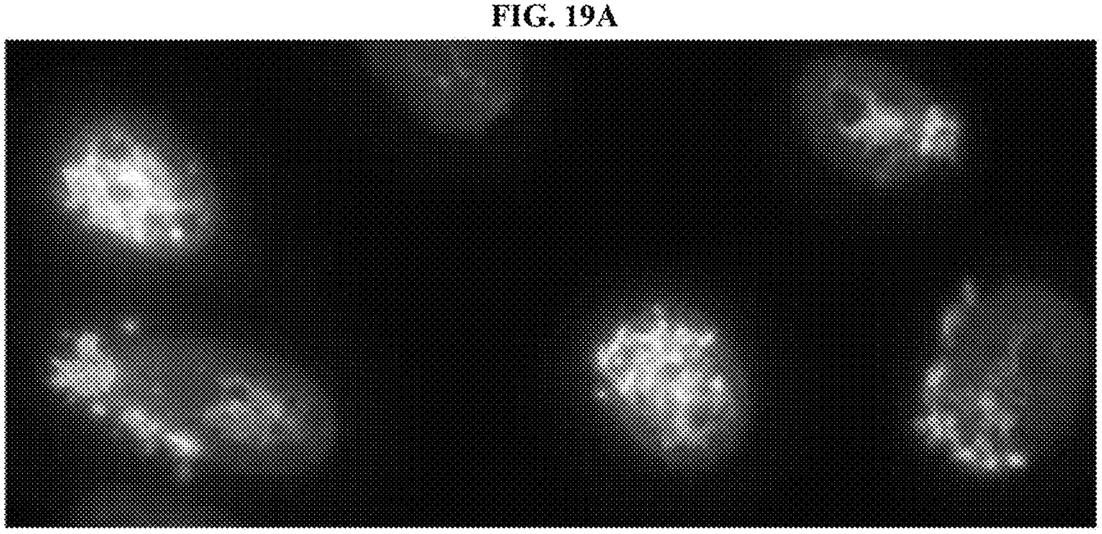
FIG. 19A comprises an image illustrating stable CHO cell sub-clones co-transfected with plasmid cDNA for both ENPP1-Fc and hST6GAL1 where screened for expression of alpha-2,6-sialyltransferase by immunofluorescence of paraformaldehyde fixed cells using a rabbit anti-hST6GAl1 antibody (R&D Systems cat #AF5924) followed by donkey polyclonal Goat IgG Alexa Fluor594 (Abcam Ab150140). Characteristic Golgi localization was observed with those cell clones that were also positive by Western blot with the same antibody.
Figure 19B:
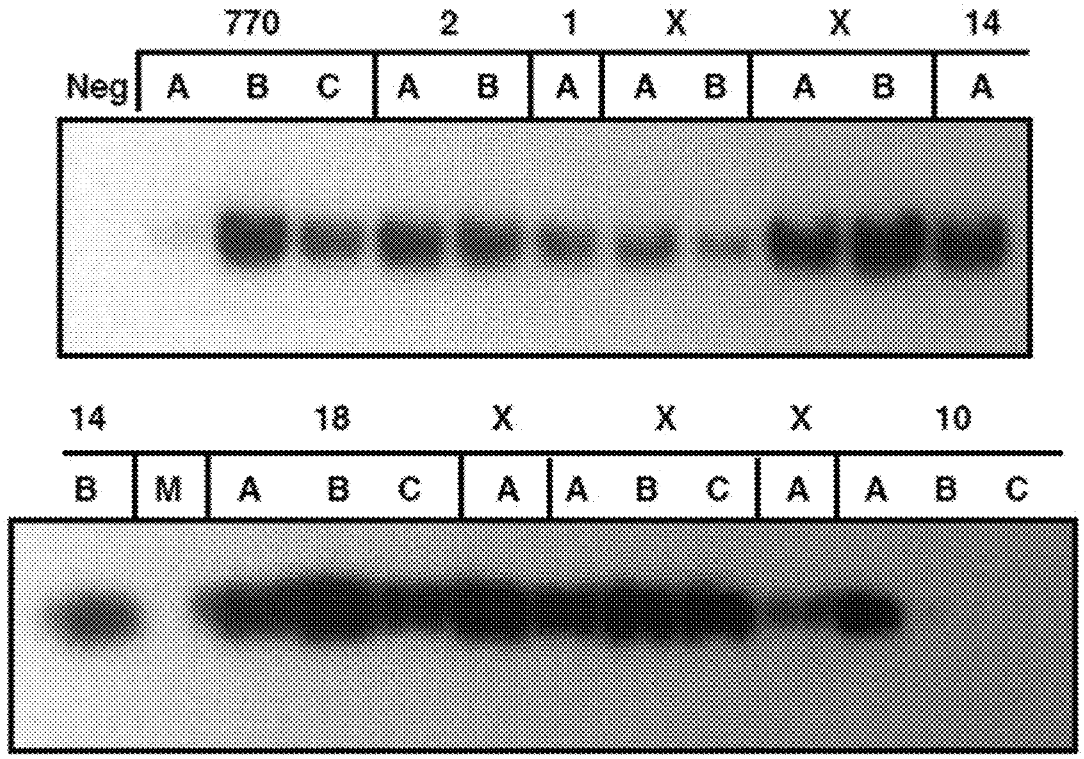
FIG. 19B illustrates a representative western blot using the same primary antibody as FIG. 19A demonstrates a single band at approximately 48 kD indicating expression of alpha-2,6-sialyltransferase at varying intensities for some of the CHO cell sub-clones used in this study. The first lane is CHO cell lysate untransfected as a negative control. The next 3 lanes are 3 unique sub-clones of the unmodified parent plasmid 770 labeled A, B, and C. The other lanes are a selection of sub-clones used in the paper for Clones 1, 2, 10, 14, and 18. The "X" represents sub-clones of constructs that were not used further herein.

In certain embodiments, the ENPP1 polypeptide comprises at least one mutation in the endonuclease domain as recited in Table 1, Table 2, Table 3, Table 4, Table 5, FIG. 7A, FIG. 16A, FIG. 16B, FIG. 17, and/or FIG. 18. In certain embodiments, the mutation is selected from the group consisting of P534N, V536T, R545T, P554L, E592N, R741D, and S766N as relating to SEQ ID NO:7. In certain embodiments, the mutation is P534N as relating to SEQ ID NO:7. In certain embodiments, the mutation is V536T as relating to SEQ ID NO: 7. In certain embodiments, the mutation is R545T as relating to SEQ ID NO:7. In certain embodiments, the mutation is P554L as relating to SEQ ID NO:7. In certain embodiments, the mutation is E592N as relating to SEQ ID NO:7. In certain embodiments, the mutation is R741D as relating to SEQ ID NO:7. In certain embodiments, the mutation is S766N as relating to SEQ ID NO:7. In certain embodiments, the ENPP1 polypeptide comprises at least one mutation selected from the group consisting of P534N/V536T, P554L/R545T, E592N, E592N/R741D, and S766N as relating to SEQ ID NO:7.

In certain embodiments, the ENPP1 polypeptide comprises at least one mutation in the linker region as recited in FIG. 16A and/or FIG. 16B. In certain embodiments, the mutation is selected from the group consisting of E864N and L866T as relating to SEQ ID NO: 7. In certain embodiments, the ENPP1 polypeptide comprises at least the mutation E864N/L866T as relating to SEQ ID NO:7. In certain embodiments, the mutation is E864N as relating to SEQ ID NO:7. In certain embodiments, the mutation is L866T as relating to SEQ ID NO:7.

In certain embodiments, the polypeptide comprises an ENPP1 polypeptide and an FcRn binding domain, wherein the FcRn binding domain comprises any mutation recited in Table 1, Table 2, FIG. 7A, FIG. 16A, FIG. 16B, FIG. 17, and/or FIG. 18. In certain embodiments, the mutation is selected from the group consisting of M883Y, S885N, S885T, T887E, H1064K, and N1065F as relating to SEQ ID NO:7. In certain embodiments, the mutation is M883Y as relating to SEQ ID NO:7. In certain embodiments, the mutation is S885N as relating to SEQ ID NO:7. In certain embodiments, the mutation is S885T as relating to SEQ ID NO:7. In certain embodiments, the mutation is T887E as relating to SEQ ID NO: 7. In certain embodiments, the mutation is H1064K as relating to SEQ ID NO:7. In certain embodiments, the mutation is N1065F as relating to SEQ ID NO:7. In certain embodiments, the FcRn binding domain comprises at least one mutation selected from the group consisting of S885N, M883Y, M883Y/S885T/T887E, and H1064K/N1065F as relating to SEQ ID NO:7.

In certain embodiments, the ENPP1 polypeptide comprises at least one mutation selected from the group consisting of C25N, K27T, V29N, C25N/K27T, I256T, K369N, I371T, K369N/I371T, P534N, V536T, R545T, P554L, E592N, R741D, S766N, P534N/V536T, P554L/R545T, E592N/R741D, E864N, L866T, E864N/L866T, M883Y, S885N, S885T, T887E, H1064K, N1065F, M883Y/S885T/T887E, H1064K/N1065F as relating to SEQ ID NO:7.

In certain embodiments, the polypeptide comprises at least one mutation selected from the group consisting of S885N, S766N, M883Y/S885T/T887E, E864N/L866T, P534N/V536T/H1064K/N1065F, P554L/R545T, S766N/H1064K/N1065F, E592N/H1064K/N1065F, and P534N/V536T/M883Y/S885T/T887E as relating to SEQ ID NO: 7.

In certain embodiments, the polypeptide comprises an ENPP1 polypeptide and an FcRn binding domain, the polypeptide comprising mutations M883Y, S885T, and T887E as relating to SEQ ID NO:7.

In certain embodiments, the polypeptide comprises an ENPP1 polypeptide and an FcRn binding domain, the polypeptide comprising mutations P534N, V536T, M883Y, S885T, and T887E as relating to SEQ ID NO:7.

In certain embodiments, the polypeptide comprises an ENPP1 polypeptide and an FcRn binding domain, the polypeptide comprising mutations E592N, H1064K, and N1065F as relating to SEQ ID NO:7.

In certain embodiments, the polypeptide comprises an ENPP1 mutant polypeptide, wherein the mutant polypeptide comprises an ENPP1 mutation selected from the group consisting of S766N, P534N, V536T, P554L, R545T, and E592N as relating to SEQ ID NO: 7.

In certain embodiments, the ENPP1 mutant polypeptide comprises at least one mutation selected from the group consisting of S766N, P534N/V536T, P554L/R545T, and E592N as relating to SEQ ID NO:7.

In certain embodiments, the polypeptide further comprises an FcRn binding domain of an IgG.

In certain embodiments, the polypeptide comprises mutations selected from the group consisting of: S885N, S766N, M883Y/S885T/T887E, P534N/V536T/H1064K/N1065F, P554L/R545T, S766N/H1064K/N1065F, E592N/H1064K/N1065F, and P534N/V536T/M883Y/S885T/T887E as relating to SEQ ID NO:7.

In certain embodiments, the polypeptide comprises an S885N mutation in the FcRn binding domain as relating to SEQ ID NO:7.

In certain embodiments, the polypeptide comprises an S766N mutation in the ENPP1 mutant polypeptide as relating to SEQ ID NO:7.

In certain embodiments, the polypeptide comprises mutations M883Y, S885T, and T887E in the FcRn binding domain as relating to SEQ ID NO:7.

In certain embodiments, the polypeptide comprises mutations P534N and V536T in the ENPP1 mutant polypeptide and mutations H1064K and N1065F in the FcRn binding domain as relating to SEQ ID NO:7.

In certain embodiments, the polypeptide comprises mutations P554L and R545T in the ENPP1 mutant polypeptide as relating to SEQ ID NO:7.

In certain embodiments, the polypeptide comprises mutation S766N in the ENPP1 mutant polypeptide and mutations H1064K and N1065F in the FcRn binding domain as relating to SEQ ID NO:7.

In certain embodiments, the polypeptide comprises mutation E592N in the ENPP1 mutant polypeptide and mutations H1064K and N1065F in the FcRn binding domain as relating to SEQ ID NO:7.

In certain embodiments, the polypeptide comprises mutations P534N and V536T in the ENPP1 mutant polypeptide and mutations M883Y, S885T, and T887E in the FcRn binding domain as relating to SEQ ID NO:7.

In certain embodiments, the polypeptide comprises mutation I256T as relating to SEQ ID NO: 7.

In certain embodiments, the polypeptide comprises mutations I256T, M883Y, S885T, and T887E as relating to SEQ ID NO:7.

In certain embodiments, the polypeptide comprises mutations V29N, I256T, P534N, V536T, M883Y, S885T, and T887E as relating to SEQ ID NO:7.

In another aspect, the disclosure features an ENPP1 mutant polypeptide comprising an amino acid sequence that is at least about 90% (e.g., at least about 91%, 92%, 93%, 94%, 95%, 96%, 97%, 98%, or 99%) identical to amino acids 23-849 of SEQ ID NO:7, wherein the mutant polypeptide comprises mutation I256T as relating to SEQ ID NO:7, and further comprises a mutation selected from the group consisting of S766N, P534N, V536T, P554L, R545T, and E592N as relating to SEQ ID NO:7.

In certain embodiments, any of the mutant polypeptides described herein comprises at least one amino acid substitution selected from the group consisting of S766N, P534N/V536T, P554L/R545T, and E592N as relating to SEQ ID NO:7.

In certain embodiments, any of the mutant polypeptides described herein comprises the amino acid substitution V29N.

In certain embodiments, the mutant polypeptide comprises or consists of the amino acid sequence depicted in SEQ ID NO:11.

Also featured are ENPP1 mutant polypeptide fusions comprising any of the ENPP1 mutant polypeptides described herein and a heterologous protein, such as an FcRn binding domain. In certain embodiments, the heterologous protein is carboxy-terminal to the ENPP1 mutant polypeptide portion of the fusion. In certain embodiments, the heterologous protein is amino-terminal to the ENPP1 mutant polypeptide portion of the fusion.

In certain embodiments of any of the fusions described herein, the FcRn binding domain is an albumin polypeptide. In certain embodiments, the FcRn binding domain is a Fc portion of an immunoglobulin molecule, such as an IgG1 immunoglobulin molecule.

In certain embodiments of any of the fusions described herein, the FcRn binding domain comprises one more amino acid substitutions relative to a wild type FcRn binding domain. In certain embodiments the FcRn binding domain is the Fc portion of a human IgG1 molecule and comprises the following amino acid substitutions: M883Y, S885T, and T887E (the MST/YTE substitutions), each relative to SEQ ID NO:7.

In certain embodiments, a fusion described herein comprises one or more of the following substitutions: S885N, S766N, M883Y/S885T/T887E, P534N/V536T/H1064K/N1065F, P554L/R545T, S766N/H1064K/N1065F, E592N/H1064K/N1065F, or P534N/V536T/M883Y/S885T/T887E, each as relating to SEQ ID NO: 7.

In certain embodiments of any of the ENPP1 mutant polypeptides or fusions described herein, the ENPP1 mutant polypeptide comprises or consists of the amino acid sequence depicted in SEQ ID NO:11.

In certain embodiments of any of the ENPP1 mutant polypeptides or fusions described herein, the ENPP1 mutant polypeptide comprises or consists of the amino acid sequence depicted in SEQ ID NO:12.

In certain embodiments, any of the fusions described herein comprise: (a) an ENPP1 mutant polypeptide comprising or consisting of the amino acid sequence depicted in SEQ ID NO: 11 or SEQ ID NO:12, (b) a variant human IgG1 Fc region, such as the amino acid sequence depicted in SEQ ID NO:14, which is carboxy-terminal to the ENPP1 mutant polypeptide; and (c) a linker amino acid sequence separating (a) and (b), wherein the linker sequence is LIN (SEQ ID NO:8) or GGGGS (SEQ ID NO:9).

Also featured herein are conjugates of any one of the ENPP1 mutant polypeptides or ENPP1 mutant polypeptide fusions described herein and a heterologous moiety, such as but not limited to a small molecule. In certain embodiments, the heterologous moiety increases or further increases the pharmacokinetic and/or bioavailability of the mutant polypeptides in a mammal. In certain embodiments, the heterologous moiety is an oligomer of ethylene glycol and/or propylene glycol, such as but not limited to polyethylene glycol (PEG) and/or polypropylene glycol (PPG).

In certain embodiments, any of the ENPP1 mutant polypeptide fusions or conjugates described herein comprises the S885N mutation as relating to SEQ ID NO:7.

In certain embodiments, any of the ENPP1 mutant polypeptides, fusions, or conjugates described herein comprises the S766N mutation as relating to SEQ ID NO:7.

In certain embodiments, any of the ENPP1 mutant polypeptide fusions or conjugates described herein comprises mutations M883Y, S885T, and T887E as relating to SEQ ID NO: 7.

In certain embodiments, any of the ENPP1 mutant polypeptides, fusions, or conjugates described herein comprises mutations P534N, V536T, H1064K, and N1065F as relating to SEQ ID NO:7.

In certain embodiments, any of the ENPP1 mutant polypeptides, fusions, or conjugates described herein comprises mutations P554L and R545T as relating to SEQ ID NO: 7.

In certain embodiments, any of the ENPP1 mutant polypeptides, fusions, or conjugates described herein comprises mutation S766N, H1064K, and N1065F as relating to SEQ ID NO:7.

In certain embodiments, any of the ENPP1 mutant polypeptides, fusions, or conjugates described herein comprises mutation E592N, H1064K, and N1065F as relating to SEQ ID NO:7.

In certain embodiments, any of the ENPP1 mutant polypeptides, fusions, or conjugates described herein comprises mutations P534N, V536T, M883Y, S885T, and T887E as relating to SEQ ID NO:7.

In another aspect, the disclosure provides an ENPP1 mutant polypeptide fusion comprising an ENPP1 mutant polypeptide fused to a Fc region of an immunoglobulin, wherein the ENPP1 mutant polypeptide comprises a substitution at position 256 relative to SEQ ID NO:7.

In certain embodiments of any of the fusions described herein, the Fc region comprises at least one mutation selected from the group consisting of M883Y, S885N, S885T, T887E, H1064K, and N1065F as relating to SEQ ID NO:7.

In certain embodiments of any of the fusions described herein, the Fc region comprises at least one mutation selected from the group consisting of S885N, M883Y, M883Y/S885T/T887E, and H1064K/N1065F as relating to SEQ ID NO:7.

In certain embodiments, the ENPP1 mutant polypeptide further comprises at least one mutation selected from the group consisting of C25N, K27T, and V29N as relating to SEQ ID NO: 7.

In certain embodiments, an ENPP1 mutant polypeptide, or a fusion described herein comprises at least one mutation selected from the group consisting of C25N/K27T and V29N as relating to SEQ ID NO:7.

In certain embodiments, an ENPP1 mutant polypeptide described herein further comprises at least one mutation selected from the group consisting of K369N and I371T as relating to SEQ ID NO:7.

In certain embodiments, an ENPP1 mutant polypeptide, or a fusion comprising such a mutant polypeptide, described herein comprises the mutation K369N/I371T as relating to SEQ ID NO:7.

In certain embodiments, an ENPP1 mutant polypeptide, or fusion comprising such a mutant polypeptide, described herein further comprises at least one mutation selected from the group consisting of P534N, V536T, R545T, P554L, E592N, R741D, and S766N as relating to SEQ ID NO:7.

In certain embodiments, an ENPP1 mutant polypeptide, or a fusion comprising such a mutant polypeptide, described herein comprises at least one mutation selected from the group consisting of P534N/V536T, P554L/R545T, E592N, E592N/R741D, and S766N as relating to SEQ ID NO:7.

In certain embodiments, any of the ENPP1 mutant polypeptides or fusions described herein further comprises at least one mutation selected from the group consisting of E864N and L866T as relating to SEQ ID NO:7.

In certain embodiments, any of the ENPP1 mutant polypeptides or fusions described herein comprises at least the mutation E864N/L866T as relating to SEQ ID NO:7.

In certain embodiments, any of the ENPP1 mutant polypeptides or fusions described herein comprise at least one mutation selected from the group consisting of C25N, K27T, V29N, C25N/K27T, K369N, I371T, K369N/I371T, P534N, V536T, R545T, P554L, E592N, R741D, S766N, P534N/V536T, P554L/R545T, E592N/R741D, E864N, L866T, E864N/L866T, M883Y, S885N, S885T, T887E, H1064K, N1065F, M883Y/S885T/T887E, H1064K/N1065F as relating to SEQ ID NO:7.

In certain embodiments, any of the fusions described herein comprise an Fc region of an IgG, such as IgG1.

In certain embodiments, any of the ENPP1 mutant polypeptides described herein, or the fusion proteins comprising such ENPP1 mutant polypeptides, comprise at least one mutation selected from the group consisting of P534N, V536T, R545T, P554L, S766N, and E592N as relating to SEQ ID NO:7.

In certain embodiments, any of the ENPP1 mutant polypeptides described herein, or the fusion proteins comprising such ENPP1 mutant polypeptides, comprise at least one mutation selected from the group consisting of S766N, P534N/Y536T, P554L/R545T, and E592N as relating to SEQ ID NO:7.

In certain embodiments, any of the ENPP1 mutant polypeptides described herein, or the fusion proteins comprising such ENPP1 mutant polypeptides, comprise at least one mutation selected from the group consisting of S885N, S766N, M883Y/S885T/T887E, E864N/L866T, P534N/V536T/H1064K/N1065F, P554L/R545T, S766N/H1064K/N1065F, E592N/H1064K/N1065F, and P534N/V536T/M883Y/S885T/T887E as relating to SEQ ID NO: 7.

In certain embodiments, any of the fusions described herein comprise mutations I256T, M883Y, S885T, and T887E as relating to SEQ ID NO:7.

In certain embodiments, any of the fusions described herein comprise an ENPP1 polypeptide and a Fc region of an immunoglobulin, the polypeptide fusion comprising mutations I256T, P534N, V536T, M883Y, S885T, and T887E as relating to SEQ ID NO:7.

In certain embodiments, any of the fusions described herein comprise the ENPP1 polypeptide fusion comprising an ENPP1 polypeptide and a Fc region of an immunoglobulin, the polypeptide fusion comprising mutations I256T, E592N, H1064K, and N1065F as relating to SEQ ID NO:7.

In certain embodiments, the ENPP1 mutant polypeptide fusions described herein comprise a linker amino acid sequence, for example, between the ENPP1 mutant polypeptide portion of the fusion and the heterologous protein moiety. In certain embodiments, the linker amino acid sequence comprises or consists of SEQ ID NO:8. In certain embodiments, the linker amino acid sequence comprises or consists of SEQ ID NO:9, wherein n=1, n=2, n=3, n=4, n=5, n=6, n=7, n=8, n=9, or n=10.

In yet another aspect, the disclosure features ENPP1-containing polypeptides comprising or consisting of the amino acid sequence depicted in SEQ ID NO:15 or SEQ ID NO: 16, and conjugates thereof.

In certain embodiments, the ENPP1 polypeptide lacks a nuclease domain. In other embodiments, the ENPP1 polypeptide is truncated to remove the nuclease domain. In yet other embodiments, the ENPP1 polypeptide is truncated to remove the nuclease domain from about residue 524 to about residue 885 relative to SEQ ID NO:1, leaving only the catalytic domain from about residue 186 to about residue 586 relative to SEQ ID NO:1, which serves to preserve the catalytic activity of the protein.

In certain embodiments, the ENPP1 polypeptide is modified with a segment of the extracellular region of ENPP1 containing a peptidase cleavage site after the signal peptide, and between the transmembrane and extracellular domain, as compared to SEQ ID NO:1.

In certain embodiments, the ENPP1 polypeptide is modified with a segment of the extracellular region of ENPP1 containing a furin cleavage site between the transmembrane and extracellular domain, as compared to SEQ ID NO:1. In other embodiments, the ENPP1 polypeptide is not modified with a segment of the extracellular region of ENPP1 containing a furin cleavage site between the transmembrane and extracellular domain, as compared to SEQ ID NO:1.

In certain embodiments, the ENPP1 polypeptide is modified with a segment of the extracellular region of ENPP2 containing a signal peptidase cleavage site, as compared to SEQ ID NO:1. In other embodiments, the ENPP1 polypeptide is not modified with a segment of the extracellular region of ENPP2 containing a signal peptidase cleavage site, as compared to SEQ ID NO:1.

In yet another aspect, the disclosure provides an ENPP1 mutant polypeptide, a ENPP1-containing polypeptide, or a fusion, which is expressed from a CHO cell line stably transfected with human ST6 beta-galactoside alpha-2,6-sialyltransferase (also known as ST6GAL1).

In yet another aspect, the disclosure provides an ENPP1 mutant polypeptide, a ENPP1-containing polypeptide, or a fusion, which is grown in a cell culture supplemented with sialic acid and/or N-acetylmannosamine (also known as 1,3,4-O-Bu3ManNAc).

Also provides herein are pharmaceutical compositions comprising any one of the ENPP1 mutant polypeptides, the ENPP1 mutant polypeptide fusions, conjugates, or other polypeptides and proteins described herein and a pharmaceutically acceptable carrier.

In certain embodiments, the polypeptide is soluble. In other embodiments, the polypeptide is a recombinant polypeptide. In yet other embodiments, the polypeptide comprises an ENPP1 polypeptide that lacks the ENPP1 transmembrane domain. In yet other embodiments, the polypeptide comprises an ENPP1 polypeptide wherein the ENPP1 transmembrane domain has been removed (and/or truncated) and replaced with the transmembrane domain of another polypeptide, such as, by way of non-limiting example, ENPP2, ENPP5, or ENPP7.

In certain embodiments, the polypeptide comprises a signal peptide resulting in the secretion of a precursor of the ENPP1 polypeptide, which undergoes proteolytic processing to yield a polypeptide comprising the ENPP1 polypeptide. In other embodiments, the signal peptide is selected from the group consisting of signal peptides of ENPP2, ENPP5, and ENPP7. In yet other embodiments, the polypeptide comprises an ENPP1 polypeptide comprising transmembrane domains of ENPP1 and another polypeptide, such as, by way of non-limiting example, ENPP2. In yet other embodiments, the ENPP1 polypeptide comprises a cleavage product of a precursor ENPP1 polypeptide comprising an ENPP2 transmembrane domain. In yet other embodiments, the ENPP2 transmembrane domain comprises residues 12-30 of SEQ ID NO:7, which corresponds to IISLFTFAVGVNICLGFTA.

In certain embodiments, the ENPP1 polypeptide is C-terminally fused to the Fc domain of human immunoglobulin 1 (IgG1), human immunoglobulin 2 (IgG2), human immunoglobulin 3 (IgG3), and/or human immunoglobulin 4 (IgG4). In other embodiments, the ENPP1 polypeptide is N-terminally fused to the Fc domain of human immunoglobulin 1 (IgG1), human immunoglobulin 2 (IgG2), human immunoglobulin 3 (IgG3), and/or human immunoglobulin 4 (IgG4). In yet other embodiments, the presence of IgFc domain improves half-life, solubility, reduces immunogenicity, and increases the activity of the ENPP1 polypeptide.

In certain embodiments, the ENPP1 polypeptide is C-terminally fused to human serum albumin. Human serum albumin may be conjugated to ENPP1 protein through a chemical linker, including but not limited to naturally occurring or engineered disulfide bonds, or by genetic fusion to ENPP1, or a fragment and/or variant thereof.

In certain embodiments, the polypeptide is further pegylated (fused with a poly(ethylene glycol) chain).

In certain embodiments, the polypeptide has a $k_{cat}$ value for the substrate ATP greater than or equal to about 3.4 (±0.4) $s^{-1}$ $enzyme^{-1}$, wherein the $k_{cat}$ is determined by measuring the rate of hydrolysis of ATP for the polypeptide.

In certain embodiments, the polypeptide has a $K_M$ value for the substrate ATP less than or equal to about 2 μM, wherein the $K_M$ is determined by measuring the rate of hydrolysis of ATP for the polypeptide.

In certain embodiments, the polypeptide is formulated as a liquid formulation. In other embodiments, the disclosure provides a dry product form of a pharmaceutical composition comprising a therapeutic amount of a polypeptide of the disclosure, whereby the dry product is reconstitutable to a solution of the compound in liquid form.

The disclosure provides a kit comprising at least one polypeptide of the disclosure, or a salt or solvate thereof, and instructions for using the polypeptide within the methods of the disclosure.

In certain embodiments, the polypeptide lacks a negatively-charged bone-targeting sequence. In yet other embodiments, a polyaspartic acid domain (from about 2 to about 20 or more sequential aspartic acid residues) is a non-limiting example of a negatively-charged bone-targeting sequence. In other embodiments, the polypeptide has a negatively-charged bone-targeting sequence.

It will be understood that an ENPP1 polypeptide according to the disclosure includes not only the native human proteins, but also any fragment, derivative, fusion, conjugate or mutant thereof having ATP hydrolytic activity of the native protein. As used herein in this disclosure, the phrase "an ENPP1 polypeptide, mutant, or mutant fragment thereof" also includes any compound or polypeptide (such as, but not limited to, a fusion protein) comprising an ENPP1 polypeptide, mutant, or mutant fragment thereof. Fusion proteins according to the disclosure are considered biological equivalents of ENPP1, but are intended to provide longer half-life or greater potency due to increased in vivo biologic exposure, as judged by the "area under the curve" (AUC) or increased half-life in pharmacokinetic experiments.

Vectors and Cells

Also provided herein are nucleic acids that encode any one of the ENPP1 mutant polypeptides, ENPP1-containing polypeptides, or fusions described herein. The disclosure further provides vectors, such as expression vectors, that comprise such nucleic acids. Also provided are a cell, cells, or a plurality of cells (e.g., mammalian cells) that comprise any one of the nucleic acids, vectors, or expression vectors described herein. Also provided are methods for producing a protein (e.g., any one of the ENPP1 mutant polypeptides, ENPP1-containing polypeptides, or fusions described herein), the methods in certain embodiments comprising culturing the cell, cells, or plurality of cells under conditions suitable for expression of the protein by the cell or cells from the nucleic acid, vector, or expression vector. The methods can also include purifying the protein from the cell, cells, or plurality of cells, or from the media in which the cell, cells, or plurality of cells were cultured. In addition, the disclosure provides proteins purified by any such methods.

The disclosure further provides an autonomously replicating or an integrative mammalian cell vector comprising a recombinant nucleic acid encoding a polypeptide of the disclosure. In certain embodiments, the vector comprises a plasmid or a virus. In other embodiments, the vector comprises a mammalian cell expression vector. In yet other embodiments, the vector further comprises at least one nucleic acid sequence that directs and/or controls expression of the polypeptide. In yet other embodiments, the recombinant nucleic acid encodes a polypeptide comprising an ENPP1 polypeptide of the disclosure and to a signal peptide, wherein the polypeptide is proteolytically processed upon secretion from a cell to yield the ENPP1 polypeptide of the disclosure.

In yet another aspect, the disclosure provides an isolated host cell comprising a vector of the disclosure. In certain embodiments, the cell is a non-human cell. In other embodiments, the cell is mammalian. In yet other embodiments, the vector of the disclosure comprises a recombinant nucleic acid encoding a polypeptide comprising a ENPP1 polypeptide of the disclosure and a signal peptide. In yet other embodiments, the polypeptide is proteolytically processed upon secretion from a cell to yield the ENPP1 polypeptide of the disclosure.

Cloning and Expression of ENPP1

ENPP1, or a ENPP1 polypeptide, is prepared as described in US 2015/0359858 A1, which is incorporated herein in its entirety by reference. ENPP1 is a transmembrane protein localized to the cell surface with distinct intramembrane domains. In order to express ENPP1 as a soluble extracellular protein, the transmembrane domain of ENPP1 may be swapped for the transmembrane domain of ENPP2, which results in the accumulation of soluble, recombinant ENPP1 in the extracellular fluid of the baculovirus cultures.

Signal sequences of any other known proteins may be used to target the extracellular domain of ENPP1 for secretion as well, such as but not limited to the signal sequence of the immunoglobulin kappa and lambda light chain proteins. Further, the disclosure should not be construed to be limited to the polypeptides described herein, but also includes polypeptides comprising any enzymatically active truncation of the ENPP1 extracellular domain.

ENPP1 is made soluble by omitting the transmembrane domain. Human ENPP1 (SEQ ID NO:1) was modified to express a soluble, recombinant protein by replacing its transmembrane region (e.g., residues 77-98) with the corresponding subdomain of human ENPP2 (NCBI accession NP_00112433 5, e.g., residues 12-30). The modified ENPP1 sequence was cloned into a modified pFastbac FIT vector possessing a TEV protease cleavage site followed by a C-terminus 9-F1IS tag, and cloned and expressed in insect cells, and both proteins were expressed in a baculovirus system as described previously (Albright, et al., 2012, Blood 120:4432-4440; Saunders, et al., 2011, J. Biol. Chem. 18:994-1004; Saunders, et al., 2008, Mol. Cancer Ther. 7:3352-3362), resulting in the accumulation of soluble, recombinant protein in the extracellular fluid.

Production and Purification of ENPP1 and ENPP1 Fusion Proteins

In certain embodiments, a soluble ENPP1 polypeptide, including IgG Fc domain or enzymatically/biologically active fragments thereof, are efficacious in treating, reducing, and/or preventing progression of diseases or disorders contemplated herein. In other embodiments, the soluble ENPP1 polypeptide does not include a bone targeting domain, such as 2-20 consecutive polyaspartic acid residues or 2-20 consecutive polyglutamic acid residues.

To produce soluble, recombinant ENPP1 for in vitro use, ENPP1 was fused to the Fc domain of IgG (referred to as "NPP1-Fc") and the fusion protein was expressed in stable CHO cell lines. The protein can also be expressed from HEK293 cells, Baculovirus insect cell system or CHO cells or Yeast *Pichia* expression system using suitable vectors. The protein can be produced in either adherent or suspension cells. Preferably the fusion protein is expressed in CHO cells. To establish stable cell lines the nucleic acid sequence encoding ENPP1 constructs are cloned into an appropriate vector for large scale protein production.

Many expression systems are known can be used for the production of ENPP1 fusion protein, including bacteria (for example *E. coli* and *Bacillus subtilis*), yeasts (for example *Saccharomyces cerevisiae, Kluyveronmyces lactis* and *Pichia pastoris*), filamentous fungi (for example *Aspergillus*), plant cells, animal cells and insect cells. The desired protein can be produced in conventional ways, for example from a coding sequence inserted in the host chromosome or on a free plasmid.

The yeasts can be transformed with a coding sequence for the desired protein in any of the usual ways, for example electroporation. Methods for transformation of yeast by electroporation are disclosed in Becker & Guarente, 1990, Methods Enzymol. 194:182. Successfully transformed cells, i.e., cells that contain a DNA construct of the present disclosure, can be identified by well-known techniques. For example, cells resulting from the introduction of an expression construct can be grown to produce the desired polypeptide. Cells can be harvested and lysed and their DNA content examined for the presence of the DNA using a method, such as that described by Southern, 1975, J. Mol. Biol, 98:503 and/or Berent, et al., 1985, Biotech 3:208. Alternatively, the presence of the protein in the supernatant can be detected using antibodies.

Useful yeast plasmid vectors include pRS403-406 and pRS413-416 and are generally available fron1 Strat: 1.gene Cloning Systems, La Jolla, CA, USA Plasmids pRS403, pRS404, pRS405 and pRS406 are Yeast Integrating plasmids (Y1ps) and incorporate the yeast selectable markers I-11S3, TRP1, LEU2 and 1JRA3. Plasmids pRS413-416 are Yeast Centromere plasmids (YCps).

A variety of methods have been developed to operably link DNA to vectors via complementary cohesive termini. For instance, complementary homopolymer tract can be added to the DNA segment to be inserted to the vector DNA. The vector and DNA segment are then joined by hydrogen bonding between the complementary homopolymeric tails to form recombinant DNA molecules.

Synthetic linkers containing one or more restriction sites provide an alternative method of joining the DNA segment to vectors. The DNA segment, generated by endonuclease restriction digestion, is treated with bacteriophage T4 DNA polymerase or *E. coli* DNA polymerase I, which are enzymes that remove protruding, 3'-single-stranded termini with their 3'-5'-exonucleolytic activities, and fill in recessed 3'-ends with their polymerizing activities.

The combination of these activities thus generates blunt-ended DNA segments. The blunt-ended segments are then incubated with a large molar excess of linker molecules in the presence of an enzyme that is able to catalyze the ligation of blunt-ended DNA molecules, such as bacteriophage T4 DNA ligase. Thus, the products of the reaction are DNA segments carrying polymeric linker sequences at their ends. These DNA segments are then cleaved with the appropriate restriction enzyme and ligated to an expression vector that has been cleaved with an enzyme that produces termini compatible with those of the DNA segment.

Clones of single, stably transfected cells are then established and screened for high expressing clones of the desired fusion protein. Screening of the single cell clones for ENPP1 protein expression can be accomplished in a high-throughput manner in 96 well plates using the synthetic enzymatic substrate pNP-TMP as previously described (Albright, et al., 2015, Nat. Commun. 6:10006). Upon identification of high expressing clones through screening, protein production can be accomplished in shaking flasks or bio-reactors are previously described in Albright, et al., 2015, Nat. Commun. 6:10006.

Purification of ENPP1 can be accomplished using a combination of standard purification techniques known in the art. Examples of which are described above in production of ENPP1 protein. Following purification, ENPP1-Fc was dialyzed into PBS supplemented with $Zn^{2+}$ and $Mg^{2+}$ (PBSplus) concentrated to between 5 and 7 mg/ml, and frozen at −80° C. in aliquots of 200-500 µl. Aliquots were thawed immediately prior to use and the specific activity of the solution was adjusted to 31.25 au/ml (or about 0.7 mg/ml depending on the preparation) by dilution in PBSplus.

Gene Therapy

The nucleic acids encoding the polypeptide(s) useful within the disclosure may be used in gene therapy protocols for the treatment of the diseases or disorders contemplated herein. The improved construct encoding the polypeptide(s) can be inserted into the appropriate gene therapy vector and administered to a patient to treat or prevent the diseases or disorder of interest.

Vectors, such as viral vectors, have been used in the prior art to introduce genes into a wide variety of different target cells. Typically the vectors are exposed to the target cells so that transformation can take place in a sufficient proportion of the cells to provide a useful therapeutic or prophylactic effect from the expression of the desired polypeptide (e.g., a receptor). The transfected nucleic acid may be permanently incorporated into the genome of each of the targeted cells, providing long lasting effect, or alternatively the treatment may have to be repeated periodically. In certain embodiments, the (viral) vector transfects liver cells in vivo with genetic material encoding the polypeptide(s) of the disclosure.

A variety of vectors, both viral vectors and plasmid vectors are known in the art (see for example U.S. Pat. No. 5,252,479 and WO 93/07282). In particular, a number of viruses have been used as gene transfer vectors, including papovaviruses, such as SV40, vaccinia virus, herpes viruses including HSV and EBV, and retroviruses. Many gene therapy protocols in the prior art have employed disabled murine retroviruses. Several recently issued patents are directed to methods and compositions for performing gene therapy (see for example U.S. Pat. Nos. 6,168,916; 6,135,976; 5,965,541 and 6,129,705). Each of the foregoing patents is incorporated by reference in its entirety herein.

AAV-Mediated Gene Therapy:

AAV, a parvovirus belonging to the genus Dependovirus, has several features that make it particularly well suited for gene therapy applications. For example, AAV can infect a wide range of host cells, including non-dividing cells. Furthermore, AAV can infect cells from a variety of species. Importantly, AAV has not been associated with any human or animal disease, and does not appear to alter the physiological properties of the host cell upon integration. Finally, AAV is stable at a wide range of physical and chemical conditions, which lends itself to production, storage, and transportation requirements.

The AAV genome, which is a linear, single-stranded DNA molecule containing approximately 4,700 nucleotides (the AAV-2 genome consists of 4,681 nucleotides, the AAV-4 genome 4,767), generally comprises an internal non-repeating segment flanked on each end by inverted terminal repeats (ITRs). The ITRs are approximately 145 nucleotides in length (AAV-1 has ITRs of 143 nucleotides) and have multiple functions, including serving as origins of replication, and as packaging signals for the viral genome.

The internal non-repeated portion of the genome includes two large open reading frames (ORFs), known as the AAV replication (rep) and capsid (cap) regions. These ORFs encode replication and capsid gene products, which allow for the replication, assembly, and packaging of a complete AAV virion. More specifically, a family of at least four viral proteins are expressed from the AAV rep region: Rep 78, Rep 68, Rep 52, and Rep 40, all of which are named for their apparent molecular weights. The AAV cap region encodes at least three proteins: VP1, VP2, and VP3.

AAV is a helper-dependent virus, that is, it requires co-infection with a helper virus (e.g., adenovirus, herpesvirus, or vaccinia virus) in order to form functionally complete AAV virions. In the absence of co-infection with a helper virus, AAV establishes a latent state in which the viral genome inserts into a host cell chromosome or exists in an episomal form, but infectious virions are not produced. Subsequent infection by a helper virus "rescues" the integrated genome, allowing it to be replicated and packaged into viral capsids, thereby reconstituting the infectious virion. While AAV can infect cells from different species, the helper virus must be of the same species as the host cell. Thus, for example, human AAV replicates in canine cells that have been co-infected with a canine adenovirus.

To produce infectious recombinant AAV (rAAV) containing a heterologous nucleic acid sequence, a suitable host cell line can be transfected with an AAV vector containing the heterologous nucleic acid sequence, but lacking the AAV helper function genes, rep and cap. The AAV-helper function genes can then be provided on a separate vector. Also, only the helper virus genes necessary for AAV production (i.e., the accessory function genes) can be provided on a vector, rather than providing a replication-competent helper virus (such as adenovirus, herpesvirus, or vaccinia).

Collectively, the AAV helper function genes (i.e., rep and cap) and accessory function genes can be provided on one or more vectors. Helper and accessory function gene products can then be expressed in the host cell where they will act in trans on rAAV vectors containing the heterologous nucleic acid sequence. The rAAV vector containing the heterologous nucleic acid sequence will then be replicated and packaged as though it were a wild-type (wt) AAV genome, forming a recombinant virion. When a patient's cells are infected with the resulting rAAV virions, the heterologous nucleic acid sequence enters and is expressed in the patient's cells. Because the patient's cells lack the rep and cap genes, as well as the accessory function genes, the rAAV cannot further replicate and package their genomes. Moreover, without a source of rep and cap genes, wtAAV cannot be formed in the patient's cells.

There are eleven known AAV serotypes, AAV-1 through AAV-11 (Mori, et al., 2004, Virology 330 (2): 375-83). AAV-2 is the most prevalent serotype in human populations; one study estimated that at least 80% of the general population has been infected with wt AAV-2 (Berns and Linden, 1995, Bioessays 17:237-245). AAV-3 and AAV-5 are also prevalent in human populations, with infection rates of up to 60% (Georg-Fries, et al., 1984, Virology 134:64-71). AAV-1 and AAV-4 are simian isolates, although both serotypes can transduce human cells (Chiorini, et al., 1997, J Virol 71:6823-6833; Chou, et al., 2000, Mol Ther 2:619-623). Of the six known serotypes, AAV-2 is the best characterized. For instance, AAV-2 has been used in a broad array of in vivo transduction experiments, and has been shown to transduce many different tissue types including: mouse (U.S. Pat. Nos. 5,858,351; 6,093,392), dog muscle; mouse liver (Couto, et al., 1999, Proc. Natl. Acad. Sci. USA 96:12725-12730; Couto, et al., 1997, J. Virol. 73:5438-5447; Nakai, et al., 1999, J. Virol. 73:5438-5447; and, Snyder, et al., 1997, Nat. Genet. 16:270-276); mouse heart (Su, et al., 2000, Proc. Natl. Acad. Sci. USA 97:13801-13806); rabbit lung (Flotte, et al., 1993, Proc. Natl. Acad. Sci. USA 90:10613-10617);

and rodent photoreceptors (Flannery et al., 1997, Proc. Natl. Acad. Sci. USA 94:6916-6921).

The broad tissue tropism of AAV-2 may be exploited to deliver tissue-specific transgenes. For example, AAV-2 vectors have been used to deliver the following genes: the cystic fibrosis transmembrane conductance regulator gene to rabbit lungs (Flotte, et al., 1993, Proc. Natl. Acad. Sci. USA 90:10613-10617); Factor NIII gene (Burton, et al., 1999, Proc. Natl. Acad. Sci. USA 96:12725-12730) and Factor IX gene (Nakai, et al., 1999, J. Virol. 73:5438-5447; Snyder, et al., 1997, Nat. Genet. 16:270-276; U.S. Pat. No. 6,093,392) to mouse liver, dog, and mouse muscle (U.S. Pat. No. 6,093,392); erythropoietin gene to mouse muscle (U.S. Pat. Nos. 5,858,351); vascular endothelial growth factor (VEGF) gene to mouse heart (Su, et al., 2000, Proc. Natl. Acad. Sci. USA 97:13801-13806); and aromatic 1-amino acid decarboxylase gene to monkey neurons. Expression of certain rAAV-delivered transgenes has therapeutic effect in laboratory animals; for example, expression of Factor IX was reported to have restored phenotypic normalcy in dog models of hemophilia B (U.S. Pat. No. 6,093,392). Moreover, expression of rAAV-delivered NEGF to mouse myocardium resulted in neovascular formation (Su, et al., 2000, Proc. Natl. Acad. Sci. USA 97:13801-13806), and expression of rAAV-delivered AADC to the brains of parkinsonian monkeys resulted in the restoration of dopaminergic function.

Delivery of a protein of interest to the cells of a mammal is accomplished by first generating an AAV vector comprising DNA encoding the protein of interest and then administering the vector to the mammal. Thus, the disclosure should be construed to include AAV vectors comprising DNA encoding the polypeptide(s) of interest. Once armed with the present disclosure, the generation of AAV vectors comprising DNA encoding this/these polypeptide(s) s will be apparent to the skilled artisan.

In certain embodiments, the rAAV vector of the disclosure comprises several essential DNA elements. In certain embodiments, these DNA elements include at least two copies of an AAV ITR sequence, a promoter/enhancer element, a transcription termination signal, any necessary 5' or 3' untranslated regions which flank DNA encoding the protein of interest or a biologically active fragment thereof. The rAAV vector of the disclosure may also include a portion of an intron of the protein on interest. Also, optionally, the rAAV vector of the disclosure comprises DNA encoding a mutated polypeptide of interest.

In certain embodiments, the vector comprises a promoter/regulatory sequence that comprises a promiscuous promoter which is capable of driving expression of a heterologous gene to high levels in many different cell types. Such promoters include, but are not limited to the cytomegalovirus (CMV) immediate early promoter/enhancer sequences, the Rous sarcoma virus promoter/enhancer sequences and the like. In certain embodiments, the promoter/regulatory sequence in the rAAV vector of the disclosure is the CMV immediate early promoter/enhancer. However, the promoter sequence used to drive expression of the heterologous gene may also be an inducible promoter, for example, but not limited to, a steroid inducible promoter, or may be a tissue specific promoter, such as, but not limited to, the skeletal α-actin promoter which is muscle tissue specific and the muscle creatine kinase promoter/enhancer, and the like.

In certain embodiments, the rAAV vector of the disclosure comprises a transcription termination signal. While any transcription termination signal may be included in the vector of the disclosure, in certain embodiments, the transcription termination signal is the SV40 transcription termination signal.

In certain embodiments, the rAAV vector of the disclosure comprises isolated DNA encoding the polypeptide of interest, or a biologically active fragment of the polypeptide of interest. The disclosure should be construed to include any mammalian sequence of the polypeptide of interest, which is either known or unknown. Thus, the disclosure should be construed to include genes from mammals other than humans, which polypeptide functions in a substantially similar manner to the human polypeptide. Preferably, the nucleotide sequence comprising the gene encoding the polypeptide of interest is about 50% homologous, more preferably about 70% homologous, even more preferably about 80% homologous and most preferably about 90% homologous to the gene encoding the polypeptide of interest.

Further, the disclosure should be construed to include naturally occurring variants or recombinantly derived mutants of wild type protein sequences, which variants or mutants render the polypeptide encoded thereby either as therapeutically effective as full-length polypeptide, or even more therapeutically effective than full-length polypeptide in the gene therapy methods of the disclosure.

The disclosure should also be construed to include DNA encoding variants which retain the polypeptide's biological activity. Such variants include proteins or polypeptides which have been or may be modified using recombinant DNA technology, such that the protein or polypeptide possesses additional properties which enhance its suitability for use in the methods described herein, for example, but not limited to, variants conferring enhanced stability on the protein in plasma and enhanced specific activity of the protein. Analogs can differ from naturally occurring proteins or peptides by conservative amino acid sequence differences or by modifications which do not affect sequence, or by both. For example, conservative amino acid changes may be made, which although they alter the primary sequence of the protein or peptide, do not normally alter its function.

The disclosure is not limited to the specific rAAV vector exemplified in the experimental examples; rather, the disclosure should be construed to include any suitable AAV vector, including, but not limited to, vectors based on AAV-1, AAV-3, AAV-4 and AAV-6, and the like.

Also included in the disclosure is a method of treating a mammal having a disease or disorder in an amount effective to provide a therapeutic effect. The method comprises administering to the mammal an rAAV vector encoding the polypeptide of interest. Preferably, the mammal is a human.

Typically, the number of viral vector genomes/mammal which are administered in a single injection ranges from about $1\times10^{8}$ to about $5\times10^{16}$. Preferably, the number of viral vector genomes/mammal which are administered in a single injection is from about $1\times10^{10}$ to about $1\times10^{15}$; more preferably, the number of viral vector genomes/mammal which are administered in a single injection is from about $5\times10^{10}$ to about $5\times10^{15}$; and, most preferably, the number of viral vector genomes which are administered to the mammal in a single injection is from about $5\times10^{11}$ to about $5\times10^{14}$.

When the method of the disclosure comprises multiple site simultaneous injections, or several multiple site injections comprising injections into different sites over a period of several hours (for example, from about less than one hour to about two or three hours) the total number of viral vector genomes administered may be identical, or a fraction thereof or a multiple thereof, to that recited in the single site injection method.

For administration of the rAAV vector of the disclosure in a single site injection, in certain embodiments a composition comprising the virus is injected directly into an organ of the subject (such as, but not limited to, the liver of the subject).

For administration to the mammal, the rAAV vector may be suspended in a pharmaceutically acceptable carrier, for example, HEPES buffered saline at a pH of about 7.8. Other useful pharmaceutically acceptable carriers include, but are not limited to, glycerol, water, saline, ethanol and other pharmaceutically acceptable salt solutions such as phosphates and salts of organic acids. Examples of these and other pharmaceutically acceptable carriers are described in Remington's Pharmaceutical Sciences (1991, Mack Publication Co., New Jersey).

The rAAV vector of the disclosure may also be provided in the form of a kit, the kit comprising, for example, a freeze-dried preparation of vector in a dried salts formulation, sterile water for suspension of the vector/salts composition and instructions for suspension of the vector and administration of the same to the mammal.

SEQUENCES

SEQ ID NO: 1: hENPP1 Amino Acid Sequence
MERDGCAGGGSRGGEGGRAPREGPAGNGRDRGRSHAAEAPGDPQAAASLLAPMDVGEEPLEK
AARARTAKDPNTYKVLSLVLSVCVLTTILGCIFGLKPSCAKEVKSCKGRCFERTFGNCRCDA
ACVELGNCCLDYQETCIEPEHIWTCNKFRCGEKRLTRSLCACSDDCKDKGDCCINYSSVCQG
EKSWVEEPCESINEPQCPAGFETPPTLLFSLDGFRAEYLHTWGGLLPVISKLKKCGTYTKNM
RPVYPTKTFPNHYSIVTGLYPESHGIIDNKMYDPKMNASFSLKSKEKFNPEWYKGEPIWVTA
KYQGLKSGTFFWPGSDVEINGIFPDIYKMYNGSVPFEERILAVLQWLQLPKDERPHFYTLYL
EEPDSSGHSYGPVSSEVIKALQRVDGMVGMLMDGLKELNLHRCLNLILISDHGMEQGSCKKY
IYLNKYLGDVKNIKVIYGPAARLRPSDVPDKYYSFNYEGIARNLSCREPNQHFKPYLKHFLP
KRLHFAKSDRIEPLTFYLDPQWQLALNPSERKYCGSGFHGSDNVFSNMQALFVGYGPGFKHG
IEADTFENIEVYNLMCDLLNLTPAPNNGTHGSLNHLLKNPVYTPKHPKEVHPLVQCPFTRNP
RDNLGCSCNPSILPIEDFQTQFNLTVAEEKIIKHETLPYGRPRVLQKENTICLLSQHQFMSG
YSQDILMPLWTSYTVDRNDSFSTEDFSNCLYQDFRIPLSPVHKCSFYKNNTKVSYGFLSPPQ
LNKNSSGIYSEALLTTNIVPMYQSFQVIWRYFHDTLLRKYAEERNGVNVVSGPVFDFDYDGR
CDSLENLRQKRRVIRNQEILIPTHFFIVLTSCKDTSQTPLHCENLDTLAFILPHRTDNSESC
VHGKHDSSWVEELLMLHRARITDVEHITGLSFYQQRKEPVSDILKLKTHLPTFSQED SEQ ID NO: 2: ENPP2 Amino Acid Sequence
MARRSSFQSCQIISLFTFAVGVNICLGFTAHRIKRAEGWEEGPPTVLSDSPWTNISGSCKGR
CFELQEAGPPDCRCDNLCKSYTSCCHDFDELCLKTARGWECTKDRCGEVRNEENACHCSEDC
LARGDCCTNYQVVCKGESHWVDDDCEEIKAAECPAGFVRPPLIIFSVDGFRASYMKKGSKVM
PNIEKLRSCGTHSPYMRPVYPTKTFPNLYTLATGLYPESHGIVGNSMYDPVFDATFHLRGRE
KFNHRWWGGQPLWITATKQGVKAGTFFWSVVIPHERRILTILQWLTLPDHERPSVYAFYSEQ
PDFSGHKYGPFGPEMTNPLREIDKIVGQLMDGLKQLKLHRCVNVIFVGDHGMEDVTCDRTEF
LSNYLINVDDITLVPGTLGRIRSKFSNNAKYDPKAIIANLICKKPDQHFKPYLKQHLPKRLH
YANNRRIEDIHLLVERRWHVARKPLDVYKKPSGKCFFQGDHGFDNKVNSMQTVFVGYGSTFK
YKTKVPPFENIELYNVMCDLLGLKPAPNNGTHGSLNHLLRTNTFRPTMPEEVTRPNYPGIMY
LQSDFDLGCTCDDKVEPKNKLDELNKRLHTKGSTEAETRKFRGSRNENKENINGNFEPRKER
HLLYGRPAVLYRTRYDILYHTDFESGYSEIFLMPLWTSYTVSKQAEVSSVPDHLTSCVRPDV
RVSPSFSQNCLAYKNDKQMSYGFLFPPYLSSSPEAKYDAFLVTNMVPMYPAFKRVWNYFQRV
LVKKYASERNGVNVISGPIFDYDYDGLHDTEDKIKQYVEGSSIPVPTHYYSIITSCLDFTQP
ADKCDGPLSVSSFILPHRPDNEESCNSSEDESKWVEELMKMHTARVRDIEHLTSLDFFRKTS
RSYPEILTLKTYLHTYESEI SEQ ID NO: 3 hIgG Fc domain, Fc
DKTHTCPPCPAPELLGGPSVFLFPPKPKDTLMISRTPEVTCVVVDVSHEDPEVKFNWYVDGV
EVHNAKTKPREEQYNSTYRVVSVLTVLHQDWLNGKEYKCKVSNKALPAPIEKTISKAKGQPR
EPQVYTLPPSREEMTKNQVSLTCLVKGFYPSDIAVEWESNGQPENNYKTTPPVLDSDGSFFL
YSKLTVDKSRWQQGNVFSCSVMHEALHNHYTQKSLSLSPGK SEQ ID NO: 4: hENPP5 protein export signal sequence
MTSKFLLVSFILAALSLSTTFS-$Xaa_{23}Xaa_{24}$,
wherein $Xaa_{23}$ is absent or L, and
wherein $Xaa_{24}$ is absent if $Xaa_{23}$ is absent and $Xaa_{24}$ is absent or Q if $Xaa_{23}$ is L SEQ ID NO: 5: hENPP7 protein export signal sequence
MRGPAVLLTV ALATLLAPGA GA SEQ ID NO: 6: hENPP7 protein export signal sequence
MRGPAVLLTV ALATLLAPGA SEQ ID NO: 7: ENPP1-Fc
MRGPAVLLTVALATLLAPGAGAPSCAKEVKSCKGRCFERTFGNCRCDAAEVELGNCCLDYQE
TCIEPEHIWTCNKFRCGEKRLTRSLCACSDDCKDKGDCCINYSSVCQGEKSWVEEPCESINE
PQCPAGFETPPTLLFSLDGFRAEYLHTWGGLLPVISKLKKCGTYTKNMRPVYPTKTFPNHYS
IVTGLYPESHGIIDNKMYDPKMNASFSLKSKEKFNPEWYKGEPIWVTAKYQGLKSGTFFWPG
SDVEINFIFPDIYKMYNGSVPFEERILAVLQWLQLPKDERPHFYTLYLEEPDSSGHSYGPVS
SEVIKALQRVDGMVGMLMDGLKELNLHRCLNLILISDHGMEQGSCKKYIYLNKYLGDVKNIK
VIYGPAARLRPSDVPDKYYSFNYEGIARNLSCREPNQHFKPYLKHFLPKRLHFAKSDRIEPL
TFYLDPQWQLALNPSERKYCGSGFHGSDNVFSNMQALFVGYGPGFKHGIEADTFENIEVYNL
MCDLLNLTPAPNNGTHGELNHLLKNPVYTPKHPKEVHPLVQCPFTRNPRDNLGCSCNPSILP
IEDFQTQFNLTVAEEKIIKHETLPYGRPRVLQKENTICLLSQHQFMSGYSQDILMPLWTSYT
VDRNDSFSTEDFSNCLYQDFRIPLSPVHKCSFYKNNTKVSYGFLSPPQLNKNSSGIYSEALL
TTNIVPMYQSFQVIWRYFHDTLLRKYAEERNGVNVVSGPVFDFDYDGRCDSLENLRQKRRVI
RNQEILIPTHFFIVLTSCKDTSQTPLHCENLDTLAFILPHRTDNSESCVHGKHDSSWVEELL -continued

SEQUENCES

MLHRARITDVEHITGLSFYQQRKEPVSDILKLKTHLPTFSQED*RSDKTHTCPPCPAPELLGG*
*PSVFLFPPKPKDTLMISRTPEVTCVVVDVSREDPEVKFNWYVDGVEVHNAKTKPREEQYNST*
*YRVVSVLTVLHQDWLNGKEYKCKVSNEALPAPIEKTISKAKGQPREPQVYTLPPSREEMTKN*
*QVSLTCLVKGFYPSDIAVEWESNGQPENNYKTTPPVLDSDGSFFLYSKLTVDKSRWQQGNVF*
*SCSVMEEALHNHYTQKSLSLSPGK*

Bold: signal sequence
Regular: ENPP1 extracellular domain
Underlined: linker sequence
Italics: Fc domain SEQ ID NO: 8: Exemplary Amino Acid Linker Sequence
LIN SEQ ID NO: 9: Exemplary Amino Acid Linker Sequence
$(GGGGS)_n$
n is an integer between and including 1 and 10, e.g., n = 1, n = 2, n = 3, n = 4, n = 5, n = 6, n = 7, n = 8, n = 9, or n = 10.

SEQ ID NO: 10: Exemplary Extracellular Domain of human ENPP1
PSCAKEVKSCKGRCFERTFGNCRCDAACVELGNCCLDYQETCIEPEHIWTCNKFRCGEKRLT
RSLCACSDDCKDKGDCCINYSSVCQGEKSWVEEPCESINEPQCPAGFETPPTLLFSLDGFRA
EYLHTWGGLLPVISKLKKCGTYTKNMRPVYPTKTFPNHYSIVTGLYPESHGIIDNKMYDPKM
NASFSLKSKEKFNPEWYKGEPIWVTAKYQGLKSGTFFWPGSDVEINGIFPDIYKMYNGSVPF
EERILAVLQWLQLPKDERPHFYTLYLEEPDSSGHSYGPVSSEVIKALQRVDGMVGMLMDGLK
ELNLHRCLNLILISDHGMEQGSCKKYIYLNKYLGDVKNIKVIYGPAARLRPSDVPDKYYSFN
YEGIARNLSCREPNQHFKPYLKHFLPKRLHFAKSDRIEPLTFYLDPQWQLALNPSERKYCGS
GFHGSDNVFSNMQALFVGYGPGFKHGIEADTFENIEVYNLMCDLLNLTPAPNNGTHGSLNHL
LKNPVYTPKHPKEVHPLVQCPFTRNPRDNLGCSCNPSILPIEDFQTQFNLTVAEEKIIKHET
LPYGRPRVLQKENTICLLSQHQFMSGYSQDILMPLWTSYTVDRNDSFSTEDFSNCLYQDFRI
PLSPVHKCSFYKNNTKVSYGFLSPPQLNKNSSGIYSEALLTTNIVPMYQSFQVIWRYFHDTL
LRKYAEERNGVNVVSGPVFDFDYDGRCDSLENLRQKRRVIRNQEILIPTHFFIVLTSCKDTS
QTPLHCENLDTLAFILPHRTDNSESCVHGKHDSSWVEELLMLHRARITDVEHITGLSFYQQR
KEPVSDILKLKTHLPTFSQED SEQ ID NO: 11: Exemplary ENPP1 Mutant Polypeptide (substitutions relative to wildtype human ENPP1 are shown in bold/underline)

PSCAKEVKSCKGRCFERTFGNCRCDAACVELGNCCLDYQETCIEPEHIWTCNKFRCGEKRLT
RSLCACSDDCKDKGDCCINYSSVCQGEKSWVEEPCESINEPQCPAGFETPPTLLFSLDGFRA
EYLHTWGGLLPVISKLKKCGTYTKNMRPVYPTKTFPNHYSIVTGLYPESHGIIDNKMYDPKM
NASFSLKSKEKFNPEWYKGEPIWVTAKYQGLKSGTFFWPGSDVEINGTFPDIYKMYNGSVPF
EERILAVLQWLQLPKDERPHFYTLYLEEPDSSGHSYGPVSSEVIKALQRVDGMVGMLMDGLK
ELNLHRCLNLILISDHGMEQGSCKKYIYLNKYLGDVKNIKVIYGPAARLRPSDVPDKYYSFN
YEGIARNLSCREPNQHFKPYLKHFLPKRLHFAKSDRIEPLTFYLDPQWQLALNPSERKYCGS
GFHGSDNVFSNMQALFVGYGPGFKHGIEADTFENIEVYNLMCDLLNLTPAPNNGTHGSLNHL
LKNPVYTPKHPKEVHPLVQCPFTRNPRDNLGCSCNPSILPIEDFQTQFNLTVAEEKIIKHET
LPYGRPRVLQKENTICLLSQHQFMSGYSQDILMPLWTSYTVDRNDSFSTEDFSNCLYQDFRI
PLSPVHKCSFYKNNTKVSYGFLSPPQLNKNSSGIYSEALLTTNIVPMYQSFQVIWRYFHDTL
LRKYAEERNGVNVVSGPVFDFDYDGRCDSLENLRQKRRVIRNQEILIPTHFFIVLTSCKDTS
QTPLHCENLDTLAFILPHRTDNSESCVHGKHDSSWVEELLMLHRARITDVEHITGLSFYQQR
KEPVSDILKLKTHLPTFSQED

SEQ ID NO: 12: Exemplary ENPP1 Mutant Polypeptide (substitutions relative to wildtype human ENPP1 are shown in bold/underline)
PSCAKENKSCKGRCFERTFGNCRCDAACVELGNCCLDYQETCIEPEHIWTCNKFRCGEKRLT
RSLCACSDDCKDKGDCCINYSSVCQGEKSWVEEPCESINEPQCPAGFETPPTLLFSLDGFRA
EYLHTWGGLLPVISKLKKCGTYTKNMRPVYPTKTFPNHYSIVTGLYPESHGIIDNKMYDPKM
NASFSLKSKEKFNPEWYKGEPIWVTAKYQGLKSGTFFWPGSDVEINGTFPDIYKMYNGSVPF
EERILAVLQWLQLPKDERPHFYTLYLEEPDSSGHSYGPVSSEVIKALQRVDGMVGMLMDGLK
ELNLHRCLNLILISDHGMEQGSCKKYIYLNKYLGDVKNIKVIYGPAARLRPSDVPDKYYSFN
YEGIARNLSCREPNQHFKPYLKHFLPKRLHFAKSDRIEPLTFYLDPQWQLALNPSERKYCGS
GFHGSDNVFSNMQALFVGYGPGFKHGIEADTFENIEVYNLMCDLLNLTPAPNNGTHGSLNHL
LKNPVYTPKHPKEVHNLTQCPFTRNPRDNLGCSCNPSILPIEDFQTQFNLTVAEEKIIKHET
LPYGRPRVLQKENTICLLSQHQFMSGYSQDILMPLWTSYTVDRNDSFSTEDFSNCLYQDFRI
PLSPVHKCSFYKNNTKVSYGFLSPPQLNKNSSGIYSEALLTTNIVPMYQSFQVIWRYFHDTL
LRKYAEERNGVNVVSGPVFDFDYDGRCDSLENLRQKRRVIRNQEILIPTHFFIVLTSCKDTS
QTPLHCENLDTLAFILPHRTDNSESCVHGKHDSSWVEELLMLHRARITDVEHITGLSFYQQR
KEPVSDILKLKTHLPTFSQED SEQ ID NO: 13: Exemplary Human IgG1 Fc Region
DKTHTCPPCPAPELLGGPSVFLFPPKPKDTLMISRTPEVTCVVVDVSHEDPEVKFNWYVDGV
EVHNAKTKPREEQYNSTYRVVSVLTVLHQDWLNGKEYKCKVSNKALPAPIEKTISKAKGQPR
EPQVYTLPPSREEMTKNQVSLTCLVKGFYPSDIAVEWESNGQPENNYKTTPPVLDSDGSFFL
YSKLTVDKSRWQQGNVFSCSVMHEALHNHYTQKSLSLSPGK -continued

SEQUENCES

SEQ ID NO: 14: Exemplary Variant Human IgG1 Fc Region (containing the MST/YTE Substitutions (bold/underline))
DKTHTCPPCPAPELLGGPSVFLFPPKPKDTLYITREPEVTCVVVDVSHEDPEVKFNWYVDGV
EVHNAKTKPREEQYNSTYRVVSVLTVLHQDWLNGKEYKCKVSNKALPAPIEKTISKAKGQPR
EPQVYTLPPSREEMTKNQVSLTCLVKGFYPSDIAVEWESNGQPENNYKTTPPVLDSDGSFFL
YSKLTVDKSRWQQGNVFSCSVMHEALHNHYTQKSLSLSPGK SEQ ID NO: 15: Exemplary ENPP1-containing Fusion: ENPP1 extracellular domain (SEQ ID NO: 10; italics) fused at its C-terminus to $(GGGGS)_1$ (SEQ ID NO: 9 (n = 1); double underlined), which is fused at its C-terminus to a variant human IgG Fc Region (SEQ ID NO: 14; unmodified text)
*PSCAKEVKSCKGRCFERTFGNCRCDAACVELGNCCLDYQETCIEPEHIWTCNKFRCGEKRLT*
*RSLCACSDDCKDKGDCCINYSSVCQGEKSWVEEPCESINEPQCPAGFETPPTLLFSLDGFRA*
*EYLHTWGGLLPVISKLKKCGTYTKNMRPVYPTKTFPNHYSIVTGLYPESHGIIDNKMYDPKM*
*NASFSLKSKEKFNPEWYKGEPIWVTAKYQGLKSGTFFWPGSDVEINGIFPDIYKMYNGSVPF*
*EERILAVLQWLQLPKDERPHFYTLYLEEPDSSGHSYGPVSSEVIKALQRVDGMVGMLMDGLK*
*ELNLHRCLNLILISDHGMEQGSCKKYIYLNKYLGDVKNIKVIYGPAARLRPSDVPDKYYSFN*
YEGIARNLSCREPNQHFKPYLKHFLPKRLHFAKSDRIEPLTFYLDPQWQLALNPSERKYCGS
*GFHGSDNVFSNMQALFVGYGPGFKHGIEADTFENIEVYNLMCDLLNLTPAPNNGTHGSLNHL*
*LKNPVYTPKHPKEVHPLVQCPFTRNPRDNLGCSCNPSILPIEDFQTQFNLTVAEEKIIKHET*
*LPYGRPRVLQKENTICLLSQHQFMSGYSQDILMPLWTSYTVDRNDSFSTEDFSNCLYQDFRI*
*PLSPVHKCSFYKNNTKVSYGFLSPPQLNKNSSGIYSEALLTTNIVPMYQSFQVIWRYFHDTL*
*LRKYAEERNGVNVVSGPVFDFDYDGRCDSLENLRQKRRVIRNQEILIPTHFFIVLTSCKDTS*
*QTPLHCENLDTLAFILPHRTDNSESCVHGKHDSSWVEELLMLHRARITDVEHITGLSFYQQR*
*KEPVSDILKLKTHLPTFSQED*GGGGSDKTHTCPPCPAPELLGGPSVFLFPPKPKDTLYITRE
PEVTCVVVDVSHEDPEVKFNWYVDGVEVHNAKTKPREEQYNSTYRVVSVLTVLHQDWLNGKE
YKCKVSNKALPAPIEKTISKAKGQPREPQVYTLPPSREEMTKNQVSLTCLVKGFYPSDIAVE
WESNGQPENNYKTTPPVLDSDGSFFLYSKLTVDKSRWQQGNVFSCSVMHEALHNHYTQKSLS
LSPGK

| | |
|---|---|
| Italics: | ENPP1 extracellular domain |
| Doubly underlined: | linker sequence |
| Regular: | IgG Fc Region |

SEQ ID NO: 16: Exemplary ENPP1-containing Fusion: ENPP1 extracellular domain (SEQ ID NO: 10; italics) fused at its C-terminus to the amino acid sequence LIN (SEQ ID NO: 8; double underlined), which is fused at its C-terminus to a variant human IgG Fc Region (SEQ ID NO: 14; unmodified text)
*PSCAKEVKSCKGRCFERTFGNCRCDAACVELGNCCLDYQETCIEPEHIWTCNKFRCGEKRLT*
*RSLCACSDDCKDKGDCCINYSSVCQGEKSWVEEPCESINEPQCPAGFETPPTLLFSLDGFRA*
*EYLHTWGGLLPVISKLKKCGTYTKNMRPVYPTKTFPNHYSIVTGLYPESHGIIDNKMYDPKM*
*NASFSLKSKEKFNPEWYKGEPIWVTAKYQGLKSGTFFWPGSDVEINGIFPDIYKMYNGSVPF*
*EERILAVLQWLQLPKDERPHFYTLYLEEPDSSGHSYGPVSSEVIKALQRVDGMVGMLMDGLK*
*ELNLHRCLNLILISDHGMEQGSCKKYIYLNKYLGDVKNIKVIYGPAARLRPSDVPDKYYSFN*
*YEGIARNLSCREPNQHFKPYLKHFLPKRLHFAKSDRIEPLTFYLDPQWQLALNPSERKYCGS*
*GFHGSDNVFSNMQALFVGYGPGFKHGIEADTFENIEVYNLMCDLLNLTPAPNNGTHGSLNHL*
*LKNPVYTPKHPKEVHPLVQCPFTRNPRDNLGCSCNPSILPIEDFQTQFNLTVAEEKIIKHET*
*LPYGRPRVLQKENTICLLSQHQFMSGYSQDILMPLWTSYTVDRNDSFSTEDFSNCLYQDFRI*
*PLSPVHKCSFYKNNTKVSYGFLSPPQLNKNSSGIYSEALLTTNIVPMYQSFQVIWRYFHDTL*
*LRKYAEERNGVNVVSGPVFDFDYDGRCDSLENLRQKRRVIRNQEILIPTHFFIVLTSCKDTS*
*QTPLHCENLDTLAFILPHRTDNSESCVHGKHDSSWVEELLMLHRARITDVEHITGLSFYQQR*
*KEPVSDILKLKTHLPTFSQED*LINDKTHTCPPCPAPELLGGPSVFLFPPKPKDTLYITREPE
VTCVVVDVSHEDPEVKFNWYVDGVEVHNAKTKPREEQYNSTYRVVSVLTVLHQDWLNGKEYK
CKVSNKALPAPIEKTISKAKGQPREPQVYTLPPSREEMTKNQVSLTCLVKGFYPSDIAVEWE
SNGQPENNYKTTPPVLDSDGSFFLYSKLTVDKSRWQQGNVFSCSVMHEALHNHYTQKSLSLS
PGK

| | |
|---|---|
| Italics: | ENPP1 extracellular domain |
| Doubly underlined: | linker sequence |
| Regular: | IgG Fc Region |

SEQ ID NO: 17: Exemplary ENPP1 Mutant Polypeptide Fusion: ENPP1 Mutant Polypeptide (SEQ ID NO: 11; italics) fused at its C-terminus to LIN (SEQ ID NO: 8; double underlined), which is fused at its C-terminus to a variant human IgG Fc Region (SEQ ID NO: 14; unmodified text)
*PSCAKEVKSCKGRCFERTFGNCRCDAACVELGNCCLDYQETCIEPEHIWTCNKFRCGEKRLT*
*RSLCACSDDCKDKGDCCINYSSVCQGEKSWVEEPCESINEPQCPAGFETPPTLLFSLDGFRA*
*EYLHTWGGLLPVISKLKKCGTYTKNMRPVYPTKTFPNHYSIVTGLYPESHGIIDNKMYDPKM*
*NASFSLKSKEKFNPEWYKGEPIWVTAKYQGLKSGTFFWPGSDVEINGTFPDIYKMYNGSVPF*
*EERILAVLQWLQLPKDERPHFYTLYLEEPDSSGHSYGPVSSEVIKALQRVDGMVGMLMDGLK*
*ELNLHRCLNLILISDHGMEQGSCKKYIYLNKYLGDVKNIKVIYGPAARLRPSDVPDKYYSFN*
*YEGIARNLSCREPNQHFKPYLKHFLPKRLHFAKSDRIEPLTFYLDPQWQLALNPSERKYCGS*
*GFHGSDNVFSNMQALFVGYGPGFKHGIEADTFENIEVYNLMCDLLNLTPAPNNGTHGSLNHL*
*LKNPVYTPKHPKEVHPLVQCPFTRNPRDNLGCSCNPSILPIEDFQTQFNLTVAEEKIIKHET*
*LPYGRPRVLQKENTICLLSQHQFMSGYSQDILMPLWTSYTVDRNDSFSTEDFSNCLYQDFRI*
*PLSPVHKCSFYKNNTKVSYGFLSPPQLNKNSSGIYSEALLTTNIVPMYQSFQVIWRYFHDTL*
*LRKYAEERNGVNVVSGPVFDFDYDGRCDSLENLRQKRRVIRNQEILIPTHFFIVLTSCKDTS*
*QTPLHCENLDTLAFILPHRTDNSESCVHGKHDSSWVEELLMLHRARITDVEHITGLSFYQQR*

-continued

SEQUENCES

*KEPVSDILKLKTHLPTFSQED*LINDKTHTCPPCPAPELLGGPSVFLFPPKPKDTLYITREPE
VTCVVVDVSHEDPEVKFNWYVDGVEVHNAKTKPREEQYNSTYRVVSVLTVLHQDWLNGKEYK
CKVSNKALPAPIEKTISKAKGQPREPQVYTLPPSREEMTKNQVSLTCLVKGFYPSDIAVEWE
SNGQPENNYKTTPPVLDSDGSFFLYSKLTVDKSRWQQGNVFSCSVMHEALHNHYTQKSLSLS
PGK

SEQ ID NO: 18: Exemplary ENPP1 Mutant Polypeptide Fusion: ENPP1 Mutant Polypeptide (SEQ ID NO: 11; italics) fused at its C-terminus to $(GGGGS)_1$ (SEQ ID NO: 9, n = 1; double underlined), which is fused at its C-terminus to a variant human IgG Fc Region (SEQ ID NO: 14; unmodified text)

*PSCAKEVKSCKGRCFERTFGNCRCDAACVELGNCCLDYQETCIEPEHIWTCNKFRCGEK*
*RLTRSLCACSDDCKDKGDCCINYSSVCQGEKSWVEEPCESINEPQCPAGFETPPTLLFSLD*
*GFRAEYLHTWGGLLPVISKLKKCGTYTKNMRPVYPTKTFPNHYSIVTGLYPESHGIIDNKM*
*YDPKMNASFSLKSKEKENPEWYKGEPIWVTAKYQGLKSGTFFWPGSDVEINGTFPDIYKM*
*YNGSVPFEERILAVLQWLQLPKDERPHFYTLYLEEPDSSGHSYGPVSSEVIKALQRVDGMV*
*GMLMDGLKELNLHRCLNLILISDHGMEQGSCKKYIYLNKYLGDVKNIKVIYGPAARLRPSD*
*VPDKYYSFNYEGIARNLSCREPNQHFKPYLKHFLPKRLHFAKSDRIEPLTFYLDPQWQLAL*
*NPSERKYCGSGFHGSDNVFSNMQALFVGYGPGFKHGIEADTFENIEVYNLMCDLLNLTPA*
PNNGTHGSLNHLLKNPVYTPKHPKEVHPLVQCPFTRNPRDNLGCSCNPSILPIEDFQTQF
*NLTVAEEKIIKHETLPYGRPRVLQKENTICLLSQHQFMSGYSQDILMPLWTSYTVDRNDSFS*
*TEDFSNCLYQDFRIPLSPVHKCSFYKNNTKVSYGFLSPPQLNKNSSGIYSEALLTTNIVPMY*
*QSFQVIWRYFHDTLLRKYAEERNGVNVVSGPVFDFDYDGRCDSLENLRQKRRVIRNQEILI*
*PTHFFIVLTSCKDTSQTPLHCENLDTLAFILPHRTDNSESCVHGKHDSSWVEELLMLHRAR*
*ITDVEHITGLSFYQQRKEPVSDILKLKTHLPTFSQED*GGGGSDKTHTCPPCPAPELLGGP
SVFLFPPKPKDTLYITREPEVTCVVVDVSHEDPEVKFNWYVDGVEVHNAKTKPREEQ
YNSTYRVVSVLTVLHQDWLNGKEYKCKVSNKALPAPIEKTISKAKGQPREPQVYTLP
PSREEMTKNQVSLTCLVKGFYPSDIAVEWESNGQPENNYKTTPPVLDSDGSFFLYSK
LTVDKSRWQQGNVFSCSVMHEALHNHYTQKSLSLSPGK

Methods

The disclosure includes a method of reducing or preventing progression of pathological calcification in a subject in need thereof, the method comprising administering to the subject a therapeutically effective amount of a polypeptide of the disclosure.

The disclosure further includes a method of reducing or preventing progression of pathological ossification in a subject in need thereof, the method comprising administering to the subject a therapeutically effective amount of a polypeptide of the disclosure.

The disclosure further includes a method of reducing or preventing progression of ectopic calcification of soft tissue, including reducing, ameliorating, or preventing vascular calcification, in a subject in need thereof, the method comprising administering to the subject a therapeutically effective amount of a polypeptide of the disclosure.

The disclosure further includes a method of reducing or preventing progression of diseases caused by ENPP1 deficiency. ENPP1 deficiency is characterized by reduced levels of ENPP1 activity and or defective expression of ENPP1 levels (compared to that of ENPP1 activity levels or ENPP1 expression levels respectively in normal healthy subjects) in a subject in need thereof, the method comprising administering to the subject a therapeutically effective amount of a polypeptide of the disclosure.

The disclosure further includes a method of reducing or preventing progression of diseases caused by lower levels of plasma PPi in a subject in need thereof, the method comprising administering to the subject a therapeutically effective amount of the polypeptides of the disclosure to increase the plasma PPi of the subjects to normal (1-3 μM) or above (30-50% higher than) normal levels and then to maintain the plasma PPi at a constant normal or above normal level thereafter. The method further comprises administering additional therapeutic effective amounts at intervals of two days, three days, one week or one month in order to maintain the Plasma PPi of the subject at a constant normal or above normal level to reduce or prevent the progression of pathological calcification or ossification.

The disclosure further includes a method of treating, reversing, or preventing progression of ossification of the posterior longitudinal ligament (OPLL) in a subject in need thereof, the method comprising administering to the subject a therapeutically effective amount of a polypeptide of the disclosure.

The disclosure further includes a method of treating, reverting, or preventing progression of hypophosphatemic rickets in a subject in need thereof, the method comprising administering to the subject a therapeutically effective amount of a polypeptide of the disclosure.

The disclosure further includes a method of reducing or preventing progression of at least one disease selected from the group consisting of chronic kidney disease (CKD), end stage renal disease (ESRD), calcific uremic arteriolopathy (CUA), calciphylaxis, ossification of the posterior longitudinal ligament (OPLL), hypophosphatemic rickets, osteoarthritis, aging related hardening of arteries, idiopathic infantile arterial calcification (IIAC), Generalized Arterial Calcification of Infancy (GACI), and calcification of atherosclerotic plaques in a subject diagnosed with the at least one disease, the method comprising administering to the subject a therapeutically effective amount of a polypeptide of the disclosure.

The disclosure further includes a method of reducing or preventing progression of aging related hardening of arteries in a subject in need thereof, the method comprising administering to the subject a therapeutically effective amount of a polypeptide of the disclosure.

The disclosure further includes a method of reducing or preventing progression of a disease caused by ENPP1 deficiency (for example, reduced levels of ENPP1 activity and/or defective expression of ENPP1 levels, as compared to that of ENPP1 activity levels or ENPP1 expression levels, respectively, in normal healthy subjects) in a subject in need thereof, the method comprising administering to the subject a therapeutically effective amount of a polypeptide of the disclosure.

The disclosure further includes a method of reducing or preventing progression of a disease caused by lower than normal levels of plasma PPi in a subject in need thereof, the method comprising administering to the subject a therapeutically effective amount of a polypeptide of the disclosure to increase and/or sustain the plasma PPi of the subjects to a level that is about 90%, 95%, 100%, 105%, 110%, 120%, 130%, 140%, or 150% of the normal PPi level (about 1-3 μM). In certain embodiments, the method further comprises further administration of the polypeptide of the disclosure every two days, three days, one week, or one month in order to maintain the plasma PPi levels at a level that is about 90%, 95%, 100%, 105%, 110%, 120%, 130%, 140%, or 150% of the normal PPi level, thus preventing the progression of pathological calcification or ossification.

The disclosure further includes a method of treating, reversing, or preventing progression of Pseudoxanthoma Elasticum (PXE) in a subject in need thereof, the method comprising administering to the subject a therapeutically effective amount of a polypeptide of the disclosure.

The disclosure further includes a method of treating, reversing, or preventing progression of calcification of atherosclerotic plaques in vascular arteries in a subject in need thereof, the method comprising administering to the subject a therapeutically effective amount of a polypeptide of the disclosure.

The disclosure further includes a method of treating, reversing, or preventing progression of osteoarthritis in a subject in need thereof, the method comprising administering to the subject a therapeutically effective amount of a polypeptide of the disclosure.

The disclosure further includes a method of treating, reversing, or preventing progression of hardening of arteries due to progeria in a subject in need thereof, the method comprising administering to the subject a therapeutically effective amount of a polypeptide of the disclosure.

The disclosure further includes a method of treating, reversing, or preventing progression of X-linked hypophosphatemic rickets (XLH), hereditary hypophosphatemic rickets (HHRH), hypophosphatemic bone disease (HBD), autosomal dominant hypophosphatemic rickets (ADHR), and/or and autosomal recessive hypophosphatemic rickets in a subject in need thereof, the method comprising administering to the subject a therapeutically effective amount of a polypeptide of the disclosure.

The disclosure further includes a method of treating, reversing, or preventing progression of age-related osteopenia in a subject in need thereof, the method comprising administering to the subject a therapeutically effective amount of a polypeptide t of the disclosure.

The disclosure further includes a method of treating, reversing, or preventing progression of ankylosing spondylitis in a subject in need thereof, the method comprising administering to the subject a therapeutically effective amount of a polypeptide of the disclosure.

The disclosure further includes a method of treating, reversing, or preventing progression of strokes in pediatric sickle cell anemia in a subject in need thereof, the method comprising administering to the subject a therapeutically effective amount of a polypeptide of the disclosure.

The disclosure further includes a method of reducing or preventing progression of pathological calcification in a subject in need thereof, the method comprising administering to the subject a therapeutically effective amount of any one of the ENPP1 mutant polypeptides, fusions, ENPP-1 containing polypeptides, or conjugates described herein, to thereby reduce or prevent progression of pathological calcification in the subject.

The disclosure further includes a method of reducing or preventing progression of pathological ossification in a subject in need thereof, the method comprising administering to the subject a therapeutically effective amount of any one of the ENPP1 mutant polypeptides, fusions, ENPP-1 containing polypeptides, or conjugates described herein, to thereby reduce or prevent progression of pathological ossification in the subject.

The disclosure further includes a method of reducing or preventing progression of ectopic calcification of soft tissue in a subject in need thereof, the method comprising administering to the subject a therapeutically effective amount of any one of the ENPP1 mutant polypeptides, fusions, ENPP-1 containing polypeptides, or conjugates described herein, to thereby reduce or prevent progression of ectopic calcification of soft tissue in the subject.

The disclosure further includes a method of treating, reversing, or preventing progression of ossification of the posterior longitudinal ligament (OPLL) in a subject in need thereof, the method comprising administering to the subject a therapeutically effective amount of any one of the ENPP1 mutant polypeptides, fusions, ENPP-1 containing polypeptides, or conjugates described herein, to thereby reduce, reverse, or prevent ossification of the posterior longitudinal ligament (OPLL) in the subject.

The disclosure further includes a method of treating, reverting, or preventing progression of hypophosphatemic rickets in a subject in need thereof, the method comprising administering to the subject a therapeutically effective amount of any one of the ENPP1 mutant polypeptides, fusions, ENPP-1 containing polypeptides, or conjugates described herein, to thereby reduce, reverse, or prevent progression of hypophosphatemic rickets in the subject.

The disclosure further includes a method of reducing or preventing progression of at least one disease selected from the group consisting of chronic kidney disease (CKD), end stage renal disease (ESRD), calcific uremic arteriolopathy (CUA), calciphylaxis, ossification of the posterior longitudinal ligament (OPLL), hypophosphatemic rickets, osteoarthritis, aging related hardening of arteries, idiopathic infantile arterial calcification (IIAC), Generalized Arterial Calcification of Infancy (GACI), and calcification of atherosclerotic plaques in a subject diagnosed with the at least one disease, the method comprising administering to the subject a therapeutically effective amount of any one of the ENPP1 mutant polypeptides, fusions, ENPP-1 containing polypeptides, or conjugates described herein, to thereby reduce or prevent progression of the disease.

The disclosure further includes a method of reducing or preventing progression of aging related hardening of arteries in a subject in need thereof, the method comprising administering to the subject a therapeutically effective amount of any one of the ENPP1 mutant polypeptides, fusions, ENPP-1 containing polypeptides, or conjugates described herein, to thereby reduce or prevent progression of aging related hardening of arteries in the subject.

The disclosure further includes a method of raising pyrophosphate (PPi) levels in a subject having PPi level lower than PPi normal level, the method comprising administering to the subject a therapeutically effective amount of any one of the ENPP1 mutant polypeptides, fusions, ENPP-1 containing polypeptides, or conjugates described herein, whereby upon the administration the level of the PPi in the subject is elevated to a normal level of at least 2 μM and is maintained at approximately the same level.

The disclosure further includes a method of reducing or preventing the progression of pathological calcification or ossification in a subject having pyrophosphate (PPi) level lower than PPi normal level, the method comprising administering to the subject a therapeutically effective amount of any one of the ENPP1 mutant polypeptides, fusions, ENPP-1 containing polypeptides, or conjugates described herein, whereby pathological calcification or ossification in the subject is reduced or progression of pathological calcification or ossification in the subject is prevented.

The disclosure further includes a method of treating ENPP1 deficiency manifested by a reduction of extracellular pyrophosphate (PPi) concentration in a subject in need thereof, the method comprising administering to the subject a therapeutically effective amount of any one of the ENPP1 mutant polypeptides, fusions, ENPP-1 containing polypeptides, or conjugates described herein, whereby the level of the PPi in the subject is elevated.

In certain embodiments, the pathological calcification is selected from the group consisting of idiopathic infantile arterial calcification (IIAC) and calcification of atherosclerotic plaques.

In certain embodiments, the pathological ossification is selected from the group consisting of ossification of the posterior longitudinal ligament (OPLL), hypophosphatemic rickets, and osteoarthritis.

In certain embodiments, the soft tissue calcification is selected from the group consisting of IIAC and osteoarthritis.

In certain embodiments of any of the methods described herein, the soft tissue is selected from the group consisting of atherosclerotic plaques, muscular arteries, joint, spine, articular cartilage, vertebral disk cartilage, vessels, and connective tissue. In other embodiments, the soft tissue comprises atherosclerotic plaques. In yet other embodiments, the soft tissue comprises muscular arteries. In yet other embodiments, the soft tissue is selected from the group consisting of joint and spine. In yet other embodiments, the joint is selected from the group consisting of joints of the hands and joints of the feet. In yet other embodiments, the soft tissue is selected from the group consisting of articular cartilage and vertebral disk cartilage. In yet other embodiments, the soft tissue comprises vessels. In yet other embodiments, the soft tissue comprises connective tissue.

In certain embodiments, the subject is diagnosed with progeria.

In certain embodiments of any of the methods described herein, the ENPP1 mutant polypeptide, fusion, or ENPP1-containing polypeptide is a secreted product of a ENPP1 precursor protein expressed in a mammalian cell, wherein the ENPP1 precursor protein comprises a signal peptide sequence and an ENPP1 polypeptide, wherein the ENPP1 precursor protein undergoes proteolytic processing to yield the ENPP1 polypeptide. In certain embodiments, the polypeptide of the disclosure is a secreted product of a ENPP1 precursor protein expressed in a mammalian cell. In other embodiments, the ENPP1 precursor protein comprises a signal peptide sequence and an ENPP1 polypeptide, wherein the ENPP1 precursor protein undergoes proteolytic processing to the polypeptide of the disclosure. In yet other embodiments, in the ENPP1 precursor protein the signal peptide sequence is conjugated to the ENPP1 polypeptide N-terminus. Upon proteolysis, the signal sequence is cleaved from the ENPP1 precursor protein to provide the ENPP1 polypeptide. In certain embodiments, the signal peptide sequence is selected from the group consisting of ENPP1 signal peptide sequence, ENPP2 signal peptide sequence, ENPP7 signal peptide sequence, and ENPP5 signal peptide sequence.

In certain embodiments, the polypeptide is administered acutely or chronically to the subject. In other embodiments, the polypeptide is administered locally, regionally, parenterally or systemically to the subject.

In certain embodiments, the subject is a mammal. In other embodiments, the mammal is human.

In certain embodiments, the ENPP1 mutant polypeptide, the ENPP1-containing polypeptide, or fusion, or its precursor protein, is administered by at least one route selected from the group consisting of subcutaneous, oral, aerosol, inhalational, rectal, vaginal, transdermal, subcutaneous, intranasal, buccal, sublingual, parenteral, intrathecal, intragastrical, ophthalmic, pulmonary, and topical. In other embodiments, the ENPP1 mutant polypeptide, the ENPP1-containing polypeptide, or fusion, or its precursor protein, is administered to the subject as a pharmaceutical composition further comprising at least one pharmaceutically acceptable carrier.

In certain embodiments, the ENPP1 mutant polypeptide, the ENPP1-containing polypeptide, or fusion, or its precursor protein, is administered acutely or chronically to the subject. In other embodiments, the ENPP1 mutant polypeptide, the ENPP1-containing polypeptide, or fusion, or its precursor protein, is administered locally, regionally or systemically to the subject. In yet another embodiment, the polypeptide, or its precursor protein, is delivered on an encoded vector, wherein the vector encodes the protein and it is transcribed and translated from the vector upon administration of the vector to the subject.

It will be appreciated by one of skill in the art, when armed with the present disclosure including the methods detailed herein, that the disclosure is not limited to treatment of a disease or disorder once it is established. Particularly, the symptoms of the disease or disorder need not have manifested to the point of detriment to the subject; indeed, the disease or disorder need not be detected in a subject before treatment is administered. That is, significant pathology from disease or disorder does not have to occur before the present disclosure may provide benefit.

Thus, the present disclosure, as described more fully herein, includes a method for preventing diseases and disorders in a subject, in that a polypeptide of the disclosure, as discussed elsewhere herein, can be administered to a subject prior to the onset of the disease or disorder, thereby preventing the disease or disorder from developing. Particularly, where the symptoms of the disease or disorder have not manifested to the point of detriment to the subject; indeed, the disease or disorder need not be detected in a subject before treatment is administered. That is, significant pathology from the disease or disorder does not have to occur before the present disclosure may provide benefit. Therefore, the present disclosure includes methods for preventing or delaying onset, or reducing progression or growth, of a disease or disorder in a subject, in that a polypeptide of the disclosure can be administered to a subject prior to detection of the disease or disorder. In certain embodiments, the polypeptide of the disclosure is administered to a subject with a strong family history of the disease or disorder, thereby preventing or delaying onset or progression of the disease or disorder.

Armed with the disclosure herein, one skilled in the art would thus appreciate that the prevention of a disease or disorder in a subject encompasses administering to a subject a polypeptide of the disclosure as a preventative measure against the disease or disorder.

Pharmaceutical Compositions and Formulations

The disclosure provides pharmaceutical compositions comprising a polypeptide of the disclosure within the methods described herein.

Such a pharmaceutical composition is in a form suitable for administration to a subject, or the pharmaceutical composition may further comprise one or more pharmaceutically acceptable carriers, one or more additional ingredients, or some combination of these. The various components of the pharmaceutical composition may be present in the form of a physiologically acceptable salt, such as in combination with a physiologically acceptable cation or anion, as is well known in the art.

In an embodiment, the pharmaceutical compositions useful for practicing the method of the disclosure may be administered to deliver a dose of between 1 ng/kg/day and 100 mg/kg/day. In other embodiments, the pharmaceutical compositions useful for practicing the disclosure may be administered to deliver a dose of between 1 ng/kg/day and 500 mg/kg/day.

The relative amounts of the active ingredient, the pharmaceutically acceptable carrier, and any additional ingredients in a pharmaceutical composition of the disclosure will vary, depending upon the identity, size, and condition of the subject treated and further depending upon the route by which the composition is to be administered. By way of example, the composition may comprise between about 0.1% and about 100% (w/w) active ingredient.

Pharmaceutical compositions that are useful in the methods of the disclosure may be suitably developed for inhalational, oral, rectal, vaginal, parenteral, topical, transdermal, pulmonary, intranasal, buccal, ophthalmic, intrathecal, intravenous or another route of administration. Other contemplated formulations include projected nanoparticles, liposomal preparations, resealed erythrocytes containing the active ingredient, and immunologically-based formulations. The route(s) of administration is readily apparent to the skilled artisan and depends upon any number of factors including the type and severity of the disease being treated, the type and age of the veterinary or human patient being treated, and the like.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

As used herein, a "unit dose" is a discrete amount of the pharmaceutical composition comprising a predetermined amount of the active ingredient. The amount of the active ingredient is generally equal to the dosage of the active ingredient that would be administered to a subject or a convenient fraction of such a dosage such as, for example, one-half or one-third of such a dosage. The unit dosage form may be for a single daily dose or one of multiple daily doses (e.g., about 1 to 4 or more times per day). When multiple daily doses are used, the unit dosage form may be the same or different for each dose.

Administration/Dosing

The regimen of administration may affect what constitutes an effective amount. For example, several divided dosages, as well as staggered dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation. In certain embodiments, administration of the compound of the disclosure to a subject elevates the subject's plasma PPi to a level that is close to normal, where a normal level of PPi in mammals is 1-3 μM. "Close to normal" refers to 0 to 1.2 μM or 0-40% below or above normal, 30 ηM to 0.9 μM or 1-30% below or above normal, 0 to 0.6 μM or 0-20% below or above normal, or 0 to 0.3 μM or 0-10% below or above normal.

Administration of the compositions of the present disclosure to a patient, such as a mammal, such as a human, may be carried out using known procedures, at dosages and for periods of time effective to treat a disease or disorder in the patient. An effective amount of the therapeutic compound necessary to achieve a therapeutic effect may vary according to factors such as the activity of the particular compound employed; the time of administration; the rate of excretion of the compound; the duration of the treatment; other drugs, compounds or materials used in combination with the compound; the state of the disease or disorder, age, sex, weight, condition, general health and prior medical history of the patient being treated, and like factors well-known in the medical arts. Dosage regimens may be adjusted to provide the optimum therapeutic response. Dosage is determined based on the biological activity of the therapeutic compound which in turn depends on the half-life and the area under the plasma time of the therapeutic compound curve. The polypeptide according to the disclosure is administered at an appropriate time interval of every 2 days, or every 4 days, or every week or every month so as to achieve a continuous level of plasma PPi that is either close to the normal (1-3 μM) level or above (30-50% higher than) normal levels of PPi. Therapeutic dosage of the polypeptides of the disclosure may also be determined based on half-life or the rate at which the therapeutic polypeptide is cleared out of the body. The polypeptide according to the disclosure is administered at appropriate time intervals of either every 2 days, or every 4 days, every week or every month so as to achieve a constant level of enzymatic activity of ENPP1.

For example, several divided doses may be administered daily or the dose may be proportionally reduced as indicated by the exigencies of the therapeutic situation. A non-limiting example of an effective dose range for a therapeutic compound of the disclosure is from about 0.01 and 50 mg/kg of body weight/per day. In certain embodiments, the effective dose range for a therapeutic compound of the disclosure is from about 50 ng to 500 ng/kg, preferably 100 ng to 300 ng/kg of bodyweight. One of ordinary skill in the art would be able to study the relevant factors and make the determination regarding the effective amount of the therapeutic compound without undue experimentation.

The compound can be administered to a patient as frequently as several times daily, or it may be administered less frequently, such as once a day, once a week, once every two weeks, once a month, or even less frequently, such as once every several months or even once a year or less. It is understood that the amount of compound dosed per day may be administered, in non-limiting examples, every day, every other day, every 2 days, every 3 days, every 4 days, or every 5 days. For example, with every other day administration, a 5 mg per day dose may be initiated on Monday with a first subsequent 5 mg per day dose administered on Wednesday, a second subsequent 5 mg per day dose administered on Friday, and so on. The frequency of the dose is readily apparent to the skilled artisan and depends upon any number of factors, such as, but not limited to, the type and severity of the disease being treated, and the type and age of the patient.

Actual dosage levels of the active ingredients in the pharmaceutical compositions of this disclosure may be varied so as to obtain an amount of the active ingredient that is effective to achieve the desired therapeutic response for a particular patient, composition, and mode of administration, without being toxic to the patient.

A medical doctor, e.g., physician, having ordinary skill in the art may readily determine and prescribe the effective amount of the pharmaceutical composition required. For example, the physician or veterinarian could start doses of the compounds of the disclosure employed in the pharmaceutical composition at levels lower than that required in order to achieve the desired therapeutic effect and gradually increase the dosage until the desired effect is achieved.

In certain embodiments, the compositions of the disclosure are administered to the patient in dosages that range from one to five times per day or more. In other embodiments, the compositions of the disclosure are administered to the patient in range of dosages that include, but are not limited to, once every day, every two, days, every three days to once a week, and once every two weeks. The frequency of administration of the various combination compositions of the disclosure varies from subject to subject depending on many factors including, but not limited to, age, disease or disorder to be treated, gender, overall health, and other factors. Thus, the disclosure should not be construed to be limited to any particular dosage regime and the precise dosage and composition to be administered to any patient will be determined by the attending physical taking all other factors about the patient into account.

In certain embodiments, the present disclosure is directed to a packaged pharmaceutical composition comprising a container holding a therapeutically effective amount of a compound of the disclosure, alone or in combination with a second pharmaceutical agent; and instructions for using the compound to treat, prevent, or reduce one or more symptoms of a disease or disorder in a patient.

Routes of Administration

Routes of administration of any of the compositions of the disclosure include inhalational, oral, nasal, rectal, parenteral, sublingual, transdermal, transmucosal (e.g., sublingual, lingual, (trans) buccal, (trans) urethral, vaginal (e.g., trans- and perivaginally), (intra) nasal, and (trans) rectal), intravesical, intrapulmonary, intraduodenal, intragastrical, intrathecal, subcutaneous, intramuscular, intradermal, intra-arterial, intravenous, intrabronchial, inhalation, and topical administration.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. The formulations and compositions that would be useful in the present disclosure are not limited to the particular formulations and compositions that are described herein.

Parenteral Administration

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intravenous, intraperitoneal, intramuscular, intrasternal injection, and kidney dialytic infusion techniques.

Additional Administration Forms

Additional dosage forms of this disclosure include dosage forms as described in U.S.

U.S. Pat. Nos. 6,340,475, 6,488,962, 6,451,808, 5,972,389, 5,582,837, and 5,007,790. Additional dosage forms of this disclosure also include dosage forms as described in U.S. patents applications Ser. Nos. 20/030147952, 20030104062, 20030104053, 20030044466, 20030039688, and 20020051820. Additional dosage forms of this disclosure also include dosage forms as described in PCT Applications Nos. WO 03/35041, WO 03/35040, WO 03/35029, WO 03/35177, WO 03/35039, WO 02/96404, WO 02/32416, WO 01/97783, WO 01/56544, WO 01/32217, WO 98/55107, WO 98/11879, WO 97/47285, WO 93/18755, and WO 90/11757.

Controlled Release Formulations and Drug Delivery Systems

Controlled- or sustained-release formulations of a pharmaceutical composition of the disclosure may be made using conventional technology. In some cases, the dosage forms to be used can be provided as slow or controlled-release of one or more active ingredients therein using, for example, hydropropylmethyl cellulose, other polymer matrices, gels, permeable membranes, osmotic systems, multilayer coatings, microparticles, liposomes, or microspheres or a combination thereof to provide the desired release profile in varying proportions. Single unit dosage forms suitable for oral administration, such as tablets, capsules, gelcaps, and caplets, which are adapted for controlled-release are encompassed by the present disclosure.

In certain embodiments, the formulations of the present disclosure may be, but are not limited to, short-term, rapid-offset, as well as controlled, for example, sustained release, delayed release and pulsatile release formulations.

The term sustained release is used in its conventional sense to refer to a drug formulation that provides for gradual release of a drug over an extended period of time, and that may, although not necessarily, result in substantially constant blood levels of a drug over an extended time period. The period of time may be as long as a month or more and should be a release that is longer that the same amount of agent administered in bolus form. For sustained release, the compounds may be formulated with a suitable polymer or hydrophobic material that provides sustained release properties to the compounds. As such, the compounds for use the method of the disclosure may be administered in the form of microparticles, for example, by injection or in the form of wafers or discs by implantation. In certain embodiments of the disclosure, the compounds of the disclosure are administered to a patient, alone or in combination with another pharmaceutical agent, using a sustained release formulation.

The term delayed release is used herein in its conventional sense to refer to a drug formulation that provides for an initial release of the drug after some delay following drug administration and that mat, although not necessarily, includes a delay of from about 10 minutes up to about 12 hours. The term pulsatile release is used herein in its conventional sense to refer to a drug formulation that provides release of the drug in such a way as to produce pulsed plasma profiles of the drug after drug administration. The term immediate release is used in its conventional sense to refer to a drug formulation that provides for release of the drug immediately after drug administration.

As used herein, short-term refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes and any or all whole or partial increments thereof after drug administration after drug administration.

As used herein, rapid-offset refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes, and any and all whole or partial increments thereof after drug administration.

Those skilled in the art will recognize, or be able to ascertain using no more than routine experimentation, numerous equivalents to the specific procedures, embodiments, claims, and examples described herein. Such equivalents were considered to be within the scope of this disclosure and covered by the claims appended hereto. For example, it should be understood, that modifications in reaction and preparation conditions, with art-recognized alternatives and using no more than routine experimentation, are within the scope of the present application.

It is to be understood that wherever values and ranges are provided herein, all values and ranges encompassed by these values and ranges, are meant to be encompassed within the scope of the present disclosure. Moreover, all values that fall within these ranges, as well as the upper or lower limits of a range of values, are also contemplated by the present application.

The following examples further illustrate aspects of the present disclosure. However, they are in no way a limitation of the teachings or disclosure of the present disclosure as set forth herein.

EXAMPLES

The disclosure is now described with reference to the following Examples. These Examples are provided for the purpose of illustration only, and the disclosure is not limited to these Examples, but rather encompasses all variations that are evident as a result of the teachings provided herein.

Methods and Materials

Unless specifically mentioned, expression of constructs in CHO cells or modified CHO cells with and without supplementation, $V_{max}$ Assay, $K_m/K_{cat}$ Assay, AUC assay, half-life assay were carried out using protocols described elsewhere herein Generation of ENPP1-Fc Mutant Constructs Human NPP1 (Human: NCBI accession NP 006199) was modified to express soluble, recombinant protein was fused to IgG1 by sub cloning into pFUSE-hlgG1-Fc1 or pFUSE-mlgG1-Fc1 plasmids (InvivoGen, San Diego CA), respectively. The constructs were generated from SEQ ID NO:7) using site-directed mutagenesis using commercially available kits. (Q5® Site-Directed Mutagenesis Kit/New England Biolabs). The constructs thus generated were sequenced to verify the nucleic acid sequence and then used for expression of protein.

Expression of ENPP1-Fc Mutant Constructs

Stable transfections of the ENPP1-Fc constructs were established in CHO K1 cells (Sigma Aldrich, 85051005) under Zeocin/gentamycin selection, and were adapted for suspension growth. Adapted cells were used to seed liquid culture growths in CD FORTICHO™ medium (A1148301, Thermo Fischer) or PEPROGROW™ AF-CHO (PeproTech AF-CHO) in shaker flasks at 37° C. and 5% $CO_2$, agitated at 120 rpm with high humidity. The culture was gradually expanded to the desired target volume and then maintained for another 2 days to accumulate extracellular protein Expression of ENPP1-Fc Mutant Constructs in Modified CHO Cells CHO-K1 cells were modified to generate CHO-K1-MOD cells stably expressing human α-2,6-sialyltransferase (α-2,6-ST) enzyme. Stable transfections of the ENPP1-Fc constructs were established in CHO K1-MOD cells, and protein was expressed following the same protocol as described above. Optionally in some constructs, the cell culture medium of CHO-K1-MOD cells expressing the corresponding constructs were supplemented with sialic acid or a "high-flux" precursor of sialic acid called 1,3,4-O-Bu3ManNAc to facilitate higher levels of glycosylate during protein production Purification of ENPP1-Fc Mutant Constructs The liquid cultures were centrifuged at 4300×g for 5 mm and the supernatants were filtered through a 0.2 µm membrane and concentrated via tangential flow using a Pellicon®3 0. 0.11 m2 Ultracell® 30 D cassette (Millipore, Billerica MA). The concentrated supernatant was then purified by a combination of chromatographic techniques in a multi-step process. These techniques are performed sequentially and may include any of the following: affinity chromatography with protein A or protein G, cation-exchange chromatography, anion-exchange chromatography, size exclusion chromatography, hydrophobic exchange chromatography, high-pressure liquid chromatography (HPLC), precipitation steps, extractions steps, lyophilization steps, and/or crystallization steps. Using any one of these steps in series, one skilled in the art of protein chemistry can purify the compositions of matter described to homogeneity such that there are no contaminating protein bands on a silver stained gel. The resulting protein samples then tested with Pierce LAL Chromogenic Endotoxin Quantitation Kit (cat. 88282) to verify that all were free of endotoxin.

In order to quantitate the biological impact of clone optimization, the pharmacodynamics effects of select ENPP1-Fc isoforms were quantitated by determining plasma PPi concentrations at multiple time points following a single subcutaneous dose of each isoform.

$K_m/K_{cat}$ Determination

The steady state hydrolysis of ATP by ENPP1 constructs was determined by HPLC. Briefly, enzyme reactions were started by addition of 10 nM PPi to varying concentrations of ATP in the reaction buffer containing 20 mM Tris, pH 7.4, 150 mM NaCl, 4.5 nM KCl, 14 mM $ZnCl_2$, 1 mM $MgCl_2$, and 1 mM $CaCl_2$). At various time points, 50 µl reaction solution were removed and quenched with an equal volume of 3M formic acid. The quenched reaction solution was loaded on a C-18 (5 m t 250× 4.6 mm) column (Higgins Analytical) equilibrated in 5 mM ammonium acetate (pH 6.0) solution and eluted with a 0% to 20% methanol gradient. Substrate and products were monitored by UV absorbance at 259 nm and quantified according to the integration of their correspondent peaks and standard curves.

$V_{max}$ Assay

For each of the mutants prepared, phosphodiesterase activity was analyzed using thymidine 5'-monophosphate p-nitrophenyl ester (pNP-TMP) (Saunders, et al., 2008, Mol. Cancer Ther. 7 (10): 3352-62; Albright, et al., 2015, Nat Commun. 6:10006).

Area Under the Curve Assay

The area under the plasma concentration versus time curve, also called the area under the curve (AUC) can be used as a means of evaluating the volume of distribution (V), total elimination clearance (CL), and bioavailability (F) for extravascular drug delivery. Area under plasma time curve for each expressed and purified ENPP1-Fc construct were carried out using the standard equation to determine half-life and bioavailability after a single subcutaneous injection of biologic, as described in Equation 1.

Half-Life Determination

The drug half-life ($t_{1/2}$) is the time it takes for the plasma concentration or the amount of drug or biologic in the body to be reduced by 50%. Half-life values for each expressed and purified ENPP1-Fc construct were carried out following protocols described in the prior art and/or herein, such as Equation 1, which allows for determining half-life and bioavailability after a single subcutaneous injection of biologic.

Drug half-life can be calculated using Equation 1, which correlates the relationship between systemic fractional concentration and time of a drug administered to a subcutaneous depot in a single injection. Plotting the data as fraction of drug absorbed (F) over time (t) allows for the determination of the elimination ($k_e$) and absorption ($k_a$) constants by fitting the data to the equation for the total systemic absorption of a drug administered at a subcutaneous depot at time t=0.

$$F = \frac{k_a}{(k_a - k_e)}\left[e^{-k_e t} - e^{-k_a t}\right] \qquad \text{(Equation 1)}$$

Example 1: Selection and Optimization of Glycosylation Mutations

A ENPP1-Fc construct was subjected to mutations so as to introduce putative additional glycosylation sites and/or increase affinity of the Fc for the neonatal orphan receptor (FcRn). Mutations tested are illustrated elsewhere herein, and specific Constructs of the discussion are illustrated below.

Figure 7A:
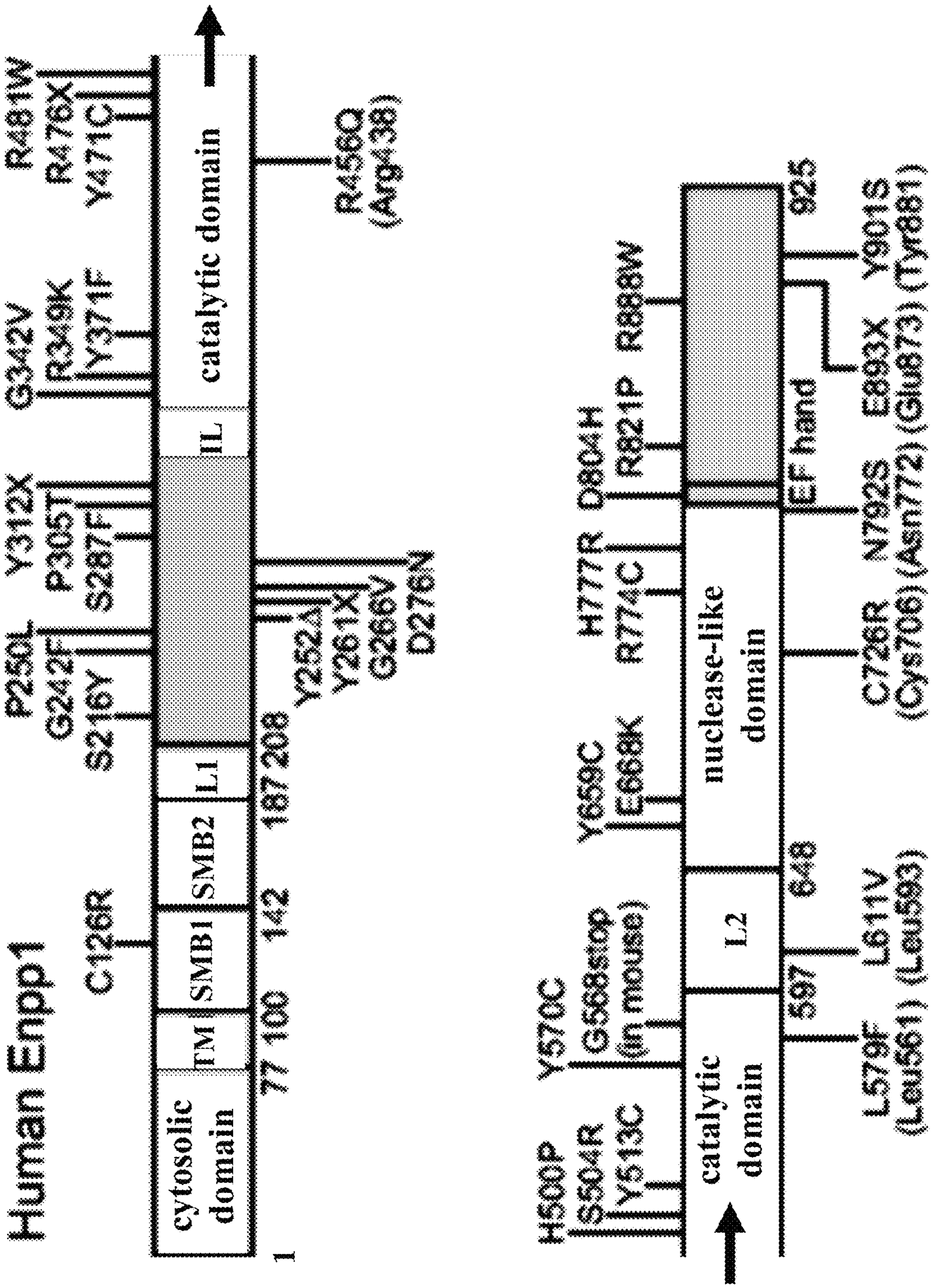
FIG. 7A illustrates certain domains of human ENPP1 with known loss of function mutations that result in the human disease "Generalized Arterial Calcification of Infancy" (GACI). In certain embodiments, glycosylation sites are not introduced near regions with known loss of function mutations that result in GACI (illustrated in FIG. 7A).
Figure 7B:
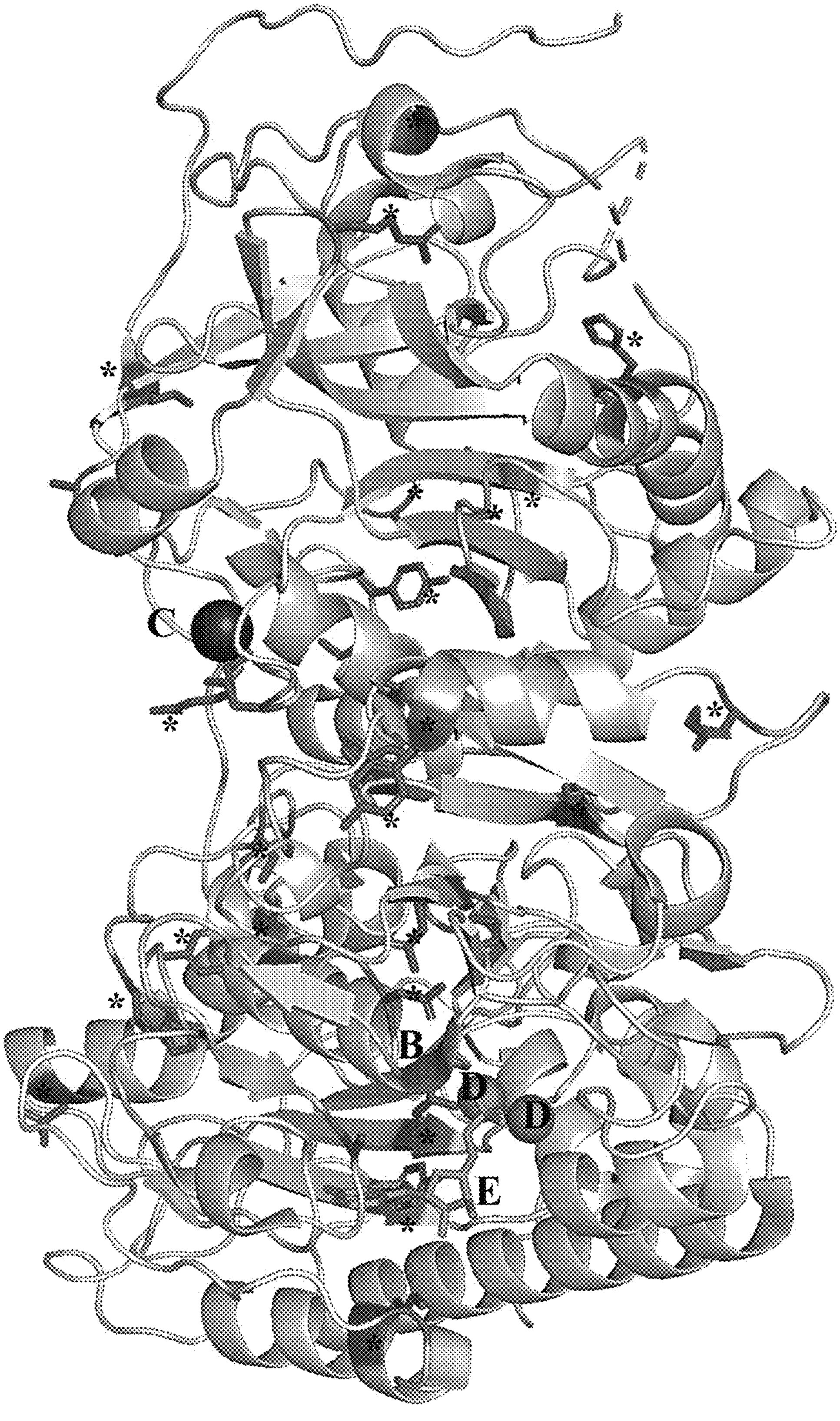
FIG. 7B illustrates the crystal structure of ENPP1, with residues where known loss of function mutations resulting in GACI are highlighted (and marked with *). The residue in (B) is located in the catalytic domain and corresponds to T238A. As in FIG. 6: calcium atom (C); 2 Zinc atoms (D); ATP molecule (E).
Figure 8A:
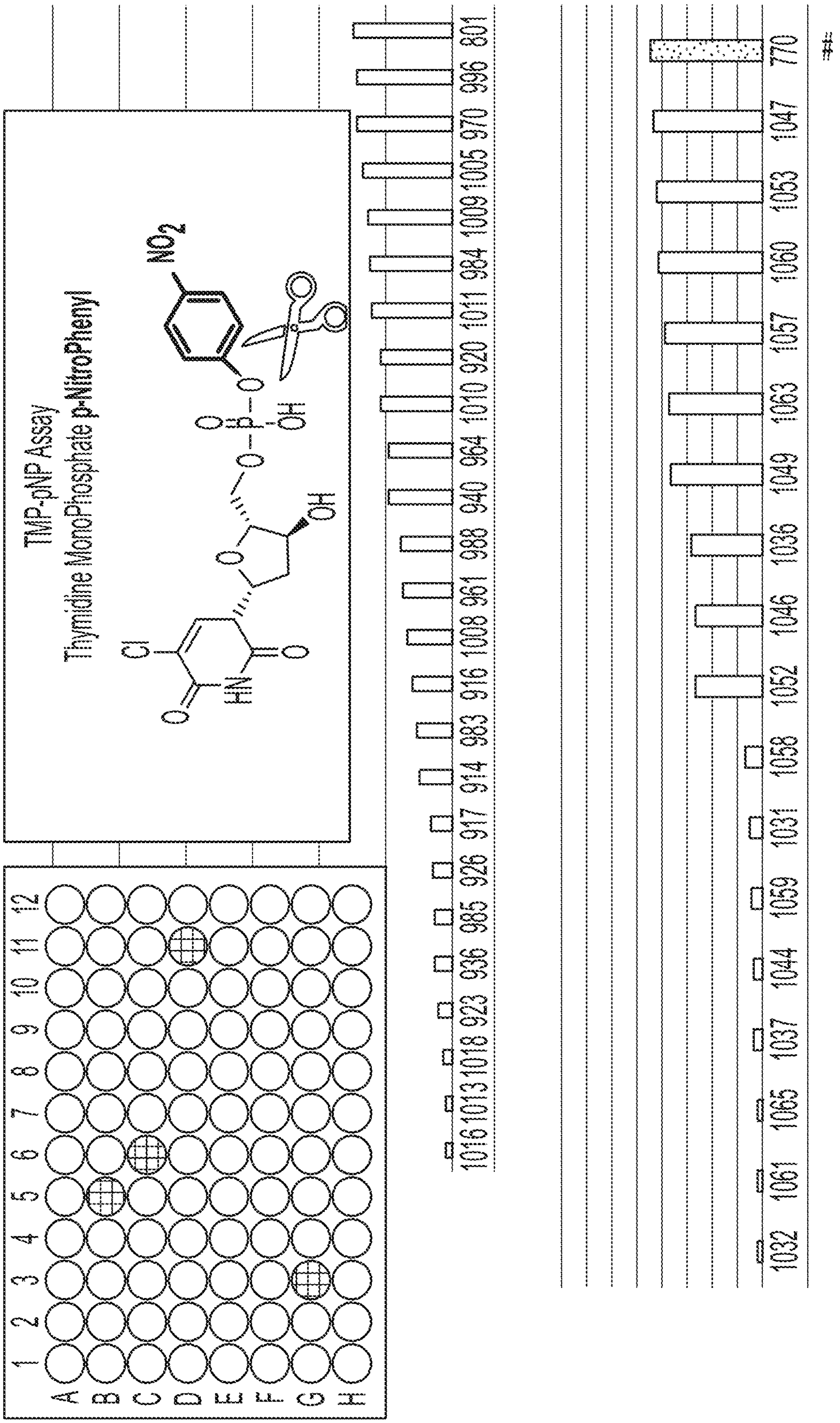
FIGS. 8A-8D illustrate selected results from high throughput TMP-pNP (thymidine monophosphate-p-nitrophenyl) assays of ENPP1 polypeptides for phosphodiesterase activity. This is a high throughput assay designed be the inventors to rapidly screen glycosylation isoforms introduced into Construct #770. The figure illustrates designing and executing a high throughput screen that is capable of rapid assessment of biological efficacy of mutants forms of the parent polypeptide-Construct #770. Construct numbers in (#) represent the original WT clone before mutations were introduced. Construct numbers in (*) show clones with possible gain of function mutations.
Figure 8B:
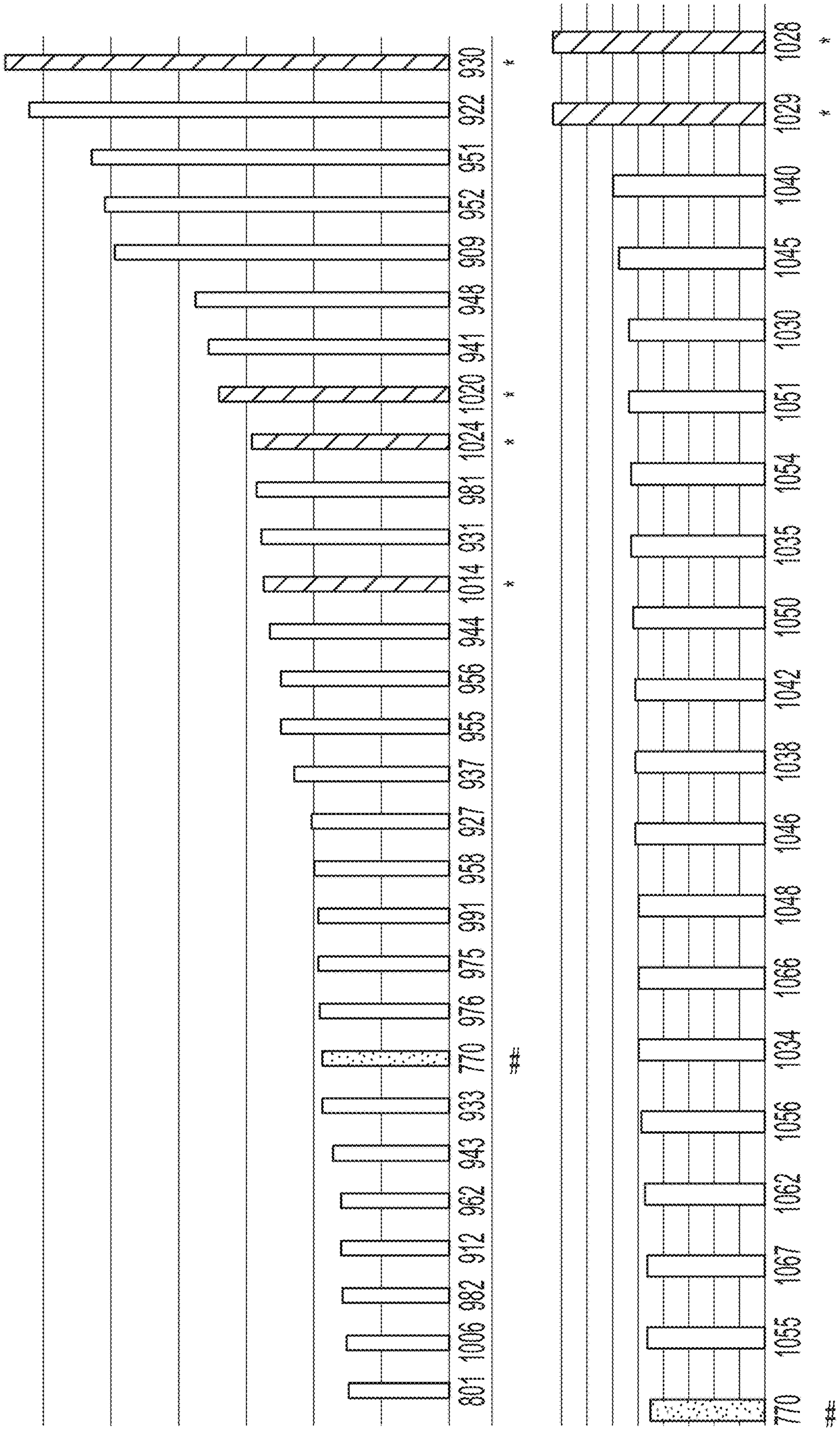
Figure 8C:
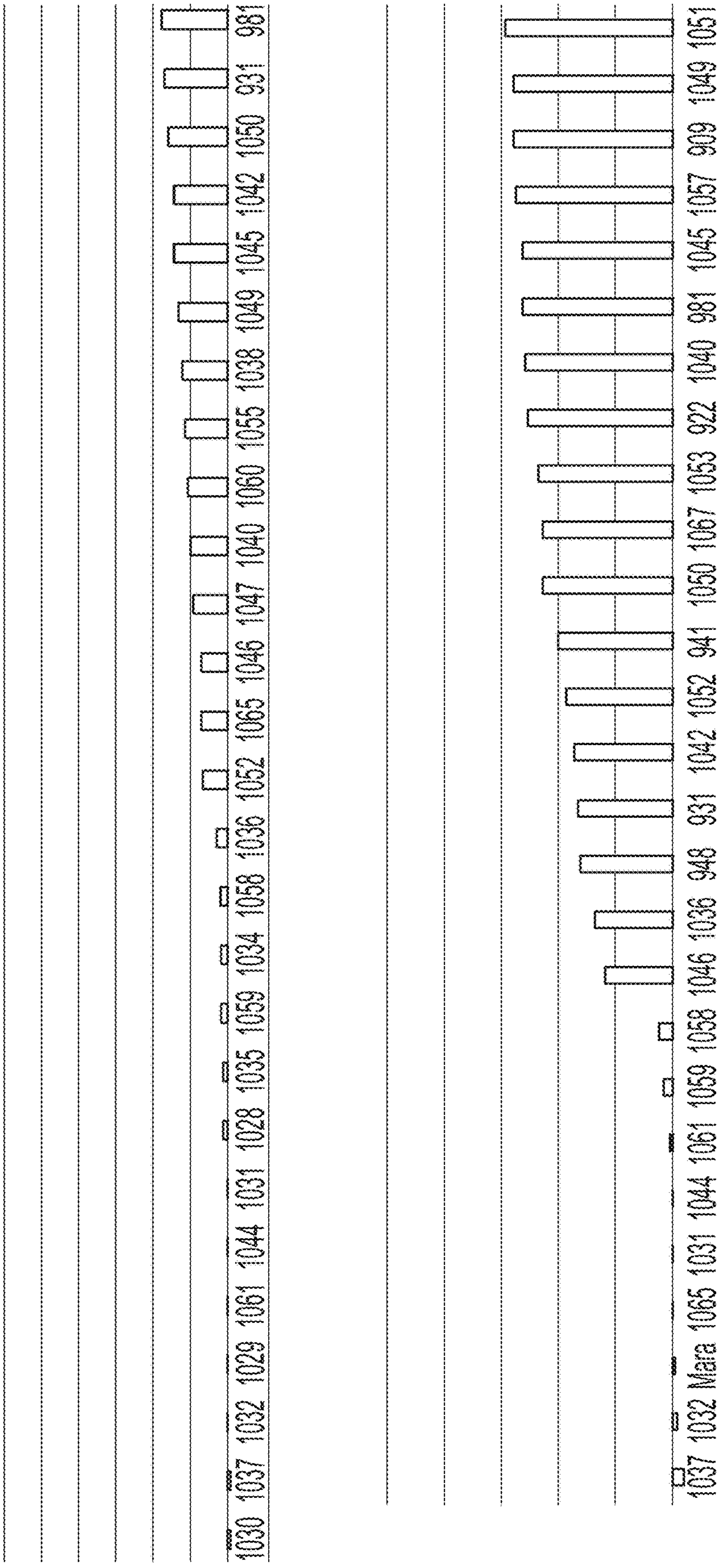
Figure 8D:
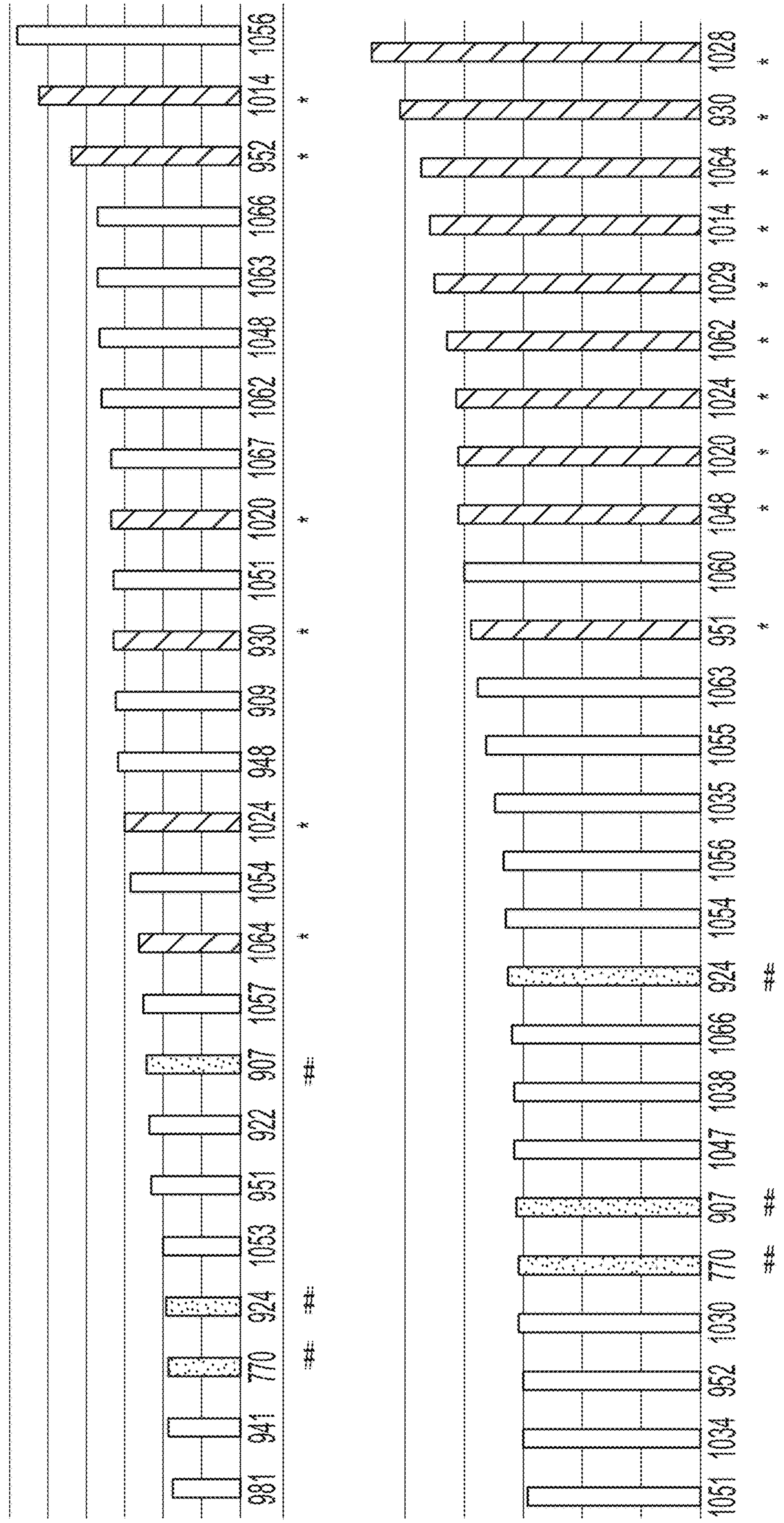

Improvement of the pharmacokinetic properties of the ENPP1-Fc was sought by introducing additional N-linked glycosylation sites and enhancing the pH dependent recycling of the fusion protein. As a way to guide the selection of additional N-linked glycosylation sites, electron density maps derived from X-ray diffraction of mouse Enpp1 crystals were used, and this revealed 4 glycosylation sites in Enpp1. These sites were assumed to be present in the highly homologous human ENPP1, and in addition, human ENPP1 contains an additional four N-linked glycosylation consensus sequences whose glycosylation status in unknown (FIG. 7B).

To identify regions of ENPP1 amenable to hyperglycosylation that would not adversely impact catalytic activity a combination of structural modeling, clinical data, and genetic data on ENPP1 in GACI patients was used. First, N-linked glycosylation consensus sequences were identified in ENPP2-7, and sequences that would easily permit the introduction of a glycosylation site via the alteration of a single adjacent residues were evaluated. ENPP2-7 was then structurally modeled using standard software to thread the sequences through the mouse Enpp1 structure (PDB ID code 4GTW). The location of proposed glycosylation sites were compared to sites of known inactivating ENPP1 mutations in GACI (FIGS. 7A-7B) as well as the locations of di-sulfide bonds in the enzyme. If the spatial location of the proposed glycosylation sites were predicted to interfere with either, the sites were discarded. These modeling studies resulted in identification of several potential sites for additional N-linked glycosylation procedures which could easily be introduced into ENPP1 that were not expected to disrupt the folding or enzymatic activity of the protein (FIGS. 8A-8D, 16A-16B, and 17).

The additional N-linked glycosylation consensus sequences were then introduced into human ENPP1-Fc (hENPP1-Fc, Construct #770) via site directed mutagenesis. The proteins were transiently expressed in CHO cells in 96 well plates and the enzymatic activity of the extracellular supernatant from each clone was screened in triplicate in a high throughput assay using pNP-TMP as a chromogenic substrate as described in the methods (FIGS. 7A-7D). The rate of pNP-TMP hydrolysis in 10 ENPP1-Fc isoforms was equal to or better than Construct #770 (FIGS. 7A-7D), and these 10 glycoforms were selected for combinatorial optimization with one-another and the IgG1 Fc domain as described elsewhere herein.

Figure 9A:
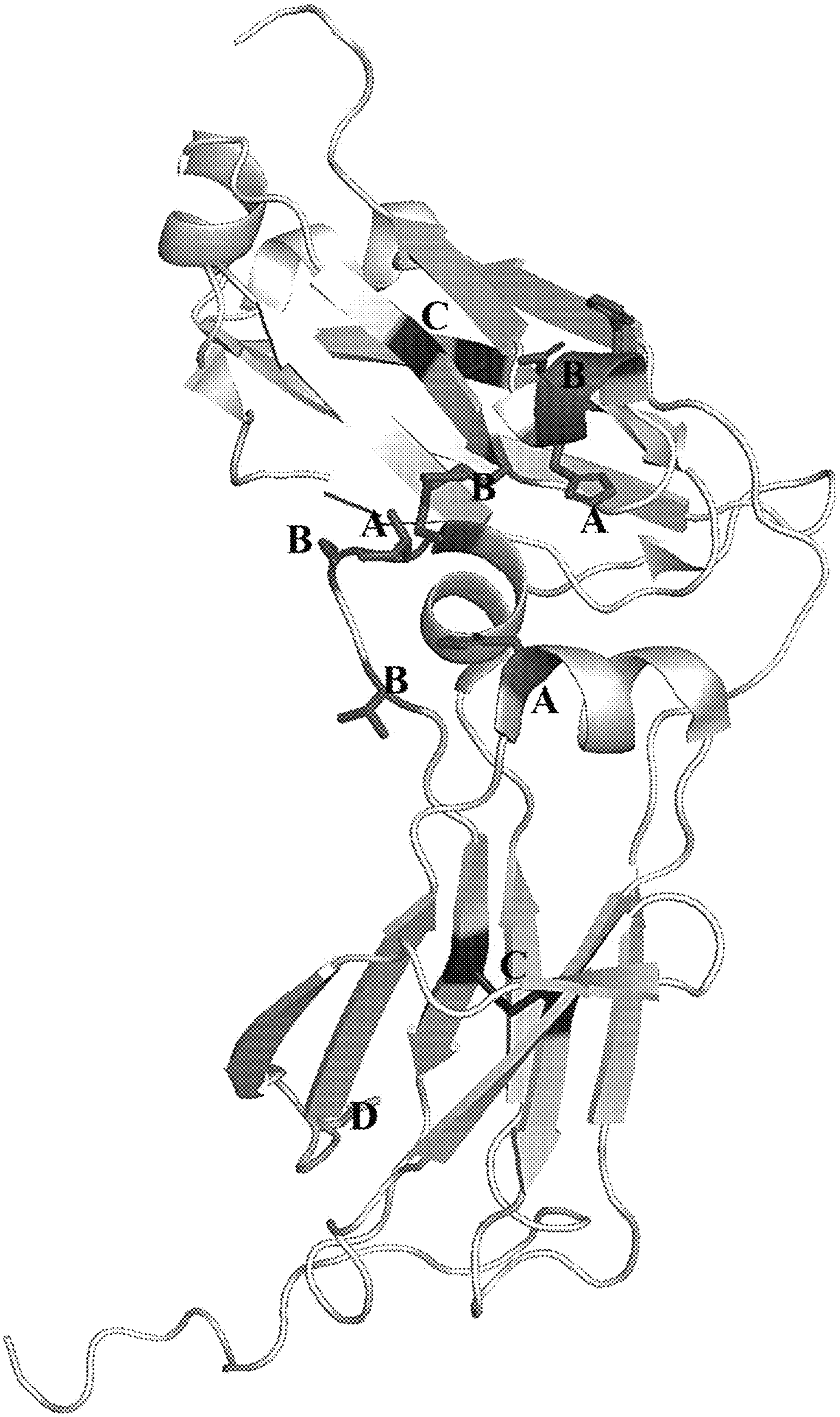
FIG. 9A is ribbon diagram illustrating the Fc domain of human IgG1. This domain is fused onto the C-terminal portion of ENPP1 to increase efficacy. Mutations in Fc domain were introduced to enhance pH-dependent recycling by FcRn. (A)=sites that abrogate binding of acidic dependence. (B)=sites that enhance binding. (C)=cysteine disulfide bonds. Magenta=known glycosylation sites.
Figure 9B:
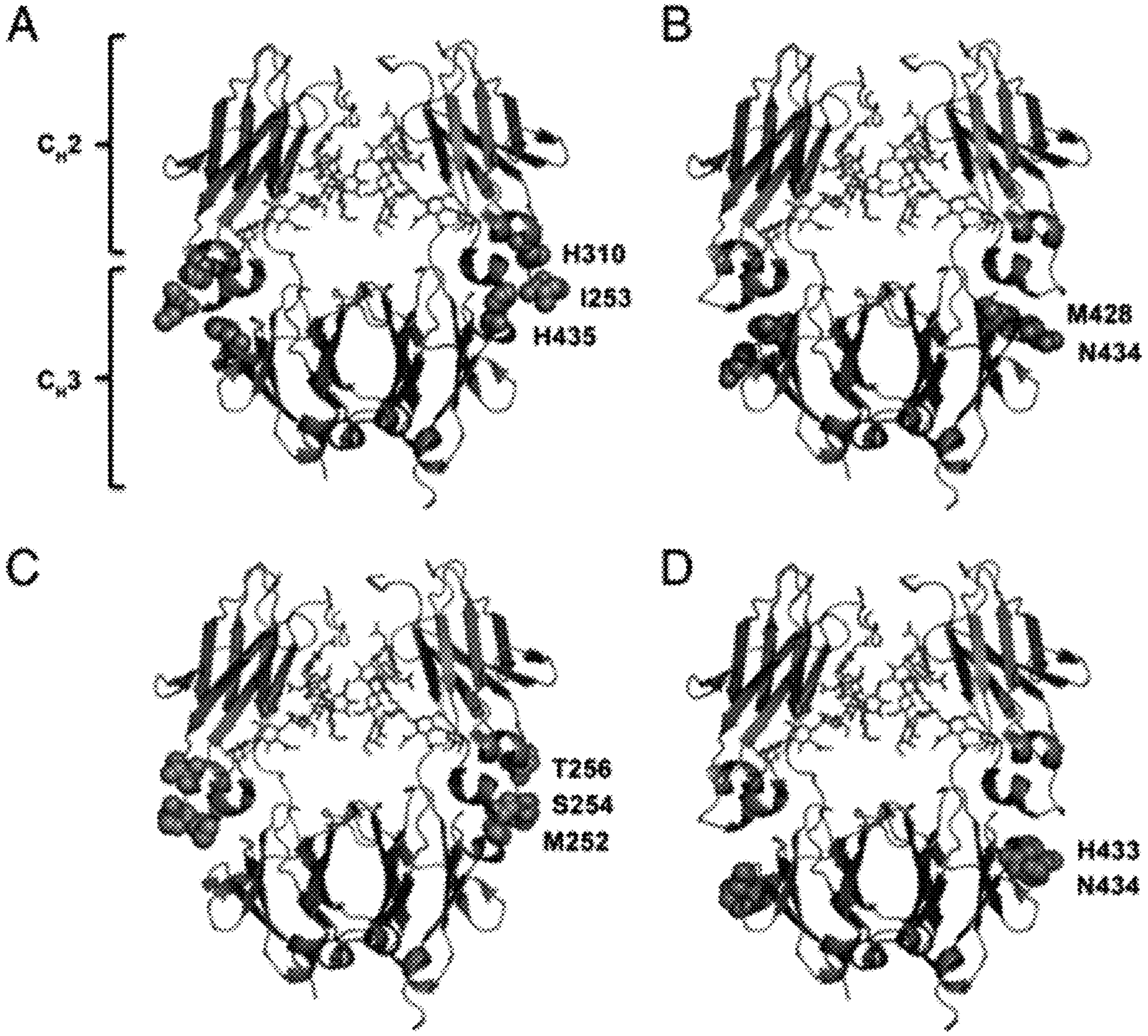
FIG. 9B illustrates mutations in the Fc domain of human IgG1 known to enhance pH dependent recycling by FcRn.

FcRn is the main homeostatic regulator of human IgG1 Fc serum half-life, and mutations in the Fc domain which enhance the pH dependent interactions of Fc with FcRn extend the circulatory half-life of biologic antibodies. Effects of two Fc mutations reported to enhance pH dependent recycling were examined herein-H433K/N434F, hereafter referred to as HN mutations, and M242Y/S254T/T246E, hereafter referred to as MST mutations (FIGS. 9A-9B). Either of the two variants of the Fc domain were combined randomly with one or more of the 10 ENPP1-Fc glycoforms demonstrating acceptable hydrolysis rates to create 12 additional ENPP1-Fc clones (Table 3). Some of these clones were chosen to test the effects of multiple glycoforms on pharmacokinetics of ENPP1-Fc, where two spatially distinct putative glycosylation sites on different protein domains were selected to enhance potential glycan shielding effects on protein surface area (Table 3; Constructs #1057, #1064, #1014, #1040, #1101). Other clones tested only the effect of Fc mutations on pK properties alone or in the presence of a single additional putative glycosylation (Table 3; Constructs #981 and #1051, respectively).

Example 2: Expression Using CHO Cell Lines and Growth Conditions

Non-human Chinese Hamster Ovary (CHO) cells are widely employed for the production of biologics due to the similarity of the CHO and human glycosylation patterns in recombinantly produced protein. Nevertheless, glycosylation differences between the two exist, most notably, human N-linked glycans contain terminal sialic acid residues with both α-2,3 and α-2,6 linkages while CHO cells contain only α-2,3 linkages.

To test whether terminal sialyation differences between CHO and human cells impact the PK and bioavailability in the present system, a CHO cell line stably expressing human α-2,6-sialyltransferase (α-2,6-ST) was established as a host, and this clone was used for the production of 7 ENPP1 isoforms to compared the effect of α-2,6 linkages on PK and bioavailability in the various Constructs (Table 5; Construct numbers ending in '-ST'). To explore the effects of growth conditions on PK and bioavailability, cells stably transfected with select ENPP1-Fc isoforms (both CHO K1 cells and CHO K1 cells stably transfected with human α-2,6-ST)

were supplemented with a "high-flux" precursor of sialic acid called 1,3,4-O-$Bu_3$ManNAc during protein production (Table 5).

The ENPP1-Fc isoforms were purified to homogeneity using an identical purification scheme and the Michaelis-Menton enzymatic rate constants and pharmacokinetic properties were determined as described elsewhere herein. Finally, to quantitate the biological impact of clone optimization, the pharmacodynamic effects of select ENPP1-Fc isoforms were quantitated by determining plasma PPi concentrations at multiple time points following a single subcutaneous dose of each isoform. The half-life and area under the curve were determined by plotting the fraction of drug absorbed (F) per time (t), and the elimination elimination ($k_e$) and absorption ($k_a$) constants were derived by fitting the data to Equation 1 for the total systemic absorption of a drug administered at a subcutaneous depot at time t=0.

Example 3: Pharmacokinetic Effects of Additional N-Linked Glycosylation Sites

Figure 2A:
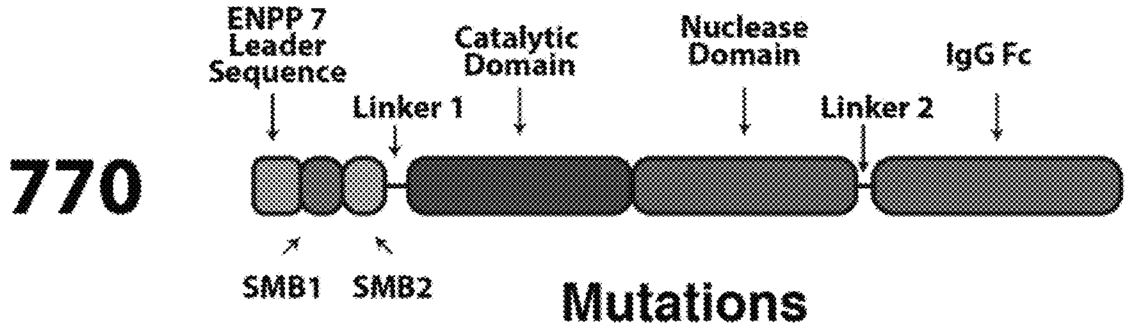
FIG. 2A illustrates the domain structure of the parent Construct #770. The 2 somatomedin B domains, catalytic domain, and endonuclease domain of human ENPP1 was fused N-terminally with the signal sequence of human ENPP7 and c-terminally with the Fc domain of human IgG1.
Figure 2B:
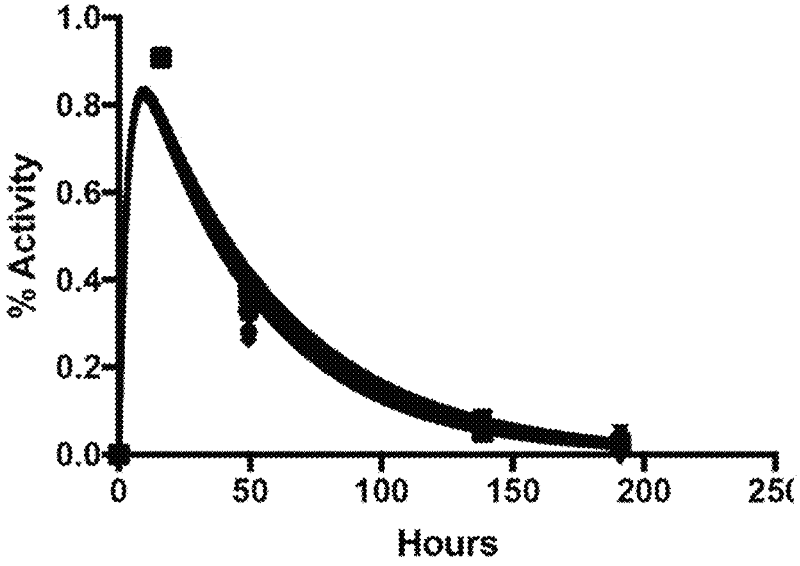
FIG. 2B illustrates pharmacokinetic analysis of the parent Construct #770. After an initial raise in plasma activity 17 hours after subcutaneous injection there is a steep drop off of plasma activity and a calculated half-life of 34 hours.
Figure 2C:
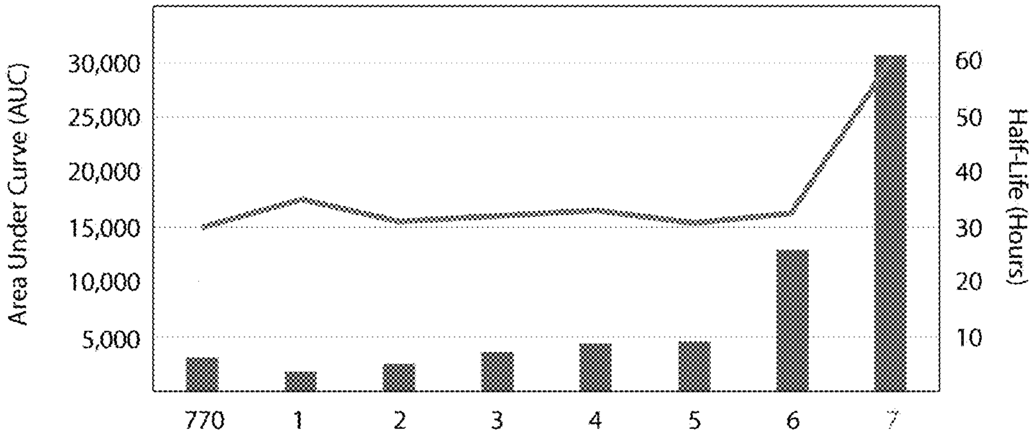
FIG. 2C illustrates a non-limiting effect of additional N-glycosylation consensus sequences engineered into the parent Construct #770. A pharmacokinetic plot of the AUC (bars, y-axis on left) and half-life in hours (line, y-axis on right) indicates Clone 7, with the I256T mutation, has a marketable increase in both AUC and half-life compared with parent Construct #770.

Representative plots for the parent isoform are displayed in FIG. 2B, yielding a half-life of 34 hours and an area under the curve (AUC) of 3,027 (Construct #770, Table).

Figure 10:
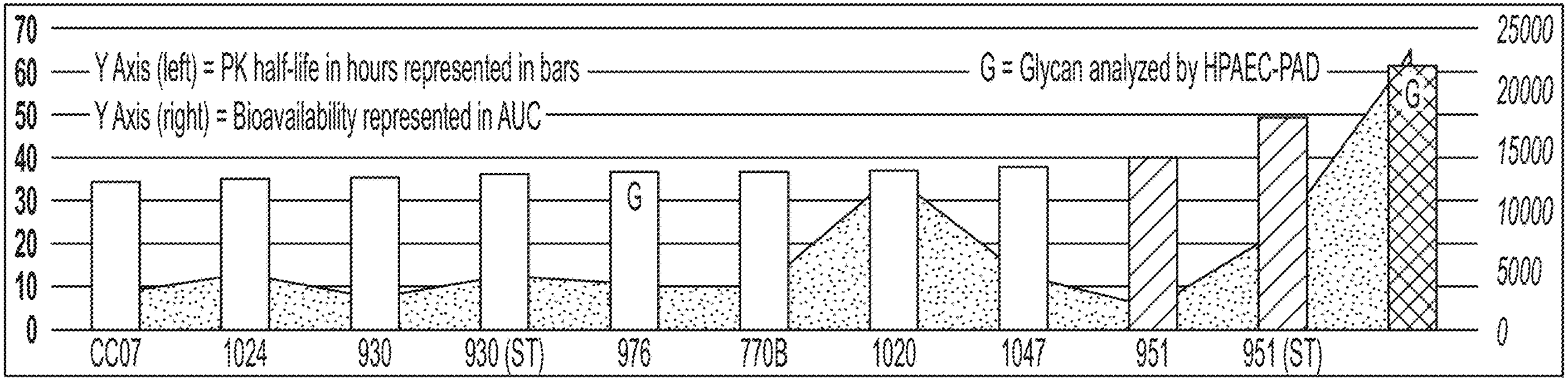
FIG. 10 comprises a graph and a table illustrating the effect of glycosylation in PK (in terms of half-life, hours) and bioavailability of ENPP1 polypeptides. The PK for all the mutations were comparable to that of Construct #CC07 (770B), except the I256T mutation of Construct #922. This mutation (located in the insertion loop of the catalytic domain) was modeled after the equivalent glycosylation site in ENPP3. Further, Construct #951 showed similar PK value to that of Construct #CC07, but Construct #951 grown in cell lines stably transfected with ST6GAL1 (Construct #951-ST) showed improved PK and bioavailability. Bioavailability was improved for Construct #922, which contains the I256T mutation. Construct #930 had similar half-life, but lower bioavailability, than Construct #CC07. In contrast, Construct #1020 had higher bioavailability than Construct #CC07. PK and bioavailability data are presented in the table, determined as illustrated in FIGS. 4, 5, and 13 and calculated using Equation 1.

The addition of N-linked glycosylation sites using the in silico prediction and HTS methods described above increased the in vivo exposure of mice to ENPP1-Fc significantly in two glycoforms—by 4-fold in Construct #1020 and by 7.7-fold in Construct #922 (FIG. 10 and Table 2), and the I256T mutation introduced into Construct #922 additionally increased the half-life by 160%. Residue 256 is close to the catalytic threonine in human ENPP1, which is responsible for the nucleophilic addition onto the phosphoanhydride substrate. Without wishing to be limited by any theory, the sequence variation is present at the analogous site in human ENPP3. This can be a modulator for substrate preference: ENPP2 lacks this loop and can accommodate larger lipid substrates in the catalytic pocket; both ENPP1 and ENPP3 have the loop but only ENPP3 has the N-glycan consensus sequences (N-GCS).

The size of the ENPP1-Fc isoforms in Table 2 were compared by SDS-PAGE gels to determine which sequence variation resulted in increased glycosylation, and showed increases in the molecular weight consistent with the addition of glycosylations. To determine whether the sequence changes in Construct #1020 successfully introduced glycosylations MALDI-TOF was used, which also confirmed the presence of glycosylations at these sites.

Figure 2D:
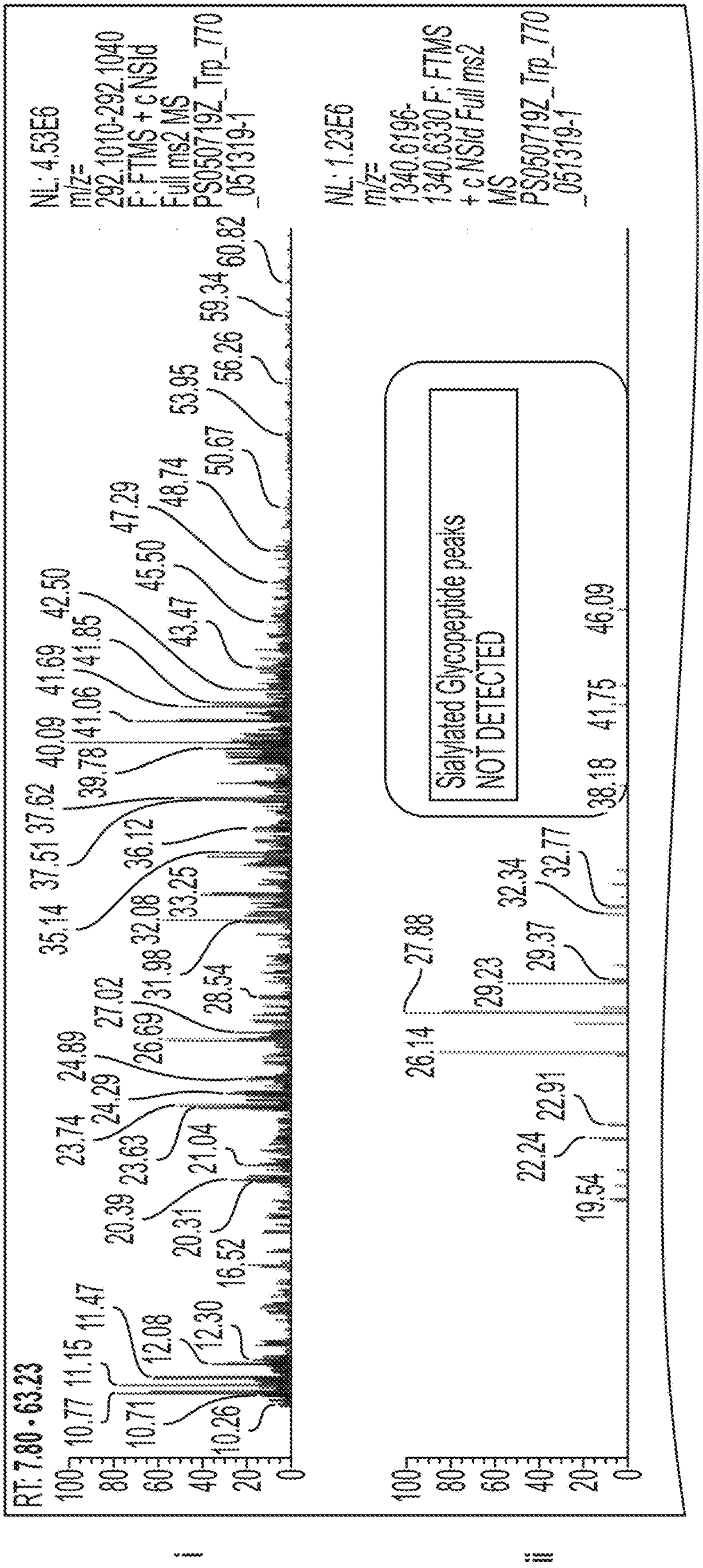
FIG. 2D illustrates mass spectroscopy of the digested peptide fragment $^{241}$SGTFFWPGSDVEINGTFPDIYK$^{262}$ (corresponding to amino acids 219-240 of SEQ ID NO: 11) showing an abundance of sialoglycopeptide peaks (bottom) associated with ENPP1-Fc Clone 19, but not the parent Construct #770.
Figure 2D:
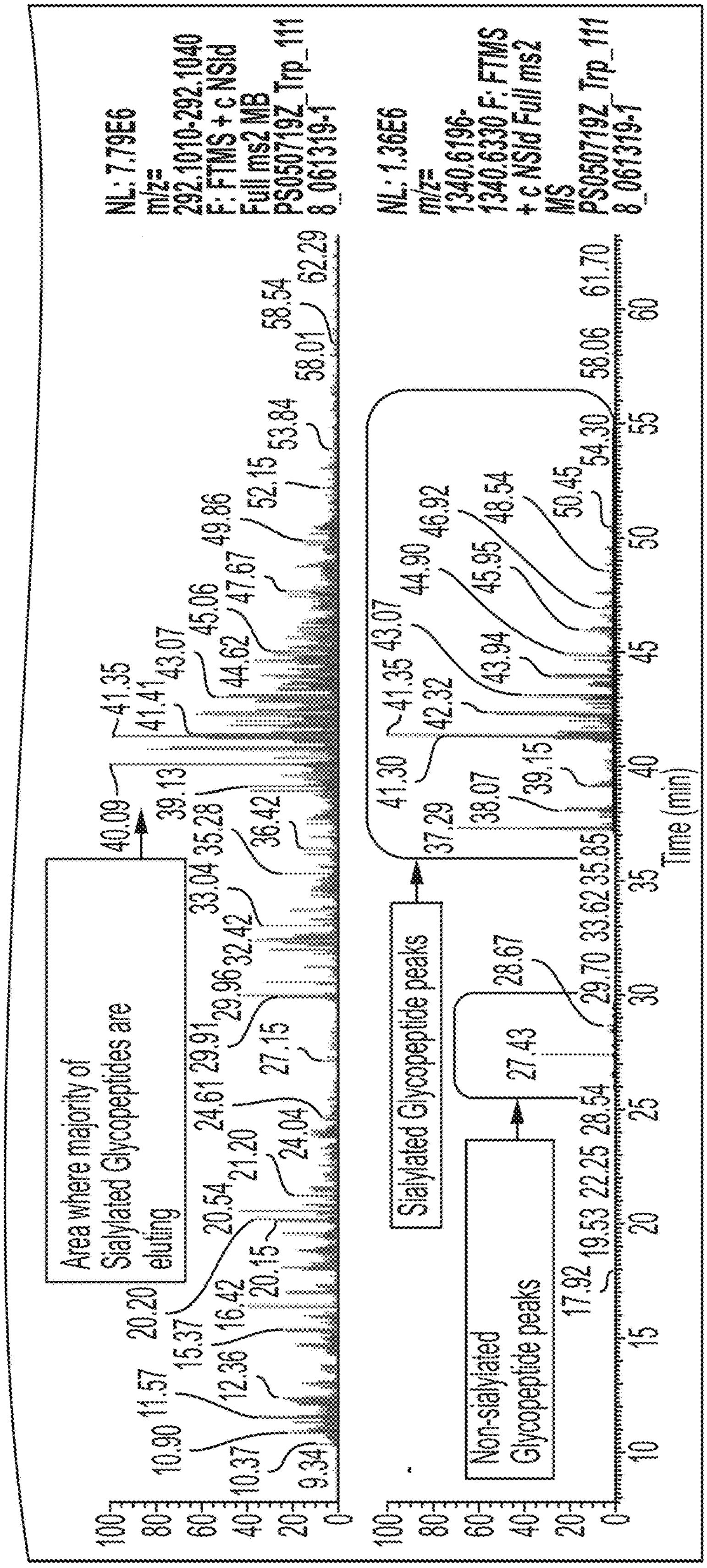

In one aspect, not every N-GCS actually is glycosylated: steric hinderances associated with the position of the N-GCS may occur such that the Asn residue is unable to accept the glycan due to specific flanking amino acids. Therefore, until a purified protein is analyzed for glycan content, one cannot be sure whether any Pk effect of a particular N-GCS is due to the shielding phenomenon of a new glycan or that the amino acid change has altered the kinetics of the enzyme or both. For this reason, any effect on PK to be associated with the N-GCS should be verified by glycan analysis. Mass spectroscopy was used to confirm that ENPP1-Fc Clone 19, which has the I256T mutation located in the digested peptide fragment $^{241}$SGTFFWPGSDVEI$\overline{\text{NGT}}$FPDIYK$^{262}$, is indeed glycosylated at position Asn254, indicated by the abundance of sialoglycopeptide peaks (FIG. 2D), compared to the parent ENPP1-Fc clone which lacks the I256T mutation.

Figure 2E:
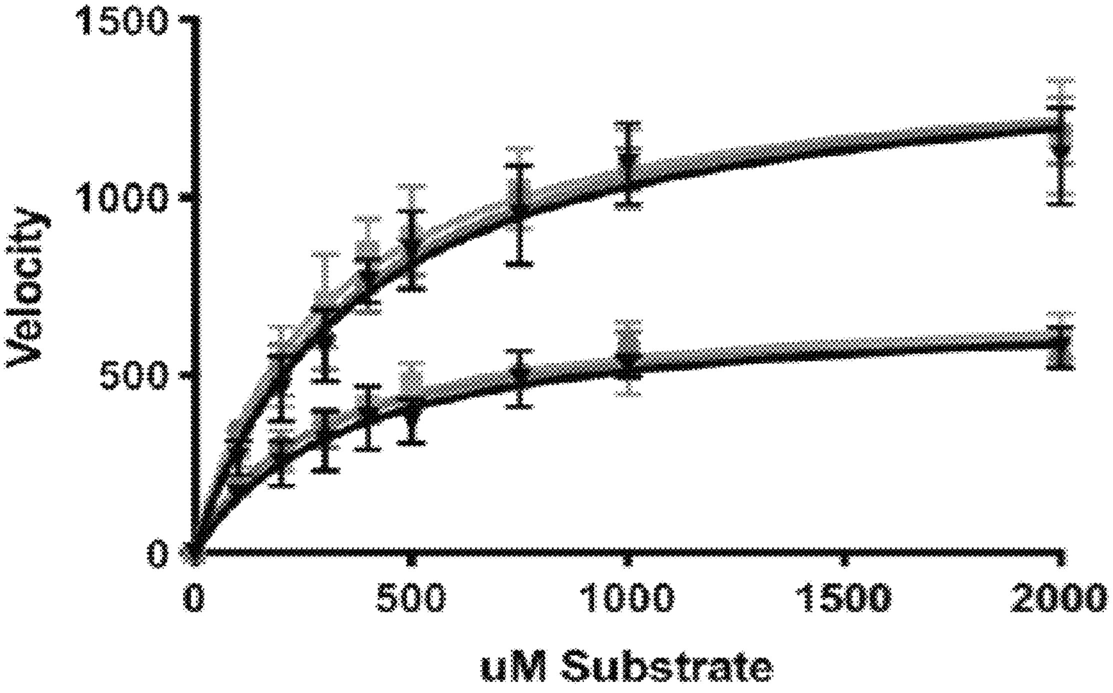
FIG. 2E illustrates the finding that Michaelis-Menten kinetic assays indicate that the velocity of the enzyme at varying substrate concentrations is nearly identical at two different enzyme concentrations for the two I256T containing clones (Clone 17 in yellow, and Clone 19 in red) compared to the parent Construct #770 in black.
Figure 3:
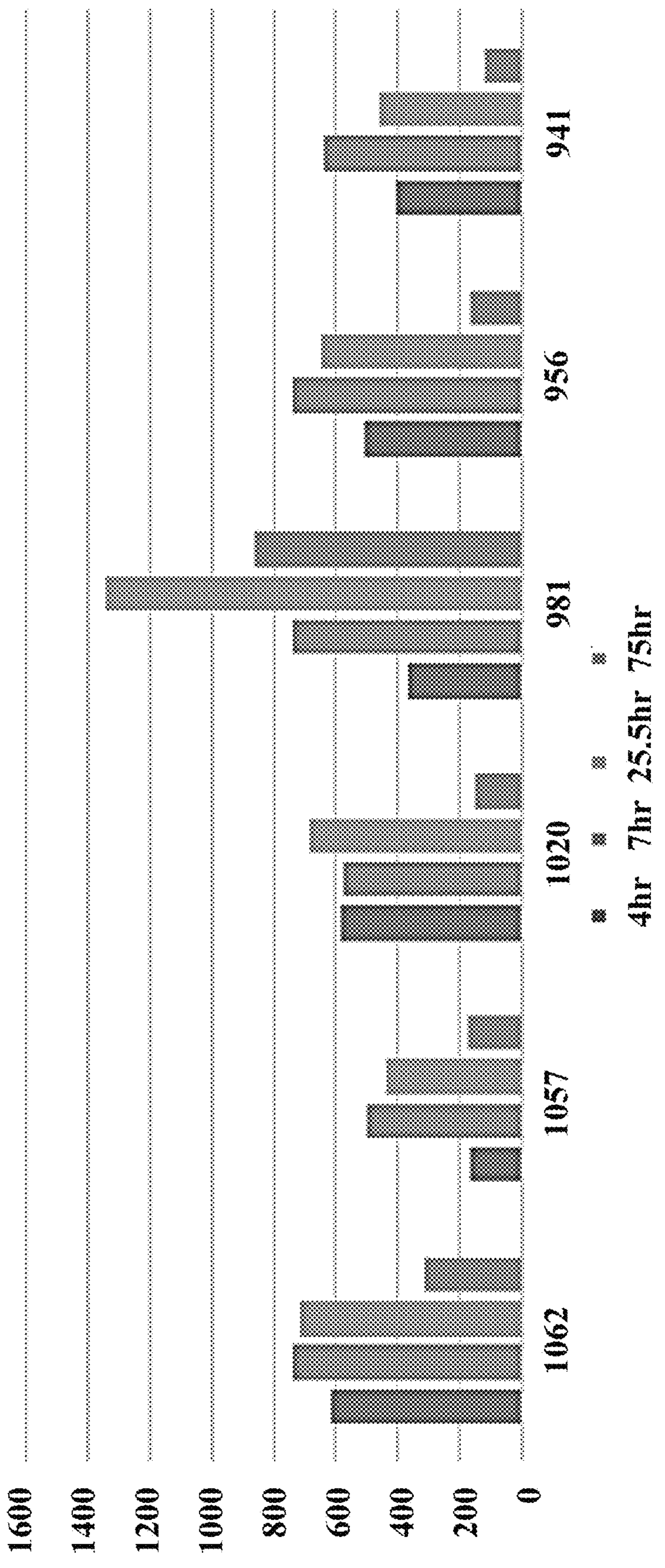
FIG. 3 illustrates a bar graph summarizing plasma phosphodiesterase activity (as measured using the thymidine 5'-monophosphate p-nitrophenyl ester assay, or pNP-TMP assay) after single injection of certain ENPP1 polypeptides in mice (n=3-5). Phosphodiesterase activity in all polypeptides remained elevated after 25 hours, with higher activity at 75 hours observed with Construct #981 (Constructs of interest are outlined in Tables included elsewhere herein).
Figure 4:
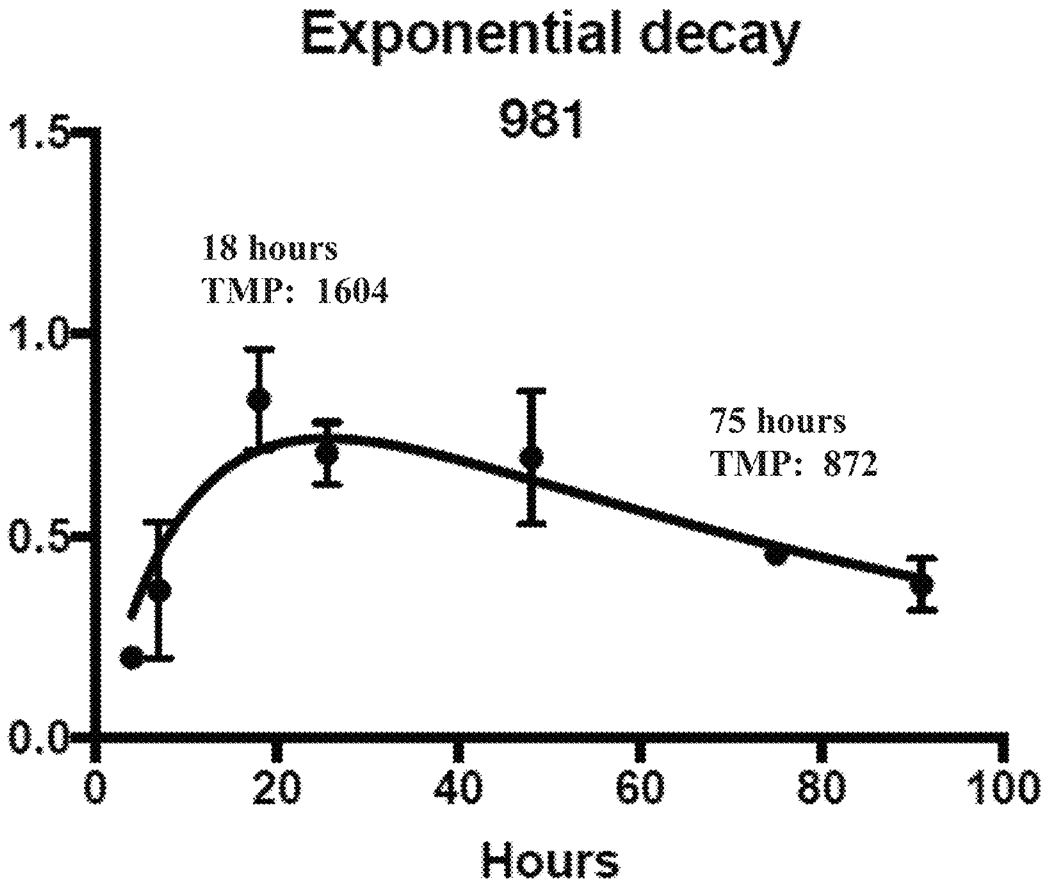
FIG. 4 illustrates in vivo pharmacokinetic data for Construct #981, as measured using the pNP-TMP assay to record enzyme activity in plasma samples of a mouse following subcutaneous injection of the construct. The half-life was estimated to be around 122 hours based on the single subcutaneous bolus injection into 5 mice. Separate experiments to arrive at the half life are described elsewhere herein.
Figure 5:
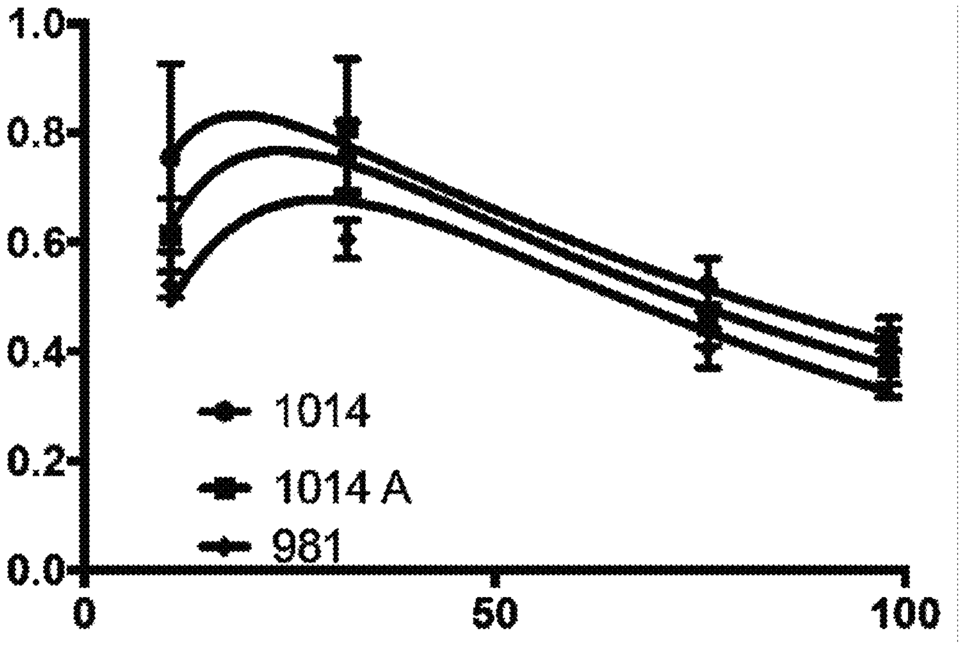
FIG. 5 illustrates selected in vivo pharmacokinetic data for Construct #1014, Construct #1014 prepared in CHO cells grown in culture media supplemented with 1,3,4-O-$Bu_3$ManNAc (denoted as "1014 A" in the graph), and Construct #981. The half-life of constructs can be derived from Equation 1 as described elsewhere herein.
Figure 6:
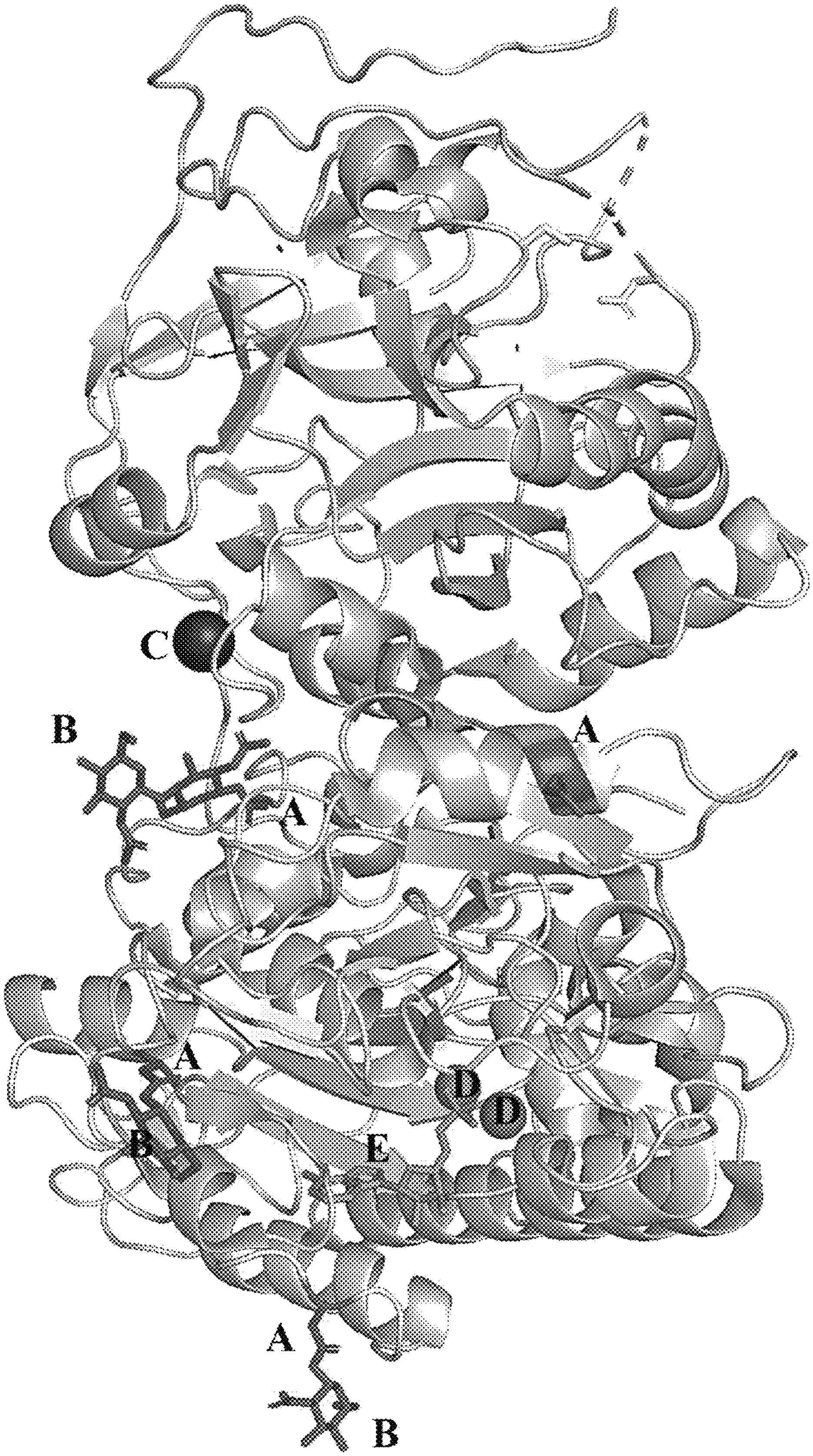
FIG. 6 illustrates three known glycosylation sites in ENPP1, all located in random coil regions: (A)=Asn; (B)=N-acetyl glucosamine. One additional glycosylation site (identified by Surface Glycoprotein Dynamics measurements) is located in Alpha Helix and labeled in red. There is one consensus NLT (Asn Leu Thr) located in PDB area of instability that is yet not known to be glycosylated. There are four more consensus sequences found in hENPP1 whose glycosylation status is unknown. Calcium atom (C); 2 zinc atoms (D); molecule of ATP (E).

To determine whether the 10-fold increase biologic availability resulted from enhancement of the absorption and retention of the biologic or from a gain of function in the enzyme resulting in greater activity within the plasma, the Michaelis-Menten kinetic constants of the parent construct (Construct #770) and that of two I256T containing constructs (Clone 17 and Clone 19) were determined at two different concentrations and no significant differences were observed between the $K_m$ or $K_{cat}$ of either enzyme (FIG. 2E). In certain non-limiting embodiments, increased biologic exposure induced by the addition of a glycan at position 256 relates to increase biologic absorption and/or circulation of the biologic. In certain non-limiting embodiments, increased biologic exposure induced by the addition of a glycan at position 256 is not due to a gain of function of the enzyme.

Figure 11:
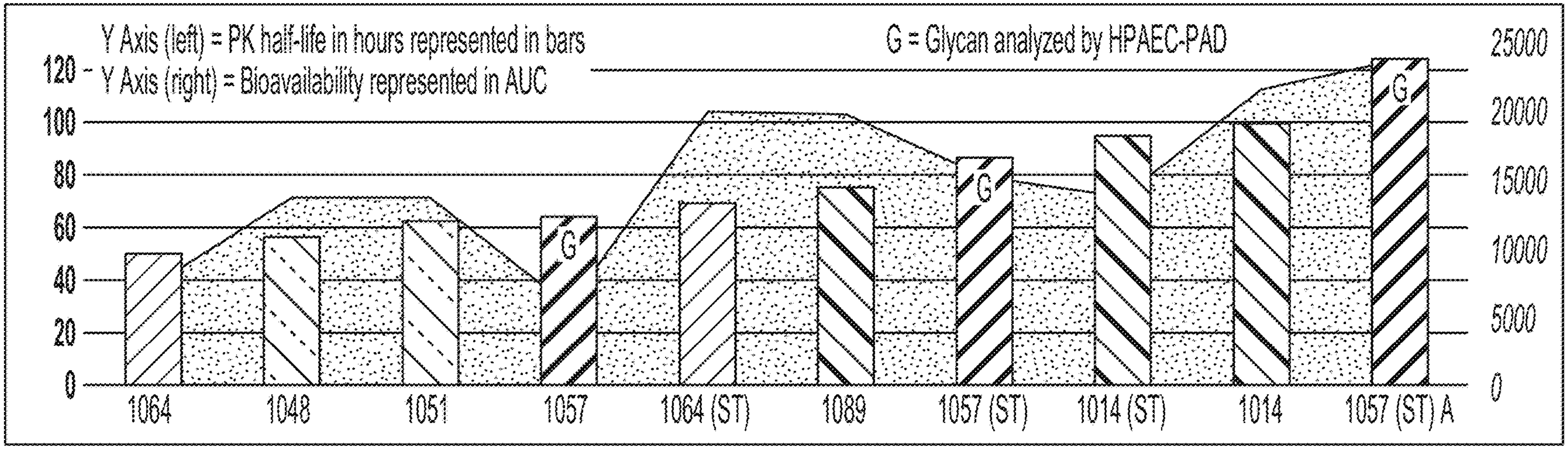
FIG. 11 comprises a graph and a table illustrating the effect of glycosylation and H1064K/N1065F Fc mutations in half-life (PK, in hours) and bioavailability (AUC) of ENPP1 polypeptides. All H1064/N1065-containing Constructs showed improved half-life and AUC values over Construct #770B. Note that Constructs #1048 and #1051 correspond to the same cDNA in two distinct clones, illustrating the reproducibility of the PK/AUC analysis provided herein. Construct #1064 was also grown in cell lines stably transfected with ST6GAL1 (Construct #1064-ST). Construct #1057 was also grown in cell lines stably transfected with ST6GAL1 ("-ST") (Construct #1057-ST) and grown in cell lines stably transfected with ST6GAL1 and supplemented with 1,3,4-O-Bu3-ManNAc ("-A") (Construct #1057-ST-A). Construct #1089 is identical to Construct #1014 but for an added mutation to eliminate a potential trypsin cleavage site. Construct #1014 was also grown in cell lines stably transfected with ST6GAL1 but in this case there was no improvement in PK and bioavailability. PK and bioavailability data are presented in the table, determined as illustrated in FIGS. 4, 5, and 13 and calculated using Equation 1.
Figure 12:
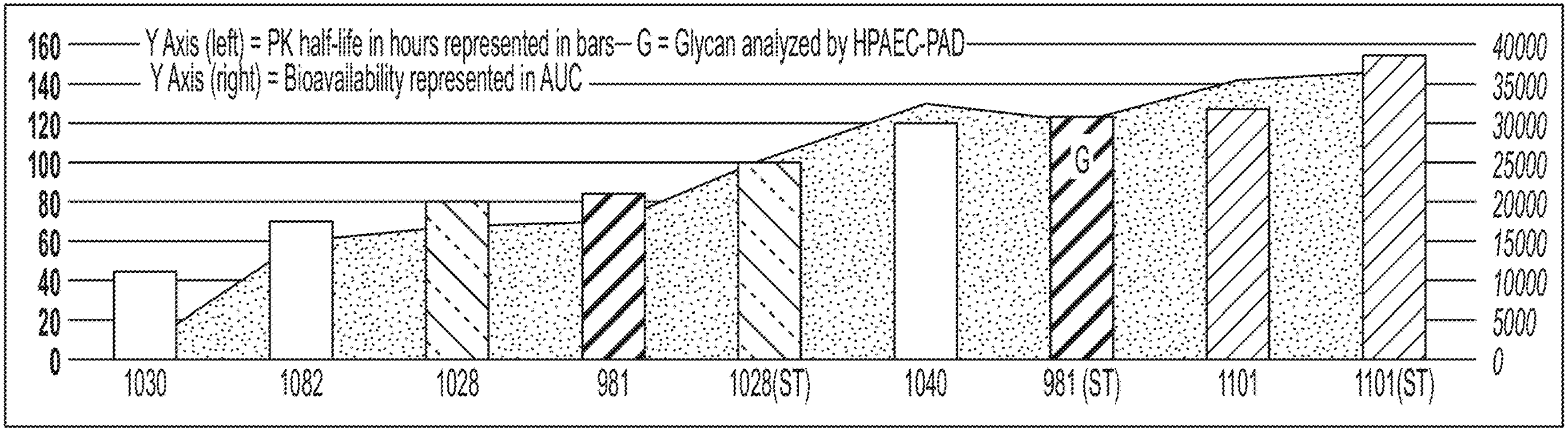
FIG. 12 comprises a graph and a table illustrating the effect of glycosylation and M883Y/S885T/T887E Fc mutation in PK (in terms of half-life, hours) and bioavailability of ENPP1 polypeptides. Construct #1030 has a lower AUC than other Constructs possibly due to the S766N mutation. Constructs #981, #1028, and #1101 showed an increase in both PK and AUC values when grown in cell lines stably transfected with ST6GAL1. Construct #1101 has improved PK and AUC values. PK and bioavailability data are presented in the table, determined as illustrated in FIGS. 4, 5, and 13 and calculated using Equation 1.

Example 4: Pharmacokinetic Effects on Fc IgG1 Mutations (FIGS. 11-12)

Antibodies containing mutations in the Fc domain that enhance their affinity for the FcRn and increase the pH dependent antibody recycling have never been used in therapeutic enzymes fused to the Fc domain. Some Fc mutations successfully increased affinity of the Fc domain for the FcRn receptor but resulted in unfavorable PK properties in antibody PK in vivo, while others were shown to enhance PK properties in vivo.

FcRn is the main homeostatic regulator of human IgG1 Fc serum half-life. To determine whether analogous Fc changes enhance the PK properties of enzyme fusion proteins, two specific IgG1 mutations in Fc previously used in biologic antibodies were investigated-H433K/N434F and M242Y/S254T/T246E. In general, the M242Y/S254T/T246E mutations were found to be superior to H433K/N434F at improving the properties of ENPP1-Fc. For example, Construct #981, possessing only the M242Y/S254T/T246E mutation when compared to Construct #770, increased the half-life by 3.3 fold and the AUC by 5.8 fold. In contrast, constructs with the H433K/N434F mutation in the context of various ENPP1 mutations achieved more modest half-life increases of between 1.2-1.7 fold.

Figure 14A:
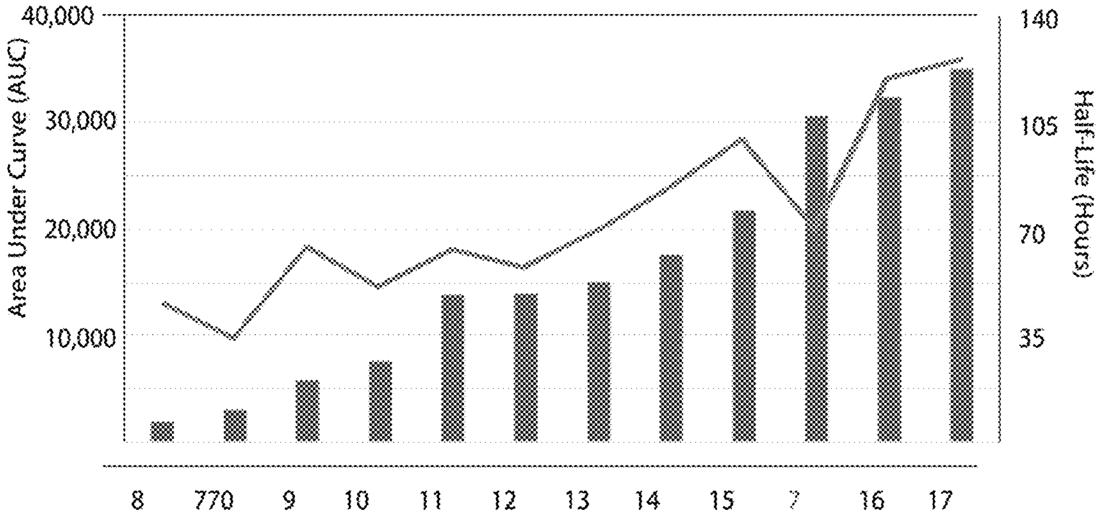
FIG. 14A illustrates pharmacokinetic analysis of clones containing the Fc-HR mutation (Clones 9, 10, 11, 12 and 15) and the Fc-MST mutation (Clones 8, 13, 14, 16, and 17) compared with the parent clone 770 and the 1256T containing Clone 7. The area under the curve (left y-axis) is represented by the bars and the half-life in hours (right y-axis) is represented by the line. Even though Clone 7 has only a modest increase in half-life compared with Clones 16 and 17 (line) it has an almost equivocal AUC (bars) as a result of its greater initial activity after injection.
Figure 14B:
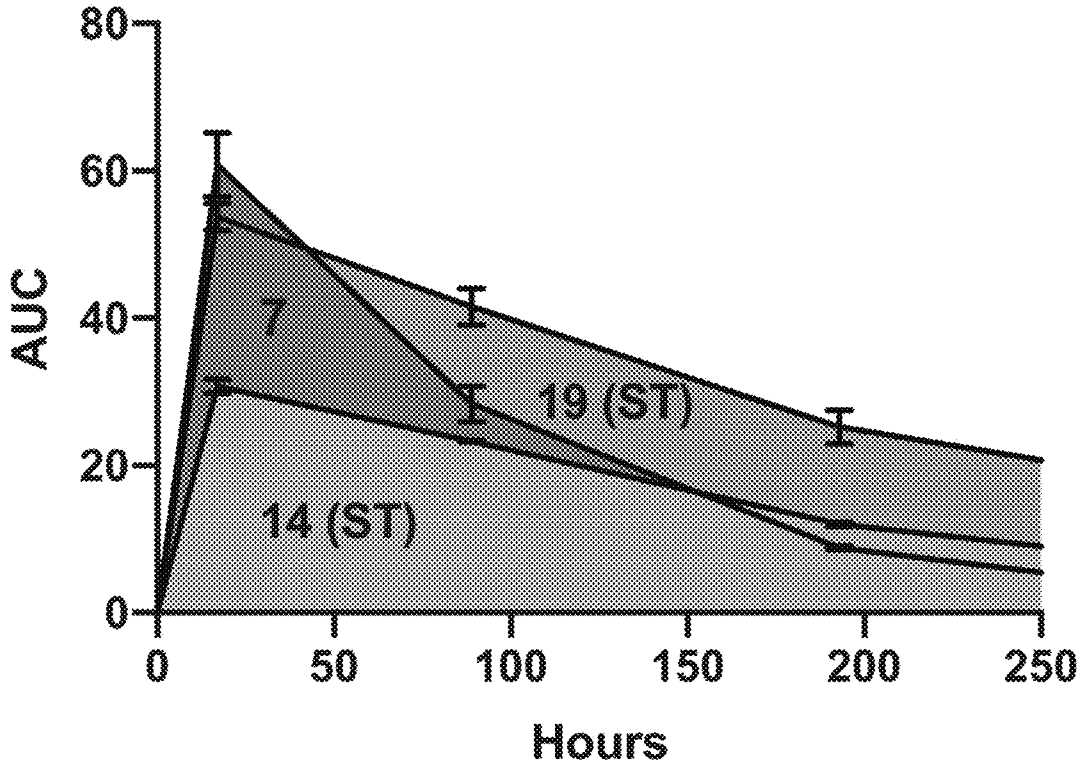
FIG. 14B illustrates biological availability as represented by the slope of the area under the curve. Clone 7, which contains only the I256T mutation, is initially very active in plasma but tappers off quickly, AUC in red. Clone 14-ST, which contains only the Fc MST mutation, is not as active initially as Clone 7 but has a longer half-life indicated by the shallow slope (AUC in gray). Combining the two mutations into one clone, Clone 19-ST with AUC in yellow, yields an enzyme that has both greater initial activity and a longer half-life.
Figure 14C:
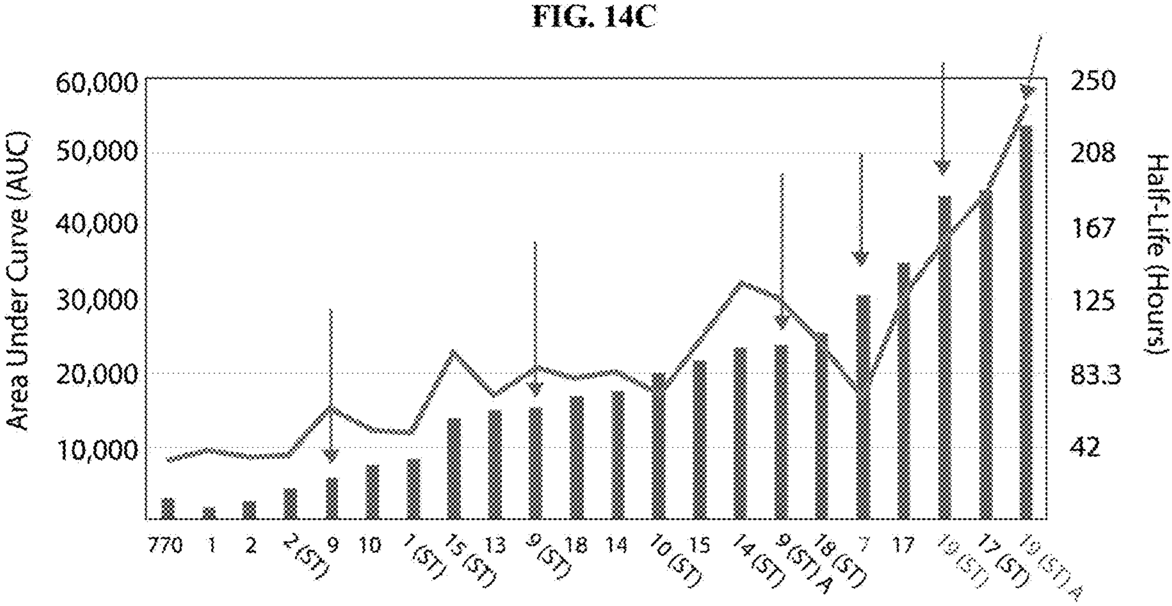
FIG. 14C illustrates AUC (bars, left axis) and half-life in hours (line, right axis) for clones grown in unmodified CHO cells or CHO cells over-expressing α-2,6-sialyltransferase (α-2,6-ST), or CHO cells over-expressing α-2,6-ST combined with 1,3,4-O-$Bu_3$ManNAc supplementation. In all case adding α-2,6-ST (Clones 1, 2, 9, 10, 14, 15, 17 and 18) increased half-life and AUC of the Clone. Clones 9 (3 left arrows) has an increase in AUC and half-life with both CHO cells over-expressing α-2,6-ST, and in CHO over-expressing α-2,6-ST combined with 1,3,4-O-$Bu_3$ManNAc supplementation. Clone 19 compared with Clone 7 (3 right arrows) also has an increase in half-life and AUC associated with 1,3,4-O-$Bu_3$ManNAc supplementation similar to Clone 9.
Figure 14D:
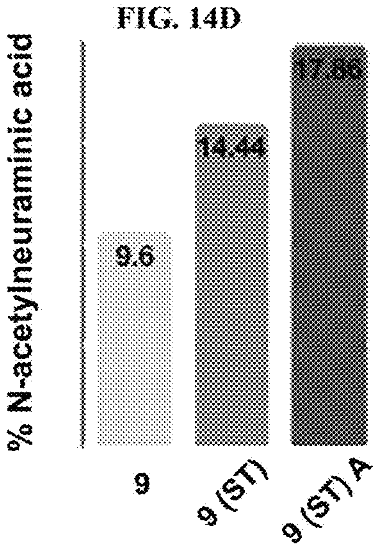
FIG. 14D illustrates the finding that Anion-Exchange Chromatography with Pulsed Amperometric Detection (HPAE-PAD) of Clone 9 grown in CHO K1 cells alone or stably transfected with human α-2,6-ST or a combination of α-2,6-ST and the sialic acid precursor 1,3,4-O-Bu3ManNAc shows a progressive increase in the percentage N-acetylneuraminic acid content with each treatment.
Figure 14E:
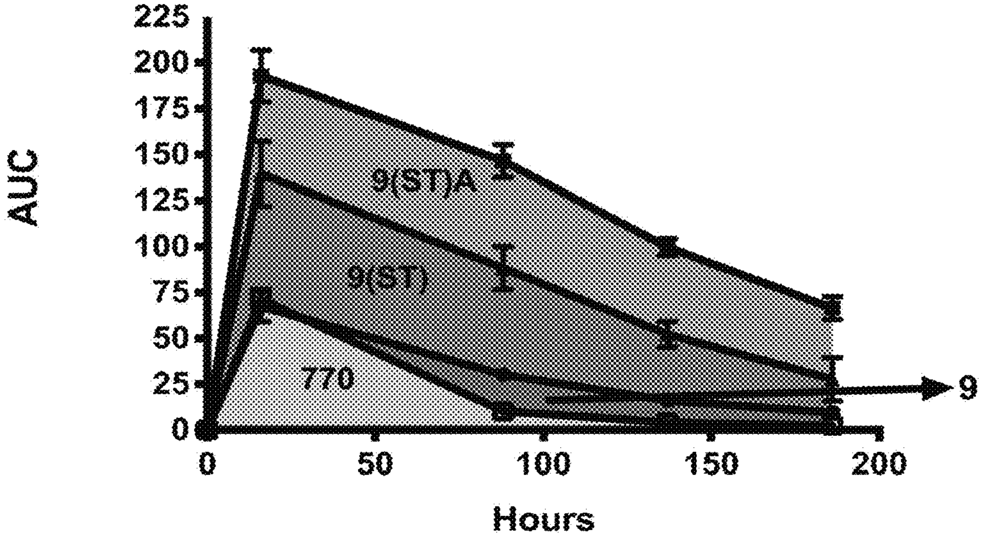
FIG. 14E illustrates AUC pharmacokinetic analysis for parent Construct #770 grown in CHO cell alone (labelled 770) as compared to Clone 9 grown in CHO cells alone (labelled 9), or CHO cell over-expressing α-2,6-ST (labelled 9 (ST)), or CHO cells over-expressing α-2,6-ST combined with 1,3,4-O-$Bu_3$ManNAc supplementation (labelled 9 (ST) A). Clone 9 contains an Fc-HN mutation that provides a mild increase in half-life and AUC over parent clone 770. However, when Clone 9 is grown in CHO cells over-expressing α-2,6-ST or the combination of α-2,6-ST and supplementation with 1,3,4-O-$Bu_3$ManNAc it exhibits a progressively larger increase in AUC and Half-life.

In general, the Fc MST mutation increased biologic exposure to a greater degree than Fc HN mutations (Table 3, FIGS. 14A-14E). For example, adding the MST mutation to the parent isoform increased AUC by 6-fold and half-life by about 2.5 fold, in comparison to the HN mutation which increased AUC by 4.5 fold in the presence of additional glycans (compare Clone14 with Clones 9-12 in Table 3 and FIGS. 14A-14E). However, in some cases specific N-GCS mutations actually decrease bioavailability in the context of specific Fc mutations, i.e., the N-GCS mutation at residue 766 decreases the AUC of MST-Fc containing constructs (compare Clone 8 with Clone 14, Table 3, FIG. 14A) as well as HN-Fc containing constructs (compare Clone 9 with Clone 11, Table 3, FIG. 14A). As a proof of experimental design and reproducibility two independent CHO cell clones were established possessing the same mutations and little variation was found in the pharmacodynamic properties of each (compare clones 11 and 12 in Table 3). Note that the improvement in PK induced by Fc mutation did not rise to the level of improvement attained from the addition of an N-glycan at residue 256, underscoring the importance of select glycosylations on pharmacokinetics. To compare the PK effects of the MST Fc mutation with the effect of the additional glycan at position 256 (via the 1256T mutation) the plasma activity of the ENPP1-Fc isoforms was plotting with time (FIG. 14B). The figure demonstrates that the Fc mutation enhances PK by increasing the half-life of the biologic in the plasma, as demonstrated by the reduced slope of the activity vs time curve in Clone 14 vs. Clone 7. In contrast, the addition of the I256T glycosylation enhances PK by increasing drug absorption into plasma, i.e., increasing $C_{ma}x$, demonstrated by the greater maximal activity present in clone 7 (FIG. 14B). While combining the MST Fc mutation with the 1256T hyperglycosylation only increases overall biologic exposure (AUC) by 16% when compared to the effect of the 1256T glycoform alone, the net effect over the parent isoform is a substantial 11.5 fold, supporting the use of combining both methods to maximize bioavailability (compare Clones 7 and 17, Table 3 and FIG. 14A).

Example 5: Effect of Host Cells and Growth Conditions

Expressing proteins in CHO cells stably transfected with human α-2,6-ST to produce recombinant biologics with terminal sialic acid residues possessing both alpha-2,3 and alpha-2,6 linkages has been used with variable success, with reports of increased and decreased PK properties depending on the biologic. Glycosylation differences between hamsters and humans exist, most notably, human N-linked glycans contain terminal sialic acid residues with both α-2,3 and α-2,6 linkages while CHO cells contain only α-2,3 linkages.

To determine if alpha-2,6 linkages would impact the PK properties of ENPP1-Fc the in vivo exposure (AUC) and half-life of seven ENPP1-Fc isoforms produced in either CHOK1 cells or CHOK1 cells stably transfected with human α-2,6-ST were directly compared (Table 4). A general trend that emerged producing the biologic in CHOK1 cells stably transfected with human α-2,6-ST was beneficial. The strongest effects were noted in exposure of organism to drug (AUC) which demonstrated increases in AUC of 1.7-4.6 fold in the isoforms that responded (Constructs #1057, #1028, #951, #930, and #981). Another trend was that the magnitude of effect in AUC was greater in isoforms with lower initial AUC (Constructs #951 and #1057). However, the effect in the longer acting isoforms (Constructs #1028 and #981) was sizable, yielding AUC values 8-10 fold greater than the parent polypeptide produced in CHOK1 cells.

The effects of α-2,6 linkages on half-life were more modest, with increases of 20-30% in the Constructs that responded. To understand the differential effects of α-2,6 linkages on AUC and half-life protein activity vs time of isoforms produced in CHOk1 cells and 1078 cells were compared.

Figure 13:
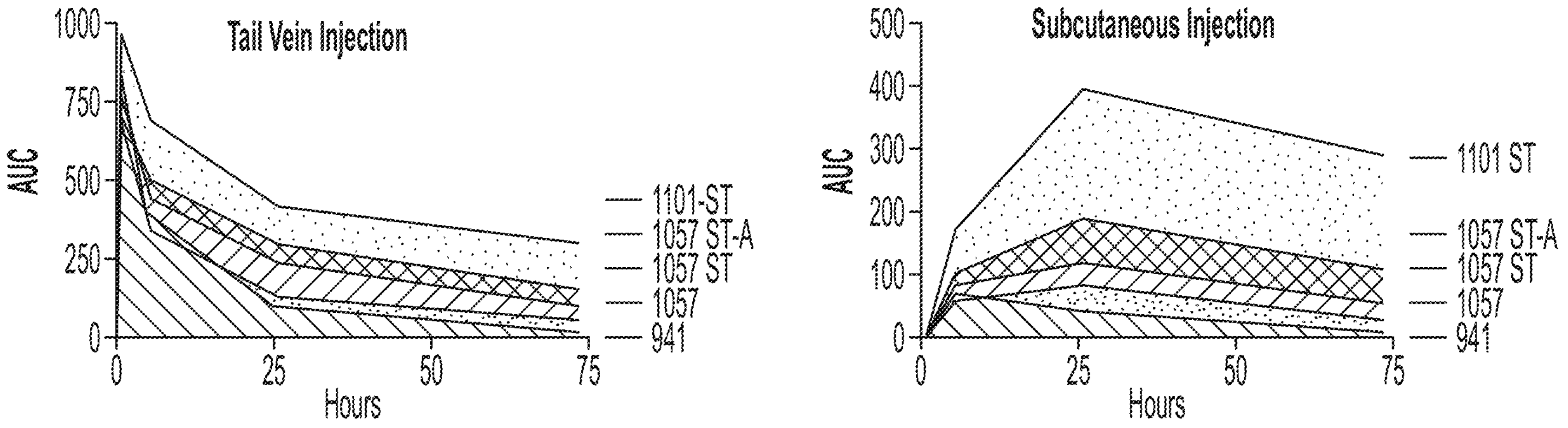
FIG. 13 comprises a set of graphs illustrating the effect of expressing the constructs in CHO cells stably transfected with human α-2,6-ST to produce recombinant biologics with terminal sialic acid residues possessing both alpha-2,3 and alpha-2,6 linkages. These cells are referred to as ST6GAL1 cells or ST cells (denoted as "-ST"). This figure also illustrates the effect of growing constructs in ST6GAL1 cells in the presence of sialic acid, or a high flux precursor of sialic acid known as 1,3,4-O-Bu3-ManNAc (denoted as "-A"). PK and bioavailability data are presented in the table, determined as illustrated in FIGS. 4, 5, and 13 and calculated using Equation 1.

Example 6: Pharmacokinetic Effects of Growth with High-Flux Sialic Acid Precursor To determine the effect of growth conditions on PK properties, culture media of select clones were supplemented with a "high-flux" precursor of sialic acid, 1,3,4-O-$Bu_3$ManNAc, or sialic acid itself. Supplementation of CHOK1 cells with 1,3,4-O-$Bu_3$ManNAc did little to improve the PK properties of ENPP1-Fc, but when the biologic was produced in CHOK1 cells stably transfected with human-2,6-ST, the effects on half-life and AUC were noticeable (FIG. 13 and Table 4). The improvement in PK was primarily due to an increase in systemic resorption of the subcutaneously dosed biologic and not due to an increase in half-life (note the difference in $C_{max}$ of Clones 7 and 14, FIG. 14B).

For example, supplementing cell culture media of CHOK1 cells producing Construct #1014 (Clone 15) with 1,3,4-O-$Bu_3$ManNAc did little to enhance AUC and appeared to degrade the half-life of the isoform.

In contrast, when 1,3,4-O-$Bu_3$ManNAc was added to the cell culture media of Construct #1057 (Clone 9, which possesses two additional glycosylations in the signal sequence and the nuclease domain as well as an HN Fc mutation) produced in CHOK1 cells stably transfected with α-2,6-ST, the effects were more dramatic: the biologic exposure in this clone can be increased 2.6 fold by expressing the clone in CHO cells containing human α-2,6-ST, and an additional 1.4 fold by supplementing the growth media of those cells with sialic acid precursor. These effects yielded net increases in AUC and half-life of 4-fold and 2-fold compared to the same isoform produced in CHOK1 grown in media not supplemented with 1,3,4-O-$Bu_3$ManNAc (FIG. 13 and Table 4). The percentage N-acetylneuraminic acid content of ENPP1-Fc was progressively increased when expressed in CHO K1 cells stably transfected with human α-2,6-ST and grown in the presence of the sialic acid precursor 1,3,4-O-$Bu_3$ManNAc (FIG. 14E), consistent with the notion that one can increase sialic acid content in enzyme biologics by these methods, and that so doing favorably impacts pharmacokinetics.

Figure 15A:
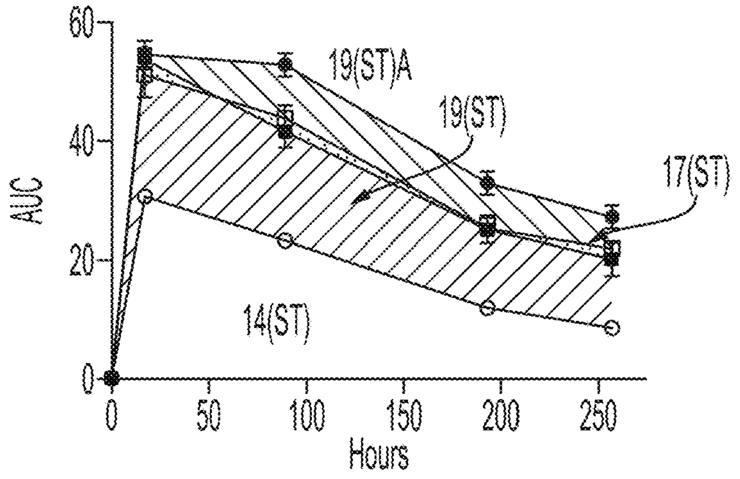
FIG. 15A illustrates AUC pharmacokinetic analysis for Fc-MST containing Clone 14-ST compared with Fc-MST/1256T containing Clones 17-ST, 19-ST, and 19-ST-A. The AUC for Fc-MST containing clones can be further enhanced by the I256T mutation and increased even more when grown in the presence of 1,3,4-O-$Bu_3$ManNAc precursor.
Figure 15B:
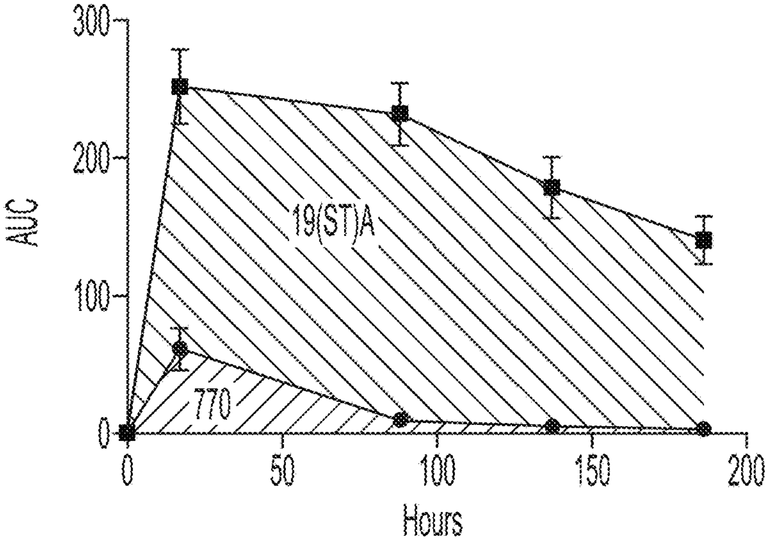
FIG. 15B illustrates AUC pharmacokinetics of the parent Clone 770 compared with Clone 19-ST-A. When Clone 19, which contains both the Fc-MST and I256T mutation is grown in CHO cells over-expressing α-2,6-ST and supplemented with 1,3,4-O-$Bu_3$ManNAc there is a near 18-fold increase in bioavailability.
Figure 15C:
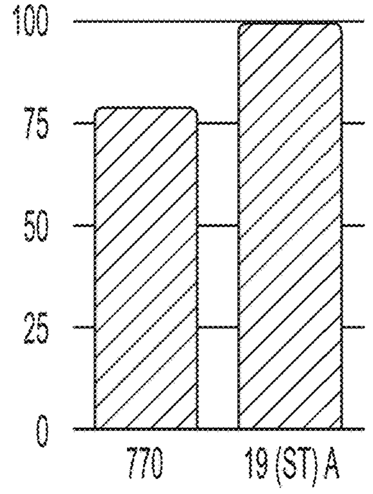
FIG. 15C illustrates the finding that MALDI-TOF/TOF analysis for N-glycan profiling revealed that the % glycans containing sialic acid is higher in Clone 19-ST-A (99.2%) compared to parent Clone 770 (78.4%) when calculated based on the structures that contains at least one galactose for transfer of sialic acid.

The effect of expressing biologic in CHO cells containing human α-2,6-ST alone ranged from as much as 4.5 fold in worst performing isoform (Clone 1 vs Clone 1-ST, Table and FIG. 14C), to more modest effects in the best performing constructs. These modest effects, however, resulted in substantial overall increases, as demonstrated by Clone 17. Expressing Clone 17 in CHO cells containing human α-2,6-ST increased the AUC by a modest 28%, an effect which is nevertheless 3-fold the absolute magnitude of the AUC of the starting clone due to the enhanced nature of these optimized biologics. The final enhancements above Clone 770 are 11.5 fold for Clone 17 and 14.5 fold for Clone 17-ST (Table 5 and FIG. 15A). Eliminating the glycosylations in the signal sequence and nuclease domain in Clone 17 results in no loss of bioavailability, demonstrating that these glycosylations are expendable to the performance of the clone (FIG. 15A, Clones 17-ST and 19-ST). Expressing Clone 19-ST in media containing the sialic acid precursor 1,3,4-O-$Bu_3$ManNAc yielded a very active polypeptide. The increase derived from expressing the protein in growth media containing 1,3,4-O-$Bu_3$ManNAc is represented by the area shaded in dark grey on FIG. 15A, yielding a net increase in bioavailability of nearly 18 fold when compared to the parent construct (FIG. 15B). Mass spectroscopy analysis of the sialyation content in the parent clone and the final product reveals that only 78.4% of the available sites (glycans that have at least one galactose for the transfer of a sialic acid) in the parent clone are sialylated, compared to 99.2% of sites in Clone 19-ST-A (FIG. 15C). The combined findings demonstrate the importance of sialic acid capping of glycosylations in enzyme biologics, and the power of the methods described to enhance the bioavailability of glycan-optimized enzyme biologics.

Example 6: Pharmacokinetic Effects

Figure 15D:
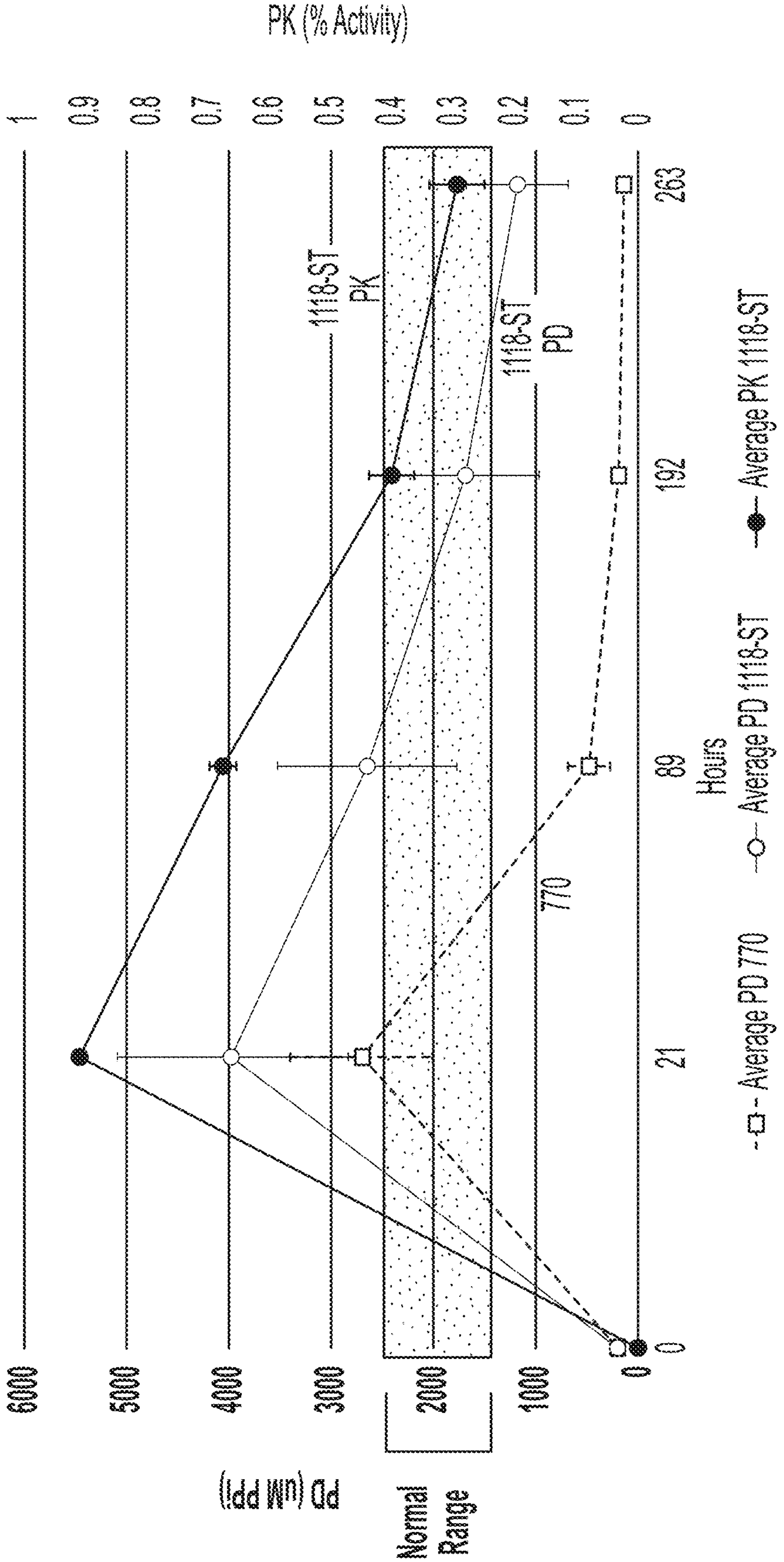
FIG. 15D illustrates the pharmacodynamic effect after a single dose at 0.3 mg/kg of either the parent Clone 770 (red squares) or the optimized ENPP1-Fc Clone 19-ST (red circles), as measured by the generation of PPi (left y-axis) in $Enppl^{asj/asj}$ mice. Physiological levels of PPi in normal mice (shaded grey) is between 1.5 and 2.5 μm PPi while $Enppl^{asj/asj}$ mice have nearly undetectable amounts. A single dose of Clone 770 restores physiological level of PPi that returns baseline before 89 hours, while Clone 19-ST can maintain near physiological levels out to 263 hours. The error bars associated with PPi generation appear much larger than the error bars associate with % activity of the enzyme (right y-axis) (compare red circle vs black circle).

ENPP1-Fc is the only enzyme in mammals capable of generating plasma PPi, and plasma PPi is therefore a biomarker for predicting the efficacy of ENPP1 enzyme replacement therapy in ENPP1 deficiency. To determine the pharmacodynamic effects of the optimized ENPP1-Fc isoform, $Enpp1^{asj/asj}$ mice were dosed with a subcutaneous dose of 0.3 mg/Kg of either Construct #770 or Clone 19-ST and plasma PPi and enzyme presence were measured in plasma for 263 hours (FIG. 15D). Plasma PPi in mice dosed with Construct #770 elevated into the normal range 24 hours after the dose but returned to baseline at 48 hours, while Clone 19-ST elevated plasma PPi to approximately twice the normal range and remains elevated above or in the normal range for approximately 250 hours. These experiments demonstrate that the pharmacokinetic effects observed in the optimized ENPP1-Fc isoforms translate directly into enhanced pharmacodynamic activity.

TABLE 1

| Construct | Mutation | Domain |
|---|---|---|
| 770 | WT | ENPP7 Signal Sequence (aa 1-23) |
| 909 | V29N | |
| Clone 3 (Construct 976) | C25N, K27T | |
| 912 | I70N | SMB Domain (aa 24-109) |
| 914 | R81N | |
| 916 | K97N, D99T | |
| 917 | E115N, P117T | Linker 1 (aa 110-133) |
| 920 | P125T | |
| Clone 7 (Construct 922) | I256T (found in ENPP3, located inside insertion loop) | Insertion Loop (aa 246-265) |
| 923 | A276N/L278T (found in an alpha helix and is confirmed glycosylated in ENPP4 crystal structure) | Catalytic (aa 266-519) |
| 926 | D285N, R287T | |
| 927 | Y364T | |
| Clone 2 (Construct 930) | K369N, I371T | |
| 931 | H409T | |
| 933 | P448L S449T | |
| 936 | P522L, V523T | Linker 2 (aa 520-571) |
| 937 | V523N | |
| 940 | K527N, P529T | |
| 941 | P544L, R545T | |
| 943 | G549T | |
| 944 | P554H (Found in elephant ENPP1) | |
| 948 | P558N, E560T | |
| 952 | P534N, V536T | |
| Clone 1 (Construct 951) | E592N (same position as E668K GACI mutation in humans found in polar bear and armadillo ENPP1) | Endonuclease (aa 572-849) |
| 955 | P643N, S645T | |
| 956 | S766N | |
| 958 | V793N, G795T | |
| 961 | G795N, H797T (Found in mouse Enpp3) | |
| 962 | E864N, L866T | Fc Domain (aa 852-1078) |
| 970 | S885N | |
| 964 | G972N, P974T | |
| 1013 | S1075N, P1076G, G1077T | |
| 975 | H1064K, N1065F | FcRn Neonatal receptor |
| Clone 14 (Construct 981) | M883Y, S885T, T887E | |
| 1014 | V29N; E592N; H1064K, N1065F | N-terminus region; Endonuclease; Fc domain |
| Clone 6 (Construct 1020) | C25N, K27T; E864N, L866T | N-terminus region Fc Domain |
| 1040 | V29N; P534N, V536T; M883Y, S885T, T887E | N-terminus region; Linker 2; Fc domaim |
| 1057 | V29N; S766N; H1064K, N1056F | N-terminus region; Endonuclease; Fc domain |

TABLE 1-continued

| Construct | Mutation | Domain |
|---|---|---|
| 1062 | C25N, K27T; P534N, V536T; H1064K, N1065F | N-terminus region; Linker 2; Fc domain |

TABLE 2

Effect of additional N-linked glycosylation on pharmacokinetics (PK).

| Construct | Mutation | Domain | AUC | Half-Life (hours) |
|---|---|---|---|---|
| 770 | None | | 3,027 | 34.2 |
| 970 | S885N | Fc | | |
| 956 | S766N | Endonuclease | | |
| 941 | P544L, R545T | Endonuclease | | |
| 951 (Clone 1) | E592N | Endonuclease | 1,789 | 40 |
| 930 (Clone 2) | K369N, I371T | Catalytic | 2,545 | 35.4 |
| 976 (Clone 3) | C25N, K27T | N-terminus region | 3,636 | 36.4 |
| 1047 (Clone 4) | V29N; E864N, L866T | N-terminus region & Linker | 4,373 | 37.6 |
| 1024 (Clone 5) | C25N, K27T; S766N | N-terminus region & Endonuclease | 4,537 | 34.9 |
| 1020 (Clone 6) | C25N, K27T; E864N, L866T | N-terminus region & Linker | 12,829 | 37 |
| 922 (Clone 7) | I256T | Catalytic | 30,570 | 69 |

TABLE 3

Effect of Fc mutations on pharmacokinetics (PK).

| Construct | Mutation | Glycan Domain | AUC | Half-Life (hours) |
|---|---|---|---|---|
| 770 | None | | 3,027 | 34.2 |
| 1062 | C25N, K27T; P534N, V536T; H1064K, N1065F | N-terminus region & Endonuclease | | |
| 1063 | C25N, K27T; E864N, L866T; H1064K, N1065F | N-terminus region & Endonuclease | | |
| 1030 (Clone 8) | S766N; M883Y, S885T, T887E | Endonuclease | 1,912 | 45.4 |
| 1057 (Clone 9) | V29N; S766N; H1064K, N1065F | N-terminus region & Endonuclease | 5,826 | 64.6 |
| 1064 (Clone 10) | C25N, K27T; S766N, H1064K, N1065F | N-terminus region & Endonuclease | 7,540 | 50.6 |
| 1051 (Clone 11) | V29N H106K, N1065F | N-terminus region & Endonuclease | 13,918 | 57.1 |
| 1082 (Clone 13) | V29N; E592N; M883Y, S885T, T887E | Endonuclease | 14,978 | 70 |
| 1028 | E592N; M883Y, S885T, T887E | Endonuclease | 16,932 | 80.1 |
| 981 (Clone 14) | M883Y, S885T, T887E | None | 17,587 | 84 |
| 1014 (Clone 15) | V29N; E592N; H1064K, N1065F | N-terminus region & Endonuclease | 21,752 | 99.9 |
| 1040 (Clone 16) | V29N; P534N, V536T; M883Y, S885T, T887E | N-terminus region & Endonuclease | 32,391 | 119.4 |
| 1101 (Clone 17) | V29N; I256T; M883Y, S885T, T887E | N-terminus region & Catalytic | 35,021 | 126.3 |

TABLE 4

Effect of cell lines and mutations on pharmacokinetics (PK). Those Constructs marked as "-ST" were prepared using a modified CHO cells line stably transfected with human α-2,6-sialytransferase (α-2,6-ST); this enhances the amount of sialyation of the fusion protein when compared with the fusion protein expressed in normal CHO cell lines. Enhanced sialyation of the Constructs resulted in improvements in AUC and half-life values.

| Construct | Mutation | Domain | AUC | Half-Life (hours) |
|---|---|---|---|---|
| 770 | None | | 3,027 | 34.2 |
| 1057 (Clone 9) | V29N; S766N; H1064K, N1065F | N-terminus region & Endonuclease | 5,826 | 64.6 |
| 1057-ST (Clone 9-ST) | V29N; S766N H1064K, N1065F | N-terminus region & Endonuclease | 15,337 | 87.4 |
| 1028 (Clone 18) | E592N M883Y, S885T, T887E | Endonuclease | 16,932 | 80.1 |
| 1028-ST (Clone 18-ST) | E592N M883Y, S885T, T887E | Endonuclease | 25,500 | 100 |
| 951 (Clone 1) | E592N | Endonuclease | 1,789 | 40 |
| 951-ST (Clone 1-ST) | E592N | Endonuclease | 8,379 | 49.3 |
| 930 (Clone 2) | K369N, I371T | Catalytic | 2,545 | 35.4 |
| 930-ST (Clone 2-ST) | K369N, I371T | Catalytic | 4,407 | 36.3 |
| 981 (Clone 14) | M883Y, S885T, T887E | None | 17,587 | 122.5 |
| 981-ST (Clone 14-ST) | M883Y, S885T, T887E | None | 30,021 | 122.5 |
| 1014 (Clone 15) | V29N; E592N; H1064K, N1065F | N-terminus region & Endonuclease | 21,752 | 99.9 |
| 1014-ST (Clone 15-ST) | V29N; E592N H1064K, N1065F | N-terminus region & Endonuclease | 13,882 | 96.2 |
| 1101 (Clone 17) | V29N; I256T M883Y, S885T, T887E | N-terminus region & Catalytic | 35,021 | 126.3 |
| 1101-ST (Clone 17-ST) | V29N; I256T M883Y, S885T, T887E | N-terminus region & Catalytic | 37,239 | 152.9 |
| 1064 (Clone 10) | C25N, K27T; S766N; H1064K, N1065F | Signal sequence, Nuclease domain, Fc domain | 7,540 | 50.6 |
| 1064-ST (Clone 10) | C25N, K27T; S766N; H1064K, N1065F | Signal sequence, Nuclease domain, Fc domain | 20,062 | 70.1 |
| 1082 (Clone 13) | V29N; E592N; M883Y, S885T, T887E | Signal sequence, Nuclease domain, Fc domain | 14,978 | 70 |
| 922 (Clone 7) | I256T | Catalytic domain | 30,570 | 69 |

TABLE 5

Effect of sialic acid supplementation on pharmacokinetics (PK). Those Constructs marked as "-ST" were prepared using a modified CHO cells line stably transfected with human α-2,6-sialytransferase (α-2,6-ST); this enhances the amount of sialyation of the fusion protein when compared with the fusion protein expressed in normal CHO cell lines. Those Constructs marked as "-A" were prepared in cells grown in culture media supplemented with 1,3,4-O-$Bu_3$ManNAc, a "high-flux" precursor of sialic acid, during protein production.

| Construct | Mutation | Domain | AUC | Half-Life (hours) |
|---|---|---|---|---|
| 1057 | V29N; S766N; H1064K, N1065F | N-terminus region & Endonuclease | 5,826 | 64.6 |
| 1057-ST | V29N; S766N; H1064K/N1065F | N-terminus region & Endonuclease | 15,337 | 87.4 |
| 1057-ST-A | V29N; S766N; H1064K/N1065F | N-terminus region & Endonuclease | 23,867 | 124.9 |
| 1014 | V29N; E592N; H1064K/N1065F | N-terminus region & Endonuclease | 21,752 | 99.9 |
| 1014-A | V29N; E592N; H1064K/N1065F | N-terminus region & Endonuclease | | |
| 1101 | V29N; I256T M883Y/S885T/T887E | N-terminus region & Catalytic | 35,021 | 126.3 |
| 1101-A | V29N; I256T M883Y/S885T/T887E | N-terminus region & Catalytic | 37,239 | 152.9 |
| 1118-ST (Clone 19) | I256T; M883Y, S885T, T887E | Catalytic domain; Fc domain | 44,085 | 159 |
| 1118-ST-A (Clone 19) | I256T; M883Y, S885T, T887E | Catalytic domain; Fc domain | 53,620 | 235 |

TABLE 6

List of polypeptides and corresponding mutations

| Polypeptide | Region of Mutation | Mutated Residues |
|---|---|---|
| 970 | Fc | S885N |
| 956 | Endonuclease | S766N |
| 981 | Fc | M883Y, S885T, T887E |
| 1020 | N terminal region and linker region | C25N, K27T, E864N, L866T |
| 1062 | N terminal, Endonuclease, and Fc | C25N, K27T, P534N, V536T, H1064K, N1065F |
| 941 | Endonuclease | P554L and R545T |
| 1057 | N terminal, Endonuclease and Fc | V29N, S766N, H1064K, N1065F |
| 1014 | N terminal, Endonuclease and Fc | V29N, E592N, H1064K, N1065F |
| 1040 | N terminal, Endonuclease and Fc | V29N, P534N, V536T, M883Y, S885T, T887E |
| 930 | Catalytic | K369N and I371T |
| 951 | Endonuclease | E592N |
| 976 | N terminal | C25N, K27T |
| 1024 | N terminal and Endonuclease | C25N, K27T, S766N |
| 1028 | Endonuclease and Fc | E592N, M883Y, S885T, T887E |
| 1030 | Endonuclease and Fc | S766N, M883Y, S885T, T887E |
| 1047 | N terminal and linker region | V29N, E864N, L866T |
| 1051 | N terminal and Fc | V29N, H1064K, N1065F |
| 1062 | N terminal region, Endonuclease and Fc | C25N, K27T, P534N, V536T, H1064K, N1065F |
| 1063 | N terminal region, linker and Fc | C25N, K27T, E864N, L866T, H1064K, N1065F |
| 1064 | N terminal region, Endonuclease and Fc | C25N, K27T/S766N/H1064K, N1065F |

TABLE 6-continued

| List of polypeptides and corresponding mutations | | |
|---|---|---|
| Polypeptide | Region of Mutation | Mutated Residues |
| 1082 | N terminal region, Endonuclease and Fc | V29N, E592N, M883Y, S885T, T887E |
| 1089 | N terminal region, Endonuclease, Trypsin KO and Fc | V29N, E592N, R741A, H1064K, N1065F |

TABLE 7

| List of mutations in ENPP1 polypeptide Residue of Mutation |
|---|
| C25N |
| K27T |
| V29N |
| E115N |
| P117T |
| P125T |
| A276N |
| L278T |
| D285N |
| R287T |
| Y364T |
| K369N |
| I371T |
| H409T |
| P448L |
| S449T |
| P521L |
| V522T |
| V522N |
| K526N |
| P528T |
| P534N |
| V536T |
| P543L |
| R544T |
| R545T |
| G548T |
| P554H |
| P554L |
| P558N |
| E560T |
| E591N |
| E592K |
| E592N |
| P643T |
| S645T |
| S765N |
| S766N |
| S885N |
| R741A |
| V793N |
| H794S |
| G795T |
| G795N |
| H797T |
| E864N |
| L866T |
| H1064K |
| N1065K |
| M883Y |
| S885T |
| T887E |
| M1059L |
| N1065S |
| I884A |
| H941A |
| H1066A |

ENUMERATED EMBODIMENTS

The following exemplary embodiments are provided, the numbering of which is not to be construed as designating levels of importance.

Embodiment 1 provides an ENPP1 polypeptide fusion comprising an ENPP1 polypeptide fused to a Fc region of an immunoglobulin, wherein the ENPP1 polypeptide comprises the mutation I256T as relating to SEQ ID NO:7.

Embodiment 2 provides the polypeptide fusion of Embodiment 1, wherein the Fc region comprises at least one mutation selected from the group consisting of M883Y, S885N, S885T, T887E, H1064K, and N1065F as relating to SEQ ID NO:7.

Embodiment 3 provides the polypeptide fusion of Embodiment 1, wherein the Fc region comprises at least one mutation selected from the group consisting of S885N, M883Y, M883Y/S885T/T887E, and H1064K/N1065F as relating to SEQ ID NO:7.

Embodiment 4 provides the polypeptide fusion of any of Embodiments 1-3, wherein the ENPP1 polypeptide further comprises at least one mutation selected from the group consisting of C25N, K27T, and V29N as relating to SEQ ID NO:7.

Embodiment 5 provides the polypeptide fusion of any of Embodiments 1-4, wherein the ENPP1 polypeptide comprises at least one mutation selected from the group consisting of C25N/K27T and V29N as relating to SEQ ID NO:7.

Embodiment 6 provides the polypeptide fusion of any of Embodiments 1-5, wherein the ENPP1 polypeptide further comprises at least one mutation selected from the group consisting of K369N, and I371T as relating to SEQ ID NO:7.

Embodiment 7 provides the polypeptide fusion of any of Embodiments 1-6, wherein the ENPP1 polypeptide comprises the mutation K369N/I371T as relating to SEQ ID NO:7.

Embodiment 8 provides the polypeptide fusion of any of Embodiments 1-7, wherein the ENPP1 polypeptide further comprises at least one mutation selected from the group consisting of P534N, V536T, R545T, P554L, E592N, R741D, and S766N as relating to SEQ ID NO: 7.

Embodiment 9 provides the polypeptide fusion of any of Embodiments 1-8, wherein the ENPP1 polypeptide comprises at least one mutation selected from the group consisting of P534N/V536T, P554L/R545T, E592N, E592N/R741D, and S766N as relating to SEQ ID NO: 7.

Embodiment 10 provides the polypeptide fusion of any of Embodiments 1-9, wherein the ENPP1 polypeptide further comprises at least one mutation selected from the group consisting of E864N and L866T as relating to SEQ ID NO:7.

Embodiment 11 provides the polypeptide fusion of any of Embodiments 1-10, wherein the ENPP1 polypeptide comprises at least the mutation E864N/L866T as relating to SEQ ID NO:7.

Embodiment 12 provides the polypeptide fusion of any of Embodiments 1-11, comprising at least one mutation selected from the group consisting of C25N, K27T, V29N, C25N/K27T, K369N, I371T, K369N/I371T, P534N, V536T, R545T, P554L, E592N, R741D, S766N, P534N/V536T, P554L/R545T, E592N/R741D, E864N, L866T, E864N/L866T, M883Y, S885N, S885T, T887E, H1064K, N1065F, M883Y/S885T/T887E, H1064K/N1065F as relating to SEQ ID NO:7.

Embodiment 13 provides the polypeptide fusion of any of Embodiments 1-12, wherein the Fc region is of an IgG.

Embodiment 14 provides the polypeptide fusion of any of Embodiments 1-13, comprising at least one mutation selected from the group consisting of P534N, V536T, R545T, P554L, S766N, and E592N as relating to SEQ ID NO:7.

Embodiment 15 provides the polypeptide fusion of any of Embodiments 1-13, comprising at least one mutation selected from the group consisting of S766N, P534N/Y536T, P554L/R545T, and E592N as relating to SEQ ID NO:7.

Embodiment 16 provides the polypeptide fusion of any of Embodiments 1-13, comprising at least one mutation selected from the group consisting of S885N, S766N, M883Y/S885T/T887E, E864N/L866T, P534N/V536T/H1064K/N1065F, P554L/R545T, S766N/H1064K/N1065F, E592N/H1064K/N1065F, and P534N/V536T/M883Y/S885T/T887E as relating to SEQ ID NO:7.

Embodiment 17 provides an ENPP1 polypeptide fusion comprising an ENPP1 polypeptide and a Fc region of an immunoglobulin, the polypeptide fusion comprising mutations I256T, M883Y, S885T, and T887E as relating to SEQ ID NO:7.

Embodiment 18 provides an ENPP1 polypeptide fusion comprising an ENPP1 polypeptide and a Fc region of an immunoglobulin, the polypeptide fusion comprising mutations I256T, P534N, V536T, M883Y, S885T, and T887E as relating to SEQ ID NO:7.

Embodiment 19 provides an ENPP1 polypeptide fusion comprising an ENPP1 polypeptide and a Fc region of an immunoglobulin, the polypeptide fusion comprising mutations I256T, E592N, H1064K, and N1065F as relating to SEQ ID NO:7.

Embodiment 20 provides an ENPP1 mutant polypeptide comprising amino acids 23-849 of SEQ ID NO:7, wherein the mutant polypeptide comprises mutation I256T and further comprises a mutation selected from the group consisting of S766N, P534N, V536T, P554L, R545T, and E592N as relating to SEQ ID NO:7.

Embodiment 21 provides the mutant polypeptide of Embodiment 20, which comprises the amino acid sequence of SEQ ID NO:7.

Embodiment 22 provides the mutant polypeptide of any of Embodiments 20-21, which comprises the amino acid sequence of SEQ ID NO:7. Embodiment 23 provides the mutant polypeptide of any of Embodiments 20-23, wherein the mutant polypeptide comprises at least one mutation selected from the group consisting of S766N, P534N/V536T, P554L/R545T, and E592N as relating to SEQ ID NO:7.

Embodiment 24 provides the mutant polypeptide of any of Embodiments 21-23, comprising mutations selected from the group consisting of: S885N, S766N, M883Y/S885T/T887E, P534N/V536T/H1064K/N1065F, P554L/R545T, S766N/H1064K/N1065F, E592N/H1064K/N1065F, and P534N/V536T/M883Y/S885T/T887E as relating to SEQ ID NO:7.

Embodiment 25 provides the mutant polypeptide of any of Embodiments 21-24, comprising a S885N mutation as relating to SEQ ID NO:7.

Embodiment 26 provides the mutant polypeptide of any of Embodiments 20-25, comprising a S766N mutation as relating to SEQ ID NO:7.

Embodiment 27 provides the mutant polypeptide of any of Embodiments 21-26, comprising mutations M883Y, S885T, and T887E as relating to SEQ ID NO:7.

Embodiment 28 provides the mutant polypeptide of any of Embodiments 21-27, comprising mutations P534N, V536T, H1064K, and N1065F as relating to SEQ ID NO:7.

Embodiment 29 provides the mutant polypeptide of any of Embodiments 20-28, comprising mutations P554L and R545T as relating to SEQ ID NO:7.

Embodiment 30 provides the mutant polypeptide of any of Embodiments 21-29, comprising mutation S766N, H1064K, and N1065F as relating to SEQ ID NO:7.

Embodiment 31 provides the mutant polypeptide of any of Embodiments 21-30, comprising mutation E592N, H1064K, and N1065F as relating to SEQ ID NO:7.

Embodiment 32 provides the mutant polypeptide of any of Embodiments 21-31, comprising mutations P534N, V536T, M883Y, S885T, and T887E as relating to SEQ ID NO: 7.

Embodiment 33 provides the polypeptide fusion of any of Embodiments 1-19 or the mutant polypeptide of any of Embodiments 20-32, which is expressed from a CHO cell line stably transfected with human ST6 beta-galactoside alpha-2,6-sialyltransferase (also known as ST6GAL1).

Embodiment 34 provides the polypeptide fusion of any of Embodiments 1-19 or the mutant polypeptide of any of Embodiments 20-32, which is grown in a cell culture supplemented with sialic acid and/or N-acetylmannosamine (also known as 1,3,4-O-Bu3ManNAc).

Embodiment 35 provides a method of reducing or preventing progression of pathological calcification in a subject in need thereof, the method comprising administering to the subject a therapeutically effective amount of the polypeptide fusion of any of Embodiments 1-19 and 33-34 or the mutant polypeptide of any of Embodiments 20-34.

Embodiment 36 provides a method of reducing or preventing progression of pathological ossification in a subject in need thereof, the method comprising administering to the subject a therapeutically effective amount of the polypeptide fusion of any of Embodiments 1-19 and 33-34 or the mutant polypeptide of any of Embodiments 20-34.

Embodiment 37 provides a method of reducing or preventing progression of ectopic calcification of soft tissue in a subject in need thereof, the method comprising administering to the subject a therapeutically effective amount of the polypeptide fusion of any of Embodiments 1-19 and 33-34 or the mutant polypeptide of any of Embodiments 20-34.

Embodiment 38 provides a method of treating, reversing, or preventing progression of ossification of the posterior longitudinal ligament (OPLL) in a subject in need thereof, the method comprising administering to the subject a therapeutically effective amount of the polypeptide fusion of any of Embodiments 1-19 and 33-34 or the mutant polypeptide of any of Embodiments 20-34.

Embodiment 39 provides a method of treating, reverting, or preventing progression of hypophosphatemic rickets in a subject in need thereof, the method comprising administering to the subject a therapeutically effective amount of the polypeptide fusion of any of Embodiments 1-19 and 33-34 or the mutant polypeptide of any of Embodiments 20-34.

Embodiment 40 provides a method of reducing or preventing progression of at least one disease selected from the group consisting of chronic kidney disease (CKD), end stage renal disease (ESRD), calcific uremic arteriolopathy (CUA), calciphylaxis, ossification of the posterior longitudinal ligament (OPLL), hypophosphatemic rickets, osteoarthritis, aging related hardening of arteries, idiopathic infantile arterial calcification (IIAC), Generalized Arterial Calcification of Infancy (GACI), and calcification of atherosclerotic plaques in a subject diagnosed with the at least one disease, the method comprising administering to the subject a therapeutically effective amount of the polypeptide fusion of any of Embodiments 1-19 and 33-34 or the mutant polypeptide of any of Embodiments 20-34.

Embodiment 41 provides a method of reducing or preventing progression of aging related hardening of arteries in a subject in need thereof, the method comprising administering to the subject a therapeutically effective amount of the polypeptide fusion of any of Embodiments 1-19 and 33-34 or the mutant polypeptide of any of Embodiments 20-34.

Embodiment 42 provides the method of Embodiment 35, wherein the pathological calcification is selected from the group consisting of idiopathic infantile arterial calcification (IIAC) and calcification of atherosclerotic plaques.

Embodiment 43 provides the method of Embodiment 36, wherein the pathological ossification is selected from the group consisting of ossification of the posterior longitudinal ligament (OPLL), hypophosphatemic rickets, and osteoarthritis.

Embodiment 44 provides the method of Embodiment 37, wherein the soft tissue calcification is selected from the group consisting of IIAC and osteoarthritis.

Embodiment 45 provides the method of Embodiment 37, wherein the soft tissue is selected from the group consisting of atherosclerotic plaques, muscular arteries, joint, spine, articular cartilage, vertebral disk cartilage, vessels, and connective tissue.

Embodiment 46 provides a method of raising pyrophosphate (PPi) levels in a subject having PPi level lower than PPi normal level, the method comprising administering to the subject a therapeutically effective amount of a polypeptide of the polypeptide fusion of any of Embodiments 1-19 and 33-34 or the mutant polypeptide of any of Embodiments 20-34, whereby upon the administration the level of the PPi in the subject is elevated to a normal level of at least 2 μM and is maintained at approximately the same level.

Embodiment 47 provides a method of reducing or preventing the progression of pathological calcification or ossification in a subject having pyrophosphate (PPi) level lower than PPi normal level, the method comprising administering to the subject a therapeutically effective amount of a polypeptide fusion of any of Embodiments 1-19 and 33-34 or the mutant polypeptide of any of Embodiments 20-34, whereby pathological calcification or ossification in the subject is reduced or progression of pathological calcification or ossification in the subject is prevented.

Embodiment 48 provides a method of treating ENPP1 deficiency manifested by a reduction of extracellular pyrophosphate (PPi) concentration in a subject in need thereof, the method comprising administering to the subject a therapeutically effective amount of a polypeptide fusion of any of Embodiments 1-19 and 33-34 or the mutant polypeptide of any of Embodiments 20-34, whereby the level of the PPi in the subject is elevated.

Embodiment 49 provides the method of any of Embodiments 35-48, wherein the polypeptide fusion or mutant polypeptide is a secreted product of a ENPP1 precursor protein expressed in a mammalian cell, wherein the ENPP1 precursor protein comprises a signal peptide sequence and an ENPP1 polypeptide, wherein the ENPP1 precursor protein undergoes proteolytic processing to yield the ENPP1 polypeptide.

Embodiment 50 provides the method of Embodiment 49, wherein in the ENPP1 precursor protein the signal peptide sequence is conjugated to the N-terminus of the ENPP1 polypeptide.

Embodiment 51 provides the method of any of Embodiments 49-50, wherein the signal peptide sequence is selected from the group consisting of ENPP1 signal peptide sequence, ENPP2 signal peptide sequence, ENPP7 signal peptide sequence, and ENPP5 signal peptide sequence.

Embodiment 52 provides the method of any of Embodiments 35-51, wherein the polypeptide fusion or mutant polypeptide is administered acutely or chronically to the subject.

Embodiment 53 provides the method of any of Embodiments 35-52, wherein the polypeptide fusion or mutant polypeptide is administered locally, regionally, parenterally, or systemically to the subject.

Embodiment 54 provides the method of any of Embodiments 35-53, wherein the polypeptide fusion or mutant polypeptide is administered to the subject by at least one route selected from the group consisting of subcutaneous, oral, aerosol, inhalational, rectal, vaginal, transdermal, subcutaneous, intranasal, buccal, sublingual, parenteral, intrathecal, intragastrical, ophthalmic, pulmonary, and topical.

Embodiment 55 provides the method of any of Embodiments 35-54, wherein the polypeptide fusion or mutant polypeptide is administered to the subject as a pharmaceutical composition further comprising at least one pharmaceutically acceptable carrier.

Embodiment 56 provides the method of any of Embodiments 35-55, wherein the subject is a mammal.

Embodiment 57 provides the method of Embodiment 56, wherein the mammal is human.

Embodiment 58 provides an ENPP1 mutant polypeptide comprising one or more amino acid substitutions as relating to SEQ ID NO:7, wherein the polypeptide comprises an amino acid substitution at position 256 relative to SEQ ID NO:7.

Embodiment 59 provides the ENPP1 mutant polypeptide of Embodiment 58, wherein the ENPP1 mutant polypeptide amino acid sequence is at least 90% identical to amino acids 23-849 of SEQ ID NO:7.

Embodiment 60 provides an ENPP1 mutant polypeptide comprising amino acids 23-849 of SEQ ID NO:7, wherein no more than ten (10) amino acid substitutions relative to amino acids 23-849 of SEQ ID NO:7 are present, and wherein the ENPP1 mutant polypeptide comprises an amino acid substitution at position 256 relative to SEQ ID NO:7.

Embodiment 61 provides the ENPP1 mutant polypeptide of any one of Embodiments 58-60, wherein the amino acid substitution is the substitution of isoleucine (I) for threonine (T) at position 256 relative to SEQ ID NO:7.

Embodiment 62 provides the ENPP1 mutant polypeptide of any one of Embodiments 58-60, wherein the amino acid substitution is the substitution of isoleucine (I) for serine(S) at position 256 relative to SEQ ID NO:7.

Embodiment 63 provides an ENPP1 mutant polypeptide comprising an amino acid sequence that is at least 90% identical to amino acids 23-849 of SEQ ID NO:7, wherein the mutant polypeptide comprises mutation I256T as relating to SEQ ID NO:7, and wherein the mutant polypeptide further comprises a mutation selected from the group consisting of S766N, P534N, V536T, P554L, R545T, and E592N as relating to SEQ ID NO:7.

Embodiment 64 provides the ENPP1 mutant polypeptide of Embodiment 63, wherein the mutant polypeptide comprises at least one amino acid substitution selected from the group consisting of S766N, P534N/V536T, P554L/R545T, and E592N as relating to SEQ ID NO:7.

Embodiment 65 provides the ENPP1 mutant polypeptide of Embodiment 63, wherein the mutant polypeptide comprises the amino acid substitution V29N.

Embodiment 66 provides the ENPP1 mutant polypeptide of any one of Embodiments 58-61, wherein the mutant polypeptide comprises the amino acid sequence of SEQ ID NO: 11.

Embodiment 67 provides an ENPP1 mutant polypeptide fusion comprising the ENPP1 mutant polypeptide of any one of Embodiments 58-66 and a heterologous protein.

Embodiment 68 provides the ENPP1 mutant polypeptide fusion of Embodiment 67, wherein the heterologous protein is an FcRn binding domain.

Embodiment 69 provides the ENPP1 mutant polypeptide fusion of any one of Embodiments 67-68, wherein the heterologous protein is carboxy-terminal to the ENPP1 mutant polypeptide of the fusion.

Embodiment 70 provides the ENPP1 mutant polypeptide fusion of any one of Embodiments 67-68, wherein the heterologous protein is amino-terminal to the ENPP1 mutant polypeptide of the fusion.

Embodiment 71 provides the ENPP1 mutant polypeptide fusion of any one of Embodiments 68-70, wherein the FcRn binding domain is an albumin polypeptide.

Embodiment 72 provides the ENPP1 mutant polypeptide fusion of any one of Embodiments 68-70, wherein the FcRn binding domain is a Fc portion of an immunoglobulin molecule.

Embodiment 73 provides the ENPP1 mutant polypeptide fusion of Embodiment 72, wherein the immunoglobulin molecule is an IgG1.

Embodiment 74 provides the ENPP1 mutant polypeptide fusion of any one of Embodiments 68-73, wherein the FcRn binding domain comprises one more amino acid substitutions relative to a wild type FcRn binding domain.

Embodiment 75 provides the ENPP1 mutant polypeptide fusion of any one of Embodiments 68-70 and 72-74, wherein the FcRn binding domain is the Fc portion of a human IgG1 molecule and comprises the following amino acid substitutions: M883Y, S885T, and T887E, each relative to SEQ ID NO:7.

Embodiment 76 provides the ENPP1 mutant polypeptide fusion of any one of Embodiments 68-70 and 72-75, wherein the fusion comprises one or more of the following substitutions: S885N, S766N, M883Y/S885T/T887E, P534N/V536T/H1064K/N1065F, P554L/R545T, S766N/H1064K/N1065F, E592N/H1064K/N1065F, or P534N/V536T/M883Y/S885T/T887E, each as relating to SEQ ID NO:7.

Embodiment 77 provides the ENPP1 mutant polypeptide fusion of any one of Embodiments 68-70 and 72-76, wherein the fusion comprises the S885N mutation as relating to SEQ ID NO:7.

Embodiment 78 provides the ENPP1 mutant polypeptide fusion of any one of Embodiments 68-70 and 72-77, wherein the fusion comprises the S766N mutation as relating to SEQ ID NO:7.

Embodiment 79 provides the ENPP1 mutant polypeptide fusion of any one of Embodiments 68-70 and 72-78, wherein the fusion comprises mutations M883Y, S885T, and T887E as relating to SEQ ID NO:7.

Embodiment 80 provides the ENPP1 mutant polypeptide fusion of any one of Embodiments 68-70 and 72-79, wherein the fusion comprises mutations P534N, V536T, H1064K, and N1065F as relating to SEQ ID NO:7.

Embodiment 81 provides the ENPP1 mutant polypeptide fusion of any one of Embodiments 68-70 and 72-80, wherein the fusion comprises mutations P554L and R545T as relating to SEQ ID NO:7.

Embodiment 82 provides the ENPP1 mutant polypeptide fusion of any one of Embodiments 68-70 and 72-81, wherein the fusion comprises mutation S766N, H1064K, and N1065F as relating to SEQ ID NO:7.

Embodiment 83 provides the ENPP1 mutant polypeptide fusion of any one of Embodiments 68-70 and 72-82, wherein the fusion comprises mutation E592N, H1064K, and N1065F as relating to SEQ ID NO:7.

Embodiment 84 provides the ENPP1 mutant polypeptide fusion of any one of Embodiments 68-70 and 72-83, wherein the fusion comprises mutations P534N, V536T, M883Y, S885T, and T887E as relating to SEQ ID NO:7.

Embodiment 85 provides the ENPP1 mutant polypeptide fusion of any one of Embodiments 68-70 and 72-84, wherein the Fc region comprises at least one mutation selected from the group consisting of M883Y, S885N, S885T, T887E, H1064K, and N1065F as relating to SEQ ID NO:7.

Embodiment 86 provides the ENPP1 mutant polypeptide fusion of any one of Embodiments 68-70 and 72-85, wherein the Fc region comprises at least one mutation selected from the group consisting of S885N, M883Y, M883Y/S885T/T887E, and H1064K/N1065F as relating to SEQ ID NO:7.

Embodiment 87 provides the ENPP1 mutant polypeptide fusion of any one of Embodiments 68-70 and 72-86 or the ENPP1 mutant polypeptide of any one of Embodiments 58-65, wherein the fusion comprises at least one mutation selected from the group consisting of C25N, K27T, and V29N as relating to SEQ ID NO:7.

Embodiment 88 provides the ENPP1 mutant polypeptide fusion of any one of Embodiments 68-70 and 72-87 or the ENPP1 mutant polypeptide of any one of Embodiments 58-65 and 85, wherein the fusion or the ENPP1 mutant polypeptide comprises at least one mutation selected from the group consisting of C25N/K27T and V29N as relating to SEQ ID NO: 7.

Embodiment 89 provides the ENPP1 mutant polypeptide fusion of any one of Embodiments 68-70 and 72-88 or the ENPP1 mutant polypeptide of any one of Embodiments 58-65 and 87-88, wherein the fusion or the ENPP1 mutant polypeptide comprises one mutation selected from the group consisting of K369N and I371T as relating to SEQ ID NO: 7.

Embodiment 90 provides the ENPP1 mutant polypeptide fusion of any one of Embodiments 68-70 and 72-89 or the ENPP1 mutant polypeptide of any one of Embodiments 58-65 and 87-89, wherein the fusion or ENPP1 mutant polypeptide comprises the mutation K369N/I371T as relating to SEQ ID NO:7.

Embodiment 91 provides the ENPP1 mutant polypeptide fusion of any one of Embodiments 68-70 and 72-90 or the ENPP1 mutant polypeptide of any one of Embodiments 58-65 and 87-90, wherein the fusion or ENPP1 mutant polypeptide comprises at least one mutation selected from the group consisting of P534N, V536T, R545T, P554L, E592N, R741D, and S766N as relating to SEQ ID NO:7.

Embodiment 92 provides the ENPP1 mutant polypeptide fusion of any one of Embodiments 68-70 and 72-91 or the ENPP1 mutant polypeptide of any one of Embodiments 58-65 and 87-91, wherein the fusion or ENPP1 mutant polypeptide comprises at least one mutation selected from the group consisting of P534N/V536T, P554L/R545T, E592N, E592N/R741D, and S766N as relating to SEQ ID NO:7.

Embodiment 93 provides the ENPP1 mutant polypeptide fusion of any one of Embodiments 68-70 and 72-92 or the ENPP1 mutant polypeptide of any one of Embodiments 58-65 and 87-92, wherein the fusion or ENPP1 mutant polypeptide comprises at least one mutation selected from the group consisting of C25N, K27T, V29N, C25N/K27T, K369N, I371T, K369N/I371T, P534N, V536T, R545T, P554L, E592N, R741D, S766N, P534N/V536T, P554L/R545T, E592N/R741D, E864N, L866T, E864N/L866T, M883Y, S885N, S885T, T887E, H1064K, N1065F, M883Y/S885T/T887E, H1064K/N1065F as relating to SEQ ID NO:7.

Embodiment 94 provides the ENPP1 mutant polypeptide fusion of any one of Embodiments 68-70 and 72-93 or the ENPP1 mutant polypeptide of any one of Embodiments 58-65 and 87-93, wherein the fusion or ENPP1 mutant polypeptide comprises at least one mutation selected from the group consisting of P534N, V536T, R545T, P554L, S766N, and E592N as relating to SEQ ID NO:7.

Embodiment 95 provides the ENPP1 mutant polypeptide fusion of any one of Embodiments 68-70 and 72-94 or the ENPP1 mutant polypeptide of any one of Embodiments 58-65 and 87-94, wherein the fusion or ENPP1 mutant polypeptide comprises at least one mutation selected from the group consisting of S766N, P534N/Y536T, P554L/R545T, and E592N as relating to SEQ ID NO:7.

Embodiment 96 provides the ENPP1 mutant polypeptide fusion of any one of Embodiments 68-70 and 72-95 or the ENPP1 mutant polypeptide of any one of Embodiments 58-65 and 87-95, wherein the fusion or ENPP1 mutant polypeptide comprises at least one mutation selected from the group consisting of S885N, S766N, M883Y/S885T/T887E, E864N/L866T, P534N/V536T/H1064K/N1065F, P554L/R545T, S766N/H1064K/N1065F, E592N/H1064K/N1065F, and P534N/V536T/M883Y/S885T/T887E as relating to SEQ ID NO: 7.

Embodiment 97 provides the ENPP1 mutant polypeptide fusion of any one of Embodiments 68-70 and 72-96, wherein the fusion comprises mutations I256T, M883Y, S885T, and T887E as relating to SEQ ID NO:7.

Embodiment 98 provides the ENPP1 mutant polypeptide fusion of any one of Embodiments 68-70 and 72-96, wherein the fusion comprises mutations I256T, P534N, V536T, M883Y, S885T, and T887E as relating to SEQ ID NO:7.

Embodiment 99 provides the ENPP1 mutant polypeptide fusion of any one of Embodiments 68-70 and 72-96, wherein the fusion comprises mutations I256T, E592N, H1064K, and N1065F as relating to SEQ ID NO:7.

Embodiment 100 provides the fusion of any one of Embodiments 67-99, comprising a linker amino acid sequence.

Embodiment 101 provides the fusion of Embodiment 100, wherein the linker amino acid sequence connects the ENPP1 mutant polypeptide portion of the fusion and the heterologous protein.

Embodiment 102 provides the fusion of any one of Embodiments 100-101, wherein the linker amino acid sequence comprises SEQ ID NO:8 or SEQ ID NO:9.

Embodiment 103 provides a nucleic acid encoding the ENPP1 mutant polypeptide of any one of Embodiments 58-66 or the fusion of any one of Embodiments 67-102.

Embodiment 104 provides a vector comprising the nucleic acid of Embodiment 103.

Embodiment 105 provides an expression vector comprising the nucleic acid of Embodiment 103.

Embodiment 106 provides a cell or plurality of cells, each comprising the nucleic acid of Embodiment 103, the vector of Embodiment 104, and/or the expression vector of Embodiment 105.

Embodiment 107 provides the cell or plurality of cells of Embodiment 106, wherein the cell(s) is/are a CHO cell(s) and/or an NSO cell(s).

Embodiment 108 provides the cell or plurality of cells of Embodiment 107, wherein the CHO cell is stably transfected with human ST6 beta-galactoside alpha-2,6-sialyltransferase.

Embodiment 109 provides a method of producing an ENPP1 mutant polypeptide or fusion, the method comprising culturing the cell or plurality of cells of any one of Embodiments 106-108, under conditions suitable for expression of the ENPP1 mutant polypeptide or fusion by the cell or cells.

Embodiment 110 provides the method of Embodiment 109, wherein the cells are cultured in a medium supplemented with sialic acid and/or N-acetylmannosamine.

Embodiment 111 provides the method of any one of Embodiments 109-110, further comprising purifying the ENPP1 mutant polypeptide or fusion from the cell, plurality of cells, or the media in which the cell or plurality of cells were cultured.

Embodiment 112 provides an ENPP1 mutant polypeptide or fusion purified by the method of Embodiment 111.

Embodiment 113 provides a conjugate comprising (i) the ENPP1 mutant polypeptide of any one of Embodiments 58-66, 87-96, and 112 and/or the ENPP1 mutant polypeptide fusion of any one of Embodiments 67-102 and 112 and (ii) a heterologous moiety.

Embodiment 114 provides the conjugate of Embodiment 113, wherein the heterologous moiety is polyethylene glycol.

Embodiment 115 provides a pharmaceutical composition comprising the ENPP1 mutant polypeptide of any one of Embodiments 58-66, 87-96, and 112, the fusion of any one of Embodiments 67-102 and 112, the nucleic acid of Embodiment 103, the vector of Embodiment 104, the expression vector of Embodiment 105, and/or the conjugate of any one of Embodiments 113-114 and a pharmaceutically acceptable carrier.

Embodiment 116 provides a method of reducing or preventing progression of pathological calcification in a subject in need thereof, the method comprising administering to the subject a therapeutically effective amount of: (a) the ENPP1 mutant polypeptide of any one of Embodiments 58-66, 87-96, and 112; (b) the fusion of any one of Embodiments 67-102 and 112; (c) the conjugate of any one of Embodiments 113-114; and/or (d) the pharmaceutical composition of Embodiment 115, to thereby reduce or prevent progression of pathological calcification in the subject.

Embodiment 117 provides a method of reducing or preventing progression of pathological ossification in a subject in need thereof, the method comprising administering to the subject a therapeutically effective amount of: (a) the ENPP1 mutant polypeptide of any one of Embodiments 58-66, 87-96, and 112; (b) the fusion of any one of Embodiments 67-102 and 112; (c) the conjugate of any one of Embodiments 113-114; and/or (d) the pharmaceutical composition of Embodiment 115, to thereby reduce or prevent progression of pathological ossification in the subject.

Embodiment 118 provides a method of reducing or preventing progression of ectopic calcification of soft tissue in a subject in need thereof, the method comprising administering to the subject a therapeutically effective amount of: (a) the ENPP1 mutant polypeptide of any one of Embodiments 58-66, 87-96, and 112; (b) the fusion of any one of Embodiments 67-102 and 112; (c) the conjugate of any one of Embodiments 113-114; and/or (d) the pharmaceutical composition of Embodiment 115, to thereby reduce or prevent progression of ectopic calcification of soft tissue in the subject.

Embodiment 119 provides a method of treating, reversing, or preventing progression of ossification of the posterior longitudinal ligament (OPLL) in a subject in need thereof, the method comprising administering to the subject a therapeutically effective amount of: (a) the ENPP1 mutant polypeptide of any one of Embodiments 58-66, 87-96, and 112; (b) the fusion of any one of Embodiments 67-102 and 112; (c) the conjugate of any one of Embodiments 113-114; and/or (d) the pharmaceutical composition of Embodiment 115, to thereby reduce, reverse, or prevent ossification of the posterior longitudinal ligament (OPLL) in the subject.

Embodiment 120 provides a method of treating, reverting, or preventing progression of hypophosphatemic rickets in a subject in need thereof, the method comprising administering to the subject a therapeutically effective amount of: (a) the ENPP1 mutant polypeptide of any one of Embodiments 58-66, 87-96, and 112; (b) the fusion of any one of Embodiments 67-102 and 112; (c) the conjugate of any one of Embodiments 113-114; and/or (d) the pharmaceutical composition of Embodiment 115, to thereby reduce, reverse, or prevent progression of hypophosphatemic rickets in the subject.

Embodiment 121 provides a method of reducing or preventing progression of at least one disease selected from the group consisting of chronic kidney disease (CKD), end stage renal disease (ESRD), calcific uremic arteriolopathy (CUA), calciphylaxis, ossification of the posterior longitudinal ligament (OPLL), hypophosphatemic rickets, osteoarthritis, aging related hardening of arteries, idiopathic infantile arterial calcification (IIAC), Generalized Arterial Calcification of Infancy (GACI), and calcification of atherosclerotic plaques in a subject diagnosed with the at least one disease, the method comprising administering to the subject a therapeutically effective amount of: (a) the ENPP1 mutant polypeptide of any one of Embodiments 58-66, 87-96, and 112; (b) the fusion of any one of Embodiments 67-102 and 112; (c) the conjugate of any one of Embodiments 113-114; and/or (d) the pharmaceutical composition of Embodiment 115, to thereby reduce or prevent progression of the disease.

Embodiment 122 provides a method of reducing or preventing progression of aging related hardening of arteries in a subject in need thereof, the method comprising administering to the subject a therapeutically effective amount of: (a) the ENPP1 mutant polypeptide of any one of Embodiments 58-66, 87-96, and 112; (b) the fusion of any one of Embodiments 67-102 and 112; (c) the conjugate of any one of Embodiments 113-114; and/or (d) the pharmaceutical composition of Embodiment 115, to thereby reduce or prevent progression of aging related hardening of arteries in the subject.

Embodiment 123 provides a method of raising pyrophosphate (PPi) levels in a subject having PPi level lower than PPi normal level, the method comprising administering to the subject a therapeutically effective amount of: (a) the ENPP1 mutant polypeptide of any one of Embodiments 58-66, 87-96, and 112; (b) the fusion of any one of Embodiments 67-102 and 112; (c) the conjugate of any one of Embodiments 113-114; and/or (d) the pharmaceutical composition of Embodiment 115, whereby upon the administration the level of the PPi in the subject is elevated to a normal level of at least 2 μM and is maintained at approximately the same level.

Embodiment 124 provides a method of reducing or preventing the progression of pathological calcification or ossification in a subject having pyrophosphate (PPi) level lower than PPi normal level, the method comprising administering to the subject a therapeutically effective amount of: (a) the ENPP1 mutant polypeptide of any one of Embodiments 58-66, 87-96, and 112; (b) the fusion of any one of Embodiments 67-102 and 112; (c) the conjugate of any one of Embodiments 113-114; and/or (d) the pharmaceutical composition of Embodiment 115, whereby pathological calcification or ossification in the subject is reduced or progression of pathological calcification or ossification in the subject is prevented.

Embodiment 125 provides a method of treating ENPP1 deficiency manifested by a reduction of extracellular pyrophosphate (PPi) concentration in a subject in need thereof, the method comprising administering to the subject a therapeutically effective amount of: (a) the ENPP1 mutant polypeptide of any one of Embodiments 58-66, 87-96, and 112; (b) the fusion of any one of Embodiments 67-102 and 112; (c) the conjugate of any one of Embodiments 113-114; and/or (d) the pharmaceutical composition of Embodiment 115, whereby the level of the PPi in the subject is elevated.

Embodiment 126 provides the method of any one of Embodiments 116-125, wherein the mutant polypeptide, fusion, conjugate, or pharmaceutical composition is administered acutely or chronically to the subject.

Embodiment 127 provides the method of any one of Embodiments 116-126, wherein the mutant polypeptide, fusion, conjugate, or pharmaceutical composition is administered locally, regionally, parenterally, or systemically to the subject.

Embodiment 128 provides the method of any one of Embodiments 116-127, wherein the subject is human.

The disclosures of each and every patent, patent application, and publication cited herein are hereby incorporated herein by reference in their entirety. While this disclosure has been disclosed with reference to specific embodiments, it is apparent that other embodiments and variations of this disclosure may be devised by others skilled in the art without departing from the true spirit and scope of the disclosure. The appended claims are intended to be construed to include all such embodiments and equivalent variations.

What is claimed:

1. An ectonucleotide pyrophosphatase/phosphodiesterase 1 (ENPP1) polypeptide fusion comprising an ENPP1 polypeptide fused to a Fc region of an immunoglobulin, wherein the ENPP1 polypeptide comprises the mutation I256T as relating to SEQ ID NO: 7, wherein the ENPP1 polypeptide comprises the amino acid sequence of SEQ ID NO:11, and wherein the ENPP1 polypeptide fusion has enzymatic activity.

2. The ENPP1 polypeptide fusion of claim 1, wherein the Fc region comprises the amino acid residues 852-1078 of SEQ ID NO: 7, and:

i. wherein the Fc region further comprises at least one mutation selected from the group consisting of M883Y, S885N, S885T, T887E, H1064K, and N1065F as relating to SEQ ID NO:7;

ii. wherein the Fc region further comprises at least two mutations selected from the group consisting of M883Y, S885N, S885T, T887E, and H1064K, and N1065F as relating to SEQ ID NO: 7;

iii wherein the ENPP1 polypeptide further comprises at least one mutation selected from the group consisting of C25N, K27T, and V29N as relating to SEQ ID NO:7;

iv. wherein the ENPP1 polypeptide further comprises mutations C25N and K27T as relating to SEQ ID NO:7;

V. wherein the ENPP1 polypeptide further comprises at least one mutation selected from the group consisting of K369N and 1371T as relating to SEQ ID NO: 7;

vi. wherein the ENPP1 polypeptide further comprises the mutations K369N and I371T as relating to SEQ ID NO:7;

vii. wherein the ENPP1 polypeptide further comprises at least two mutations selected from the group consisting of P534N, V536T, R545T, P554L, E592N, R741D, and S766N as relating to SEQ ID NO:7;

viii. wherein the ENPP1 polypeptide further comprises at least one mutation selected from the group consisting of P534N, V536T, R545T, P554L, E592N, R741D, and S766N as relating to SEQ ID NO:7;

ix. wherein the ENPP1 polypeptide further comprises at least one mutation selected from the group consisting of E864N and L866T as relating to SEQ ID NO:7;

x. wherein the ENPP1 polypeptide further comprises at least the mutations E864N and L866T as relating to SEQ ID NO:7; or xi. wherein the ENPP1 polypeptide fusion further comprises at least one mutation selected from the group consisting of C25N, K27T, V29N, K369N, I371T, P534N, V536T, R545T, P554L, E592N, R741D, S766N, E864N, L866T, M883Y, S885N, S885T, and T887E, as relating to SEQ ID NO:7;

xii. wherein the Fc region further comprises mutations M883Y, S885T, and T887E as relating to SEQ ID NO:7;

xiii. wherein the Fc region further comprises mutations H1064K and N1065F as relating to SEQ ID NO:7;

xiv. wherein the ENPP1 polypeptide further comprises mutations P534N and V536T as relating to SEQ ID NO:7;

XV. wherein the ENPP1 polypeptide further comprises mutations R545T and P554L as relating to SEQ ID NO:7;

xvi. wherein the ENPP1 polypeptide further comprises mutations E592N and R741D as relating to SEQ ID NO:7;

xvii. wherein the ENPP1 polypeptide further comprises mutations R545T, P554L, E592N, and R741D as relating to SEQ ID NO:7; or xviii. wherein the ENPP1 polypeptide fusion further comprises mutations M883Y, S885T, T887E, H1064K, and N1065F as relating to SEQ ID NO:7.

3. The ENPP1 polypeptide fusion of claim 1, wherein the Fc region comprises the amino acid residues 852-1078 of SEQ ID NO: 7 further comprising:

i. at least one mutation selected from the group consisting of P534N, V536T, R545T, P554L, S766N, and E592N as relating to SEQ ID NO:7;

ii. at least one mutation selected from the group consisting of P534N, V536T, R545T, P554L, E592N, and S766N as relating to SEQ ID NO:7;

iii. mutations P534N and Y536T as relating to SEQ ID NO:7;

iv. mutations R545T and P554L as relating to SEQ ID NO:7;

v. mutations P534N, V536T, H1064K, and N1065F as relating to SEQ ID NO: 7;

vi. mutations S766N, H1064K, and N1065F as relating to SEQ ID NO:7;

vii. mutations E592N, H1064K, and N1065F as relating to SEQ ID NO:7; or viii. mutations P534N, V536T, M883Y, S885T, and T887E as relating to SEQ ID NO: 7.

4. A pharmaceutical composition comprising an ENPP1 mutant polypeptide, wherein the ENPP1 mutant polypeptide comprises an ENPP1 polypeptide fused to a Fc region of an immunoglobulin, wherein the ENPP1 mutant polypeptide comprises the amino acid sequence of SEQ ID NO: 11, and wherein the ENPP1 mutant polypeptide comprises mutation I256T as relating to SEQ ID NO: 7.

5. The pharmaceutical composition of claim 4, wherein the ENPP1 mutant polypeptide further comprises a mutation selected from the group consisting of P534N, V536T, R545T, P554L, E592N, and S766N as relating to SEQ ID NO: 7.

6. The pharmaceutical composition of claim 4, i. wherein the ENPP1 mutant polypeptide further comprises at least one mutation selected from the group consisting of P534N, V536T, R545T, P554L, and E592N, and S766N as relating to SEQ ID NO:7;

ii. wherein the ENPP1 mutant polypeptide further comprises a S766N mutation as relating to SEQ ID NO:7;

iii. wherein the ENPP1 mutant polypeptide further comprises mutations R545T and P554L as relating to SEQ ID NO:7; or iv. wherein the ENPP1 mutant polypeptide further comprises mutations P534N and V536T as relating to SEQ ID NO: 7.

7. The pharmaceutical composition of claim 4, wherein the Fc region comprises the amino acid residues 852-1078 of SEQ ID NO: 7, and wherein the ENPP1 polypeptide fusion:

i. further comprises at least one mutation selected from the group consisting of: P534N, V536T, R545T, P554L, E592N, S766N M883Y, S885N, S885T, T887E, H1064K, and N1065F as relating to SEQ ID NO:7;

ii. further comprises a S885N mutation as relating to SEQ ID NO: 7;

iii. further comprises mutations M883Y, S885T, and T887E as relating to SEQ ID NO:7;

iv. further comprises mutations P534N, V536T, H1064K, and N1065F as relating to SEQ ID NO:7;

v. further comprises mutations S766N, H1064K, and N1065F as relating to SEQ ID NO:7;

vi. further comprises mutations E592N, H1064K, and N1065F as relating to SEQ ID NO:7; or vii. further comprises mutations P534N, V536T, M883Y, S885T, and T887E as relating to SEQ ID NO:7.

8. The pharmaceutical composition of claim 4, wherein the ENPP1 mutant polypeptide is expressed from a CHO cell line stably transfected with human ST6 beta-galactoside alpha-2,6-sialyltransferase (ST6GAL1).

9. The pharmaceutical composition of claim 4, wherein the ENPP1 mutant polypeptide is grown in a cell culture supplemented with at least one of sialic acid and N-acetylmannosamine (1,3,4-O-Bu3ManNAc).

10. A method of reducing or preventing progression of pathological calcification or pathological ossification in a subject in need thereof, the method comprising administering to the subject a therapeutically effective amount of an ectonucleotide pyrophosphatase/phosphodiesterase 1 (ENPP1) polypeptide fusion comprising an ENPP1 polypeptide fused to a Fc region of an immunoglobulin, wherein the ENPP1 polypeptide comprises the mutation 1256T as relating to SEQ ID NO: 7, wherein the ENPP1 polypeptide comprises the amino acid sequence of SEQ ID NO: 11, and wherein the ENPP1 polypeptide fusion has enzymatic activity.

11. The method of claim 10, wherein the pathological calcification is ectopic calcification of soft tissue.

12. The method of claim 10, wherein the pathological ossification is selected from the group consisting of ossification of the posterior longitudinal ligament (OPLL), hypophosphatemic rickets, and osteoarthritis.

13. The method of claim 10, wherein the pathological calcification is selected from the group consisting of generalized arterial calcification of infancy (GACI) and calcification of atherosclerotic plaques.

14. The method of claim 10, wherein the subject has at least one disease selected from the group consisting of chronic kidney disease (CKD), end stage renal disease (ESRD), calcific uremic arteriolopathy (CUA), calciphylaxis, ossification of the posterior longitudinal ligament (OPLL), hypophosphatemic rickets, osteoarthritis, aging related hardening of arteries, idiopathic infantile arterial calcification (IIAC), generalized arterial calcification of infancy (GACI), and calcification of atherosclerotic plaques.

15. The method of claim 11, wherein the soft tissue is selected from the group consisting of atherosclerotic plaques, muscular arteries, joint, spine, articular cartilage, vertebral disk cartilage, vessels, and connective tissue.

16. The method of claim 10, wherein the subject has ENPP1 deficiency manifested by a reduction of extracellular pyrophosphate (PPi) concentration.

17. The method of claim 10, wherein the subject has a PPi extracellular level lower than the PPi normal extracellular level, whereby upon the administration of the ENPP1 polypeptide fusion, the PPi extracellular level in the subject is elevated to a normal extracellular level of at least 2 μM and is maintained at approximately the same level.

18. The method of claim 10, wherein the ENPP1 polypeptide fusion is administered locally, regionally, parenterally, or systemically to the subject.

19. The method of claim 10, wherein the ENPP1 polypeptide fusion is administered to the subject by at least one route selected from the group consisting of subcutaneous, oral, aerosol, inhalational, rectal, vaginal, transdermal, subcutaneous, intranasal, buccal, sublingual, parenteral, intrathecal, intragastrical, ophthalmic, pulmonary, and topical.

20. The method of claim 10, wherein the ENPP1 polypeptide fusion is administered to the subject as a pharmaceutical composition further comprising at least one pharmaceutically acceptable carrier.

21. The method of claim 20, wherein the subject is a human.

* * * * *